(12) United States Patent
Park et al.

(10) Patent No.: US 12,172,945 B2
(45) Date of Patent: *Dec. 24, 2024

(54) AMINOALKANOIC ACID DERIVATIVE CONTAINING BIPHENYL GROUP AND USE OF THE SAME

(71) Applicant: AMTIXBIO CO., LTD., Seoul (KR)

(72) Inventors: Ki Duk Park, Seoul (KR); Jong Hyun Park, Seoul (KR); Hyeon Ji Kim, Seoul (KR); Ye Rim Lee, Seoul (KR); Siwon Kim, Seoul (KR); Ji Won Choi, Seoul (KR); Seul Ki Yeon, Seoul (KR); Jong-Seung Lee, Seoul (KR); Yong-Sun Bahn, Seoul (KR); Eunji Cheong, Seoul (KR); Kyung-Tae Lee, Seoul (KR); Joohyeon Hong, Seoul (KR)

(73) Assignee: AMTIXBIO CO., LTD., Seoul (KR)

( * ) Notice: Subject to any disclaimer, the term of this patent is extended or adjusted under 35 U.S.C. 154(b) by 18 days.

This patent is subject to a terminal disclaimer.

(21) Appl. No.: 17/948,162

(22) Filed: Sep. 19, 2022

(65) Prior Publication Data

US 2023/0067422 A1    Mar. 2, 2023

Related U.S. Application Data

(60) Division of application No. 17/562,956, filed on Dec. 27, 2021, now Pat. No. 11,479,526, which is a continuation of application No. PCT/KR2020/008306, filed on Jun. 25, 2020.

(30) Foreign Application Priority Data

Jun. 25, 2019 (KR) .................. 10-2019-0075893

(51) Int. Cl.
  *C07D 231/02* (2006.01)
  *C07C 231/02* (2006.01)
(52) U.S. Cl.
  CPC .................. *C07C 231/02* (2013.01)
(58) Field of Classification Search
  CPC .................................. C07C 231/02
  See application file for complete search history.

(56) References Cited

FOREIGN PATENT DOCUMENTS

| WO | 1998/003472 A1 | 1/1998 |
|----|----------------|--------|
| WO | 2010/088187 A1 | 8/2010 |
| WO | 2010/108187 A2 | 9/2010 |
| WO | 2012/125832 A2 | 9/2012 |
| WO | 2013/131018 A1 | 9/2013 |

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/Zregistry (CAS Registrysm) Sep. 2016 2 pages.*
Choi, Journal of Medicinal Chemistry (2021), 64(21), 15912-15935.*
Lee et al., "Substituted N-(Biphenyl-4'-yl)methyl (R)-2-Acetamido-3-methoxypropionamides: Potent Anticonvulsants That Affect Frequency (Use) Dependence and Slow Inactivation of Sodium Channels," Journal of Medicinal Chemistry, Jul. 8, 2014, vol. 57, No. 14, pp. 6165-6182.
Malkov et al., "Formamides derived from N-methyl amino acids serve as new chiral organocatalysts in the enantioselective reduction of aromatic ketimines with trichlorosilane," Tetrahedron, Jan. 9, 2006, vol. 62, Nos. 2-3, pp. 264-284.
U.S. Appl. No. 17/948,165, filed Sep. 19, 2022, Ki Duk Park.

* cited by examiner

*Primary Examiner* — Nizal S Chandrakumar
(74) *Attorney, Agent, or Firm* — United One Law Group LLC; Kongsik Kim; Jhongwoo Peck

(57) ABSTRACT

The present invention relates to a derivative compound in which a biphenyl group is introduced into an aminoalkanoic acid, a stereoisomer thereof, or a pharmaceutically acceptable salt thereof. The compound of the present invention exhibits excellent antifungal and fungicidal effects. Furthermore, the compound of the present invention exhibits a synergistic effect when used in combination with a conventional antifungal agent. Furthermore, the compound of the present invention provides broad-spectrum antifungal activity against a wide range of fungal pathogens. Therefore, the compound of the present invention may be widely used in fields requiring treatment with antifungal or fungicidal agents against human pathogenic fungi and animal pathogenic fungi, and phytopathogenic fungi.

11 Claims, 3 Drawing Sheets

AMINOALKANOIC ACID DERIVATIVE CONTAINING BIPHENYL GROUP AND USE OF THE SAME

CROSS-REFERENCE TO RELATED APPLICATION

The present application is a divisional application of U.S. application Ser. No. 17/562,956 filed Dec. 27, 2021, which is a continuation application of International Application No. PCT/KR2020/008306 filed Jun. 25, 2020, which claims priority to Korean Patent Application No. 10-2019-0075893 filed Jun. 25, 2019. The applications are incorporated herein by reference.

TECHNICAL FIELD

The present invention relates to a derivative compound in which a biphenyl group is introduced into an aminoalkanoic acid, a stereoisomer thereof, or a pharmaceutically acceptable salt thereof, and a pharmaceutical composition for preventing and/or treating a fungal infectious disease, including the same as an active ingredient.

BACKGROUND ART

The longer the life span of the contemporary people, the more opportunistic fungal infections increase especially among the elderly due to the decline of immune functions. Furthermore, infections by opportunistic infectious fungi are increasing worldwide, in particular among the immune-compromised patients who are treated with immunosuppressive agents to reduce a transplant rejection response, or the organ transplant patients with impaired immune functions, or patients with weakened immunity due to chemotherapy or acquired immunodeficiency syndrome (AIDS). For fungal infections in the past, local fungal infections such as athlete's foot, tinea cruris and thrush commonly occurred, but recently, systemic fungal infections have tended to occur so frequently that they are the fourth most common of all infection types in hospitals. As representative opportunistic pathogenic fungi, *Candida albicans, Candida glabrata, Candida krusei, Cryptococcus neoformans*, and the like have been reported. *Cryptococcus neoformans*, which is a pathogenic fungus causing systemic infections, is typically found in soil worldwide, and its basidiospores could be inhaled from the surrounding environment into the lungs through the human respiratory organs. In the case of patients with weakened immunity, such as organ transplant patients or patients with AIDS, fungi lurking in the lungs may evoke lung infections and penetrate into the central nervous system through the blood-brain barrier (BBB) to cause life-threatening encephalomeningitis. In particular, encephalomeningitis caused by *Cryptococcus* results in the highest mortality rate among encephalomeningitis, with more than 600,000 deaths worldwide each year. However, since fungi consist of eukaryotic cells like animal cells, the biochemical metabolic pathways of fungi and mammals are so similar that it is difficult to find fungal-specific drug target. Thus, conventional antifungal agents to treat cryptococcosis have a number of limitations in their clinical use. The antifungal agents developed so far to suppress *Cryptococcus* fungi include polyene class comprising amphotericin B; azole class comprising ketoconazole, fluconazole, itraconazole, and voriconazole; and non-azole class such as terbinafine and flucytosine; echinocandin class such as caspofungin. Amphotericin B, one of the polyene antifungals, binds to ergosterol in cell membrane of *Cryptococcus* to induce oxidative damage and causes fungal cell death. The amphotericin B, however, causes adverse effects resulting from its severe toxicity to the human body. Azole class antifungals are known to inhibit biosynthesis of ergosterol, one of the essential elements of fungal cell membrane, by inhibiting 14-α-demethylase which is involved in the conversion of lanosterol to ergosterol, thereby weakening the cell membrane and causing fungal cell death. It was reported, however, that emergence of azole resistance within fungal species has been increased. Terbinafine suppresses ergosterol synthesis by inhibiting the conversion of squalene to squalene epoxy. Flucytosine, which is a metabolic antagonist inhibiting nucleic acid synthesis, exhibits antifungal effects by causing fungal RNA miscoding and antagonizing fungal DNA synthesis. Echinocandin class antifungals reveal antifungal effects by inhibiting fungal cell wall synthesis while the other antifungal agents mentioned above act on fungal cell membrane. As disclosed above, the conventional antifungal agents or drugs have a number of problems of side effects such as severe toxicity and drug resistance development, etc. Therefore, it has been highly required to develop a new class antifungal agent which is capable of enhancing antifungal effects while minimizing side effects.

SUMMARY

The present invention is to provide a novel aminoalkanoic acid derivative containing a biphenyl group, a salt and/or a solvate thereof.

In addition, the present invention is to provide an antifungal pharmaceutical composition comprising the said aminoalkanoic acid derivative, a salt and/or a solvate thereof as an active ingredient.

In addition, the present invention is to provide an agricultural antifungal agent comprising the said aminoalkanoic acid derivative, a salt and/or a solvate thereof as an active ingredient.

Furthermore, the present invention is to provide an animal antifungal agent comprising the said aminoalkanoic acid derivative, a salt and/or a solvate thereof as an active ingredient.

Furthermore, the present invention is to provide an antifungal composition comprising the said aminoalkanoic acid derivative, a salt and/or a solvate thereof as an active ingredient.

Furthermore, the present invention is to provide a human body cleansing composition, cosmetic composition, or shampoo composition comprising the said aminoalkanoic acid derivative, a salt and/or a solvate thereof as an active ingredient.

Furthermore, an object of the present invention is to provide a method for preparing a benzyloxybenzylaminyl amino acid derivative of the present invention.

As one aspect to achieve the objects above, the present invention provides a compound represented by the following Formula 1, a stereoisomer thereof, or a pharmaceutically acceptable salt thereof:

[Formula 1]

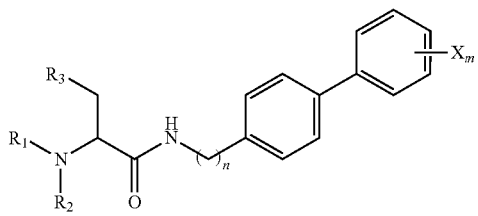

in the said Formula 1, n is 0, 1, 2, 3, 4 or 5, $R_1$, $R_2$, and $R_3$ are each independently the same as or different from each other, and are each independently selected from hydrogen, a $C_{1-7}$ alkyl, hydroxyl, a halogen, a halogenated $C_{1-7}$ alkyl, a $C_{1-7}$ alkyloxy and a halogenated $C_{1-7}$ alkyloxy, and X is m substituents (m is an integer from 1 to 5) which are the same as or different from each other, selected from the group consisting of a halogen group, a halogenated $C_{1-7}$ alkyl group and a halogenated $C_{1-7}$ alkoxy group.

In addition, the compound represented by the Formula 1 is a compound having no limitation on a 3D arrangement structure of a substituent attached to a chiral carbon, and may include all structurally available enantiomers or optical isomers. In particular, the compound represented by the Formula 1 may be provided in the form of a (R) or (S) isomer thereof alone or a mixture thereof, for example, a racemic mixture or racemate thereof, but not limited thereto.

In the present invention, the halogen may be selected from the group consisting of fluoro, chloro, bromo and iodo, and the $C_{1-7}$ alkyl may be a straight, branched or cyclic alkyl, and may be selected from the group consisting of methyl, ethyl, propyl, isopropyl, cyclopropyl, butyl, isobutyl, sec-butyl, t-butyl, pentyl, hexyl, heptyl and octyl.

The $C_{1-7}$ alkyloxy group may be selected from the group consisting of methoxy, ethoxy, propoxy, butoxy, pentoxy, hexyloxy, heptyloxy and octyloxy.

The halogenated $C_{1-7}$ alkyl may be selected from the group consisting of difluoromethyl, trifluoromethyl, difluoroethyl, trifluoroethyl, trifluoropropyl, trifluoropentyl, trifluorohexyl and trifluoroheptyl, and the halogenated $C_{1-7}$ alkyloxy may be selected from the group consisting of difluoromethyloxy, trifluoromethyloxy, difluoroethyloxy, trifluoroethyloxy, trifluoropropyloxy, trifluoropentyloxy, trifluorohexyloxy and trifluoroheptyloxy.

The present invention may include not only the said Formula 1 or a pharmaceutically acceptable salt thereof, but also a solvate or hydrate presenting the same effects, which can be prepared therefrom within the scope of the present invention.

The compound of the present invention is based on an aminoalkanoic acid and may be a derivative in which a biphenyl group is introduced into the aminoalkanoic acid.

For example, the aminoalkanoic acid may be an α-amino acid derivative containing a $C_{2-4}$ straight hydrocarbon chain in the side chain, for example, α-aminobutyric acid, norvaline or norleucine.

As used herein, the term "α-aminobutyric acid (AABA)" refers to a compound represented by the following Formula 6, which has an IUPAC name of 2-aminobutyric acid, and is a non-proteinogenic α-amino acid of formula $C_4H_9NO_2$, which is also known to be homoalanine in biochemistry. The α-aminobutyric acid includes a $C_2$ straight hydrocarbon chain in the side chain, which contains additional $C_1$ comparing to alanine.

[Formula 6]

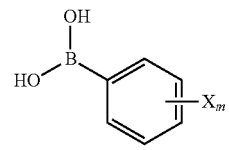

As used herein, the term "norvaline (Nva)" refers to a compound represented by the following Formula 7, which has an IUPAC name of 2-aminopentanoic acid, and is a water-soluble amino acid that is an isomer of valine, which is a branched chain amino acid (BCAA) of formula $CH_3(CH_2)_2CH(NH_2)CO_2H$.

[Formula 7]

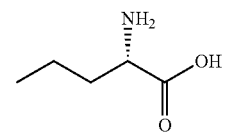

As used herein, the term "norleucine (Nle)" refer to a compound represented by the following Formula 8, which has an IUPAC name of 2-aminohexanoic acid, and is an amino acid having the formula $CH_3(CH_2)_3CH(NH_2)CO_2H$.

[Formula 8]

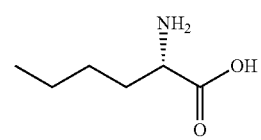

For example, the compound of the present invention may be a compound in which $R_1$ and $R_2$ are each independently H or methyl, ethyl, n-propyl, isopropyl, cyclopropyl, n-butyl, isobutyl, cyclobutyl, n-pentyl, cyclopentyl, n-hexyl or cyclohexyl, and $R_3$ is methyl, ethyl, n-propyl, isopropyl, cyclopropyl, n-butyl, isobutyl, sec-butyl or tert-butyl.

Furthermore, the compound of the present invention may be a compound in which $R_1$ and $R_2$ are each independently H or methyl, and $R_3$ is methyl, ethyl, or n-propyl, but not limited thereto.

For example, X in the compound of the present invention may be any one or two identical or different substituents selected from the group consisting of fluoro, chloro, trifluoromethyl and trifluoromethoxy. For example, the substituent may be one, or two or more which are the same as each other or differently selected.

For example, X in the compound of the present invention may be fluoro, chloro, trifluoromethyl or trifluoromethoxy, and in particular, X may be p-fluoro, m-fluoro, p,m-difluoro, p-chloro, m-chloro, p,m-dichloro, p-trifluoromethyl or p-trifluoromethoxy, but not limited thereto.

Specifically, non-limiting examples of the compound of the present invention may include:

1) 2-amino-N-(3',4'-dichloro-[1,1'-biphenyl]-4-yl)butanamide;

2) 2-amino-N-(3',4'-dichloro-[1,1'-biphenyl]-4-yl)pentanamide;
3) 2-amino-N-(3',4'-dichloro-[1,1'-biphenyl]-4-yl)hexanamide;
4) 2-amino-N-(4'-(trifluoromethoxy)-[1,1'-biphenyl]-4-yl)pentanamide;
5) N-(3',4'-dichloro-[1,1'-biphenyl]-4-yl)-2-(methylamino)butanamide;
6) N-(3',4'-dichloro-[1,1'-biphenyl]-4-yl)-2-(methylamino)pentanamide;
7) N-(3',4'-dichloro-[1,1'-biphenyl]-4-yl)-2-(methylamino)hexanamide;
8) N-(3',4'-dichloro-[1,1'-biphenyl]-4-yl)-2-(dimethylamino)pentanamide;
9) 2-amino-N((3',4'-dichloro-[1,1'-biphenyl]-4-yl)methyl)pentanamide;
10) 2-amino-N-((3',4'-dichloro-[1,1'-biphenyl]-4-yl)methyl)hexanamide;
11) 2-amino-N((4'-(trifluoromethyl)-[1,1'-biphenyl]-4-yl)methyl)pentanamide;
12) 2-amino-N((4'-(trifluoromethyl)-[1,1'-biphenyl]-4-yl)methyl)hexanamide;
13) 2-amino-N((4'-(trifluoromethoxy)-[1,1'-biphenyl]-4-yl)methyl)pentanamide;
14) 2-amino-N-((4'-(trifluoromethoxy)-[1,1'-biphenyl]-4-yl)methyl)hexanamide;
15) N-((3',4'-dichloro-[1,1'-biphenyl]-4-yl)methyl)-2-(methylamino)pentanamide;
16) 2-(methylamino)-N-((4'-(trifuloromethyl)-[1,1'-biphenyl]-4-yl)methyl)pentanamide;
17) N-((3',4'-dichloro-[1,1'-biphenyl]-4-yl)methyl)-2-(dimethylamino)pentanamide;
18) 2-amino-N-(2-(3',4'-dichloro-[1,1'-biphenyl]-4-yl)ethyl)butanamide;
19) 2-amino-N-(2-(3',4'-dichloro-[1,1'-biphenyl]-4-yl)ethyl)pentanamide;
20) 2-amino-N-(2-(3',4'-dichloro-[1,1'-biphenyl]-4-yl)ethyl)hexanamide;
21) 2-amino-N-(2-(4'-(trifluoromethyl)-[1,1'-biphenyl]-4-yl)ethyl)butanamide;
22) 2-amino-N-(2-(4'-(trifluoromethyl)-[1,1'-biphenyl]-4-yl)ethyl)pentanamide;
23) 2-amino-N-(2-(4'-(trifluoromethyl)-[1,1'-biphenyl]-4-yl)ethyl)hexanamide;
24) 2-amino-N-(2-(4'-(trifluoromethoxy)-[1,1'-biphenyl]-4-yl)ethyl)butanamide;
25) 2-amino-N-(2-(4'-(trifluoromethoxy)-[1,1'-biphenyl]-4-yl)ethyl)pentanamide;
26) 2-amino-N-(2-(4'-(trifluoromethoxy)-[1,1'-biphenyl]-4-yl)ethyl)hexanamide;
27) 2-amino-N-(2-(3',4'-difluoro-[1,1'-biphenyl]-4-yl)ethyl)pentanamide;
28) N-(2-(3',4'-dichloro-[1,1'-biphenyl]-4-yl)ethyl)-2-(methylamino)butanamide;
29) N-(2-(3',4'-dichloro-[1,1'-biphenyl]-4-yl)ethyl)-2-(methylamino)pentanamide;
30) N-(2-(3',4'-dichloro-[1,1'-biphenyl]-4-yl)ethyl)-2-(methylamino)hexanamide;
31) 2-(methylamino)-N-(2-(4'-(trifluoromethyl)-[1,1'-biphenyl]-4-yl)ethyl)butanamide;
32) 2-(methylamino)-N-(2-(4'-(trifluoromethyl)-[1,1'-biphenyl]-4-yl)ethyl)pentanamide;
33) 2-(methylamino)-N-(2-(4'-(trifluoromethyl)-[1,1'-biphenyl]-4-yl)ethyl)hexanamide;
34) 2-(methylamino)-N-(2-(4'-(trifluoromethoxy)-[1,1'-biphenyl]-4-yl)ethyl)butanamide;
35) 2-(methylamino)-N-(2-(4'-(trifluoromethoxy)-[1,1'-biphenyl]-4-yl)ethyl)pentanamide;
36) 2-(methylamino)-N-(2-(4'-(trifluoromethoxy)-[1,1'-biphenyl]-4-yl)ethyl)hexanamide; and
37) N-(2-(3',4'-dichloro-[1,1'-biphenyl]-4-yl)ethyl)-2-(dimethylamino)pentanamide.

The compound of the present invention may be in the form of a pharmaceutically acceptable salt. As a salt, an acid addition salt formed by a pharmaceutically acceptable free acid may be used. As used herein, the term "pharmaceutically acceptable salt" refers to an organic or inorganic addition salt of the compound represented by Formula 1 that is tolerated and sufficiently non-toxic to be used for patients at any concentration exhibiting pharmacological effects of the compound.

The acid addition salt is prepared by typical methods, for example, dissolving the compound in an excess aqueous acid solution, and precipitating the obtained salt using a water-miscible organic solvent, for example, methanol, ethanol, acetone or acetonitrile. The same molar amount of compound and acid or alcohol (for example, glycol monomethyl ether) in water are heated, and then the resulting mixture may be evaporated and dried, or the precipitated salt may be suction filtered.

In this case, as the free acid, organic acids and inorganic acids may be used. Further, as the inorganic acids, hydrochloric acid, phosphoric acid, sulfuric acid, nitric acid, tartaric acid, and the like may be used, and as the organic acids, methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, and the like may be used, but the free acid is not limited thereto.

Further, a pharmaceutically acceptable metal salt may be prepared using a base. An alkali metal salt or an alkaline earth metal salt is obtained, for example, by dissolving the compound in an excessive amount of an alkali metal hydroxide or alkaline earth metal hydroxide solution, filtering a non-dissolved compound salt, and then evaporating and drying a filtrate. In this case, as the metal salt, it is pharmaceutically preferable to prepare particularly, sodium, potassium, or calcium salts, but the metal salt is not limited thereto. In addition, a silver salt corresponding thereto may be obtained by reacting an alkali metal or alkaline earth metal salt with a suitable silver salt (for example, silver nitrate).

The pharmaceutically acceptable salt of the compound of the present invention includes a salt of an acidic or basic group that may be present in the compound of Formula 1, unless otherwise indicated. For example, the pharmaceutically acceptable salt may comprise sodium, calcium, potassium salts and the like of a hydroxyl group. The examples of other pharmaceutically acceptable salts of an amino group include hydrobromide, sulfate, hydrogen sulfate, phosphate, hydrogen phosphate, dihydrogen phosphate, acetate, succinate, citrate, tartrate, lactate, mandelate, methanesulfonate (mesylate), p-toluenesulfonate (tosylate) salts, and the like, and may be prepared by a salt preparation method known in the art.

The salt of the compound of Formula 1 of the present invention is a pharmaceutically acceptable salt, and any salt is available without limitation as long as the salt shows a pharmacological activity equivalent to that of the compound of Formula 1. For example, a salt of the compound of Formula 1 presents antifungal activity.

As another aspect, the present invention provides a method for preparing a derivative compound, a stereoisomer thereof, or a pharmaceutically acceptable salt thereof in which a biphenyl group is introduced into the aminoalkanoic acid, the method including a first step of forming a peptide bond by reacting an aminoalkanoic acid derivative compound protected by a butoxycarbonyl (Boc) protecting group, which is represented by the following Formula 2, with a biphenyl derivative compound including a primary amine group, which is represented by the following Formula 3; and a second step of removing the Boc protecting group by reacting the compound obtained in the first step with an acid:

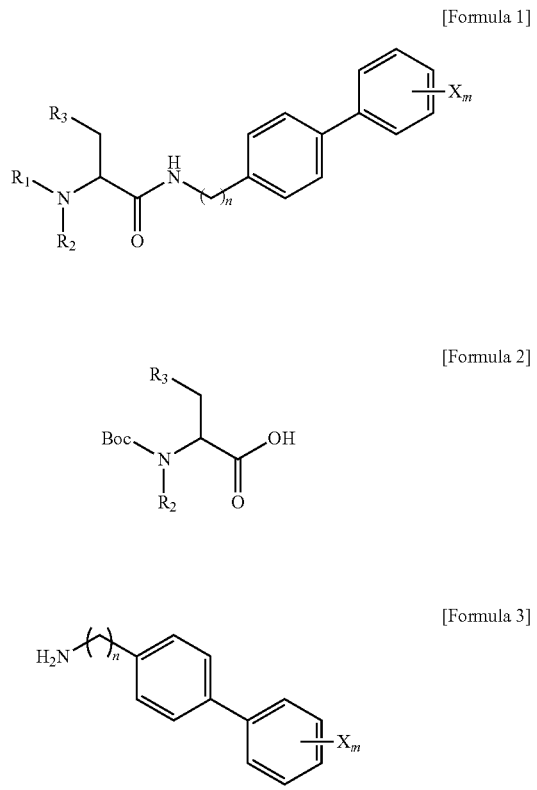

[Formula 1]

[Formula 2]

[Formula 3]

in Formula 1, n is 0, 1, 2, 3, 4 or 5, $R_1$, $R_2$, and $R_3$ are each independently the same as or different from each other, and are each independently selected from the group consisting of hydrogen, a $C_{1-7}$ alkyl, hydroxyl, a halogen, a halogenated $C_{1-7}$ alkyl, a $C_{1-7}$ alkyloxy and a halogenated $C_{1-7}$ alkyloxy, and X is m substituents (m is an integer from 1 to 5) which are the same as or different from each other, selected from the group consisting of a halogen group, a halogenated $C_{1-7}$ alkyl group and a halogenated $C_{1-7}$ alkoxy group.

In the preparation method of the present invention, the aminoalkanoic acid derivative compound protected by the Boc protecting group, which is represented by Formula 2 may be prepared by reacting an amino acid derivative represented by the following Formula 4 with di-tert-butyl dicarbonate (also known as Boc anhydride):

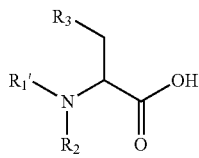

[Formula 4]

in the said Formula 4, $R_1'$, $R_2$, and $R_3$ are each independently the same as or different from each other, and are each independently selected from the group consisting of hydrogen, a $C_{1-7}$ alkyl, hydroxyl, a halogen, a halogenated $C_{1-7}$ alkyl, a $C_{1-7}$ alkyloxy and a halogenated $C_{1-7}$ alkyloxy.

In this case, when $R_2$ of the finally prepared compound is an alkyl, a step of alkylating the compound by reacting the compound with a haloalkane in the presence of a base after the above reaction may be further performed. For example, the alkylation may be carried out by dissolving the compound represented by Formula 4 and a haloalkane compound corresponding 5 to 20 equivalents of the compound, for example, alkane iodide in an organic solvent, for example, tetrahydrofuran, adding sodium hydride as a base at a low temperature, for example, 0° C. and then reacting the reactants at 15 to 30° C. for 12 to 48 hours, but not limited thereto. An alkylation reaction of amines known in the art may be used without limitation or performed by being modified.

Meanwhile, in the preparation method of the present invention, a biphenyl derivative compound containing a primary amine group, which is represented by Formula 3 may be prepared by reacting a $C_{0-2}$ alkylamine derivative in which a halophenyl group at one end is substituted, which is represented by the following Formula 5 with di-tert-butyl dicarbonate to introduce a Boc protecting group into an amine group, reacting the resulting alkylamine derivative with a phenylboronic acid derivative represented by the following Formula 6, and then reacting the reactants with an acid to remove the Boc protecting group:

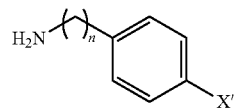

[Formula 5]

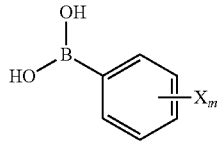

[Formula 6]

in the said formulae,

X' is a halogen, and

X is m substituents (m is an integer from 1 to 5) which are the same as or different from each other, selected from the group consisting of a halogen group, a halogenated $C_{1-7}$ alkyl group and a halogenated $C_{1-7}$ alkoxy group.

In this case, the reaction with the phenylboronic acid derivative may be achieved by a cross-coupling reaction using a metal catalyst in the presence of a base. For example, the reaction may be performed under basic conditions by a metal catalyst such as palladium or nickel. The metal catalyst may be a catalyst in which a phosphine ligand is bound to a metal. For example, the reaction may be a Suzuki-Miyaura cross-coupling reaction performed by Pd(PPh$_3$)$_4$ in the presence of Na$_2$CO$_3$, but is not limited thereto.

For example, in the preparation method of the present invention, the first step may be achieved by an anhydride coupling reaction performed in an organic solvent in the presence of N-methylmorpholine (NMM) or isobutyl chloroformate (IBCF). As the organic solvent, tetrahydrofuran may be used, but the organic solvent is not limited thereto.

For example, in the preparation method of the present invention, the second step to remove the Boc protecting group may be performed by carrying out a reaction with hydrochloric acid, but is not limited thereto.

Furthermore, the preparation method of the present invention may further include a third step of forming a secondary amine by alkylating amine after the second step when each of R$_1$ and R$_2$ of the compound finally prepared is an alkyl. The amination may be performed by reacting with formaldehyde while supplying hydrogen gas in the presence of Pd/C as a reducing agent. For example, the reaction may be performed at 15 to 30° C. for 6 to 24 hours, but is not limited thereto, and the alkylation reaction of amines known in the art may be used without limitation or performed by being modified.

As still another aspect, the present invention provides an antifungal composition comprising, as an active ingredient, a derivative compound in which a biphenyl group is introduced into an aminoalkanoic acid, and a stereoisomer thereof, or a pharmaceutically acceptable salt thereof.

As yet another aspect, the present invention provides a pharmaceutical composition for treating or preventing a fungal infectious disease, wherein the composition comprises, as an active ingredient, an aminoalkanoic acid derivative into which a biphenyl group is introduced, a stereoisomer thereof, or a pharmaceutically acceptable salt thereof.

For example, the novel aminoalkanoic acid derivative into which a biphenyl group is introduced, a stereoisomer thereof, or a pharmaceutically acceptable salt thereof of the present invention may exhibit antifungal activity against opportunistic infectious fungi, and thus may be used as an antifungal composition, and furthermore, may be used for preventing or treating a fungal infectious disease.

As used herein, the term "prevention" refers to any actions that suppress, inhibit or delay the onset, development or recurrence of any concerned disease by administering the said pharmaceutical composition. The term "treatment" refers to any actions in which the symptoms of any concerned disease are alleviated or beneficially improved by administering the said pharmaceutical composition.

For example, a fungal infectious disease that can be prevented or treated by the pharmaceutical composition of the present invention may include, for example, infectious diseases caused by *Cryptococcus neoformans, Candida albicans, Candida auris, Candida glabrata*, and *Aspergillus fumigatus*. The fungal infectious disease may be encephalomeningitis caused by Cryptococcus, but not limited thereto.

The pharmaceutical composition according to the present invention may comprise, as an active ingredient, a compound represented by Formula 1, a stereoisomer thereof, or a pharmaceutically acceptable salt thereof, and may also further include a pharmaceutically acceptable carrier, diluent or excipient. For example, the pharmaceutical composition according to the present invention may be formulated and used in various forms such as an oral dosage form such as a powder, granules, a tablet, a capsule, a suspension, an emulsion, a syrup, or an aerosol, or an injection of a sterile injection solution by a conventional method according to each intended use, and may be administered orally or through various routes including intravenous, intraperitoneal, subcutaneous, rectal, topical administration and the like. Examples of a suitable carrier, diluent, or excipient that may be included in such a composition include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, mineral oil, and the like. Further, the composition of the present invention may further include a filler, an anticoagulant, a lubricant, a wetting agent, a fragrance, an emulsifying agent, a preservative, and the like.

A solid preparation for oral administration includes a tablet, a pill, a powder, granules, a capsule, and the like, and the solid preparation is formulated by mixing at least one excipient, for example, starch, calcium carbonate, sucrose, lactose, gelatin, and the like with the composition. Further, in addition to a simple excipient, a lubricant such as magnesium stearate and talc may be used.

As a liquid preparation for oral administration, a suspension, a liquid for internal use, an emulsion, a syrup or the like may be used, and in addition to water and liquid paraffin, which are simple commonly used diluents, various excipients, for example, a wetting agent, a sweetener, a flavoring agent, a preserving agent or the like may be employed.

Examples of a preparation for parenteral administration include an aqueous sterile solution, a non-aqueous solvent, a suspension, an emulsion, a freeze-dried preparation, and a suppository. As the non-aqueous solvent and the suspension, it is possible to use propylene glycol, polyethylene glycol, a vegetable oil such as olive oil, an injectable ester such as ethyl oleate, and the like. As a base of the suppository, it is possible to use Witepsol®, Macrogol, Tween 61, cacao butter, laurin fat, glycerogelatin, and the like. Meanwhile, the injection may include additives in the related art, such as a solubilizer, an isotonic agent, a suspending agent, an emulsifier, a stabilizer, and a preservative.

The composition of the present invention is administered in a pharmaceutically effective amount. The term "pharmaceutically effective amount" as used herein refers to an amount that is sufficient enough to treat diseases at a reasonable benefit/risk ratio applicable to medical treatment and does not cause side effects, and an effective dosage level may be determined according to various factors including patient's health status, type of diseases, severity of disease, activity of drugs, sensitivity to drugs, administration method, administration time, administration route and excretion rate, duration of treatment, and drugs used in combination or simultaneously, and other factors well known in the medical field. The composition of the present invention may be administered as an individual therapeutic agent or in combination with other therapeutic agents, may be administered sequentially or simultaneously with certain conventional therapeutic agents, and may be administered in a single dose or multiple doses. It is important to administer the composition in a minimum amount that can obtain the maximum effects without any side effects, in consideration of all the aforementioned factors, and this amount may be easily determined by those skilled in the art.

For example, since the amount may be increased or decreased depending on the administration route, the severity of disease, gender, body weight, age, and the like, the dosage is not intended to limit the scope of the present invention in any way.

Furthermore, the present invention provides a method for treating a fungal infectious disease, the method including administering the pharmaceutical composition to an individual in need thereof.

As used herein, the term "individual" refers to animals including a monkey, a cow, a horse, a sheep, a pig, a chicken, a turkey, a quail, a cat, a dog, a mouse, a rat, a rabbit, or a guinea pig, including a human who developed a fungal infectious disease or is likely to develop the fungal infectious disease, and the disease may be effectively prevented or treated by administering the pharmaceutical composition of the present invention to an individual. Further, the pharmaceutical composition of the present invention exhibits a therapeutic effect on a disease induced by a fungal infection due to the antifungal activity thereof, and thus may exhibit a synergistic effect when administered in combination with an existing therapeutic agent.

As used herein, the term "administration" refers to provision of a predetermined material to a patient by any appropriate method. With regard to the route of administration of the composition of the present invention, the composition of the present invention may be administered via any general route, which may reach a target tissue. The route of administration may be intraperitoneal administration, intravenous administration, intramuscular administration, subcutaneous administration, intradermal administration, oral administration, topical administration, intranasal administration, intrapulmonary administration, and rectal administration, but is not limited thereto. In addition, the pharmaceutical composition of the present invention may also be administered by any device which may allow an active material or ingredient to move to a target cell. Preferred administration modes and preparations are intravenous injection, subcutaneous injection, intradermal injection, intramuscular injection, drip injection and the like. An injectable preparation may be prepared using an aqueous solvent such as physiological saline and Ringer's solution, a non-aqueous solvent such as a vegetable oil, a higher fatty acid ester (for example, ethyl oleate, and the like), and an alcohol (for example, ethanol, benzyl alcohol, propylene glycol, glycerin, and the like), and may include a pharmaceutical carrier such as a stabilizer for preventing spoilage (for example, ascorbic acid, sodium bisulfite, sodium pyrosulfite, BHA, tocopherol, EDTA, and the like), an emulsifier, a buffer for pH control, and a preservative for inhibiting microbial growth (for example, phenylmercuric nitrate, thimerosal, benzalkonium chloride, phenol, cresol, benzyl alcohol, and the like).

The term "therapeutically effective amount" used in combination with the active ingredient in the present invention refers to an amount of a aminoalkanoic acid derivative compound in which a biphenyl group is introduced into aminoalkanoic acid, which is effective for preventing or treating a target disease, a stereoisomer thereof, or a pharmaceutically acceptable salt thereof.

According to various exemplary embodiments of the present invention, the disadvantages of conventional drugs used as antifungal agents can be overcome through a compound using an aminoalkanoic acid containing a biphenyl group, for example, alpha-aminobutyric acid or norvaline or norleucine as a basic skeleton. In particular, the present invention can provide antifungal agents having improved safety and efficacy to alleviate or eliminate the side effects of the conventional antifungals and to enhance therapeutic effects. Therefore, the present invention can provide a pharmaceutical composition to treat and/or prevent various fungal infectious diseases. Further, the compound of the present invention can be used to prepare an antibacterial composition against gram-positive, gram-negative, and MRSA-resistant bacteria. In addition, the compound of the present invention can be used for the development of an anti-inflammatory therapeutic agent.

DETAILED DESCRIPTION

Figure 1:
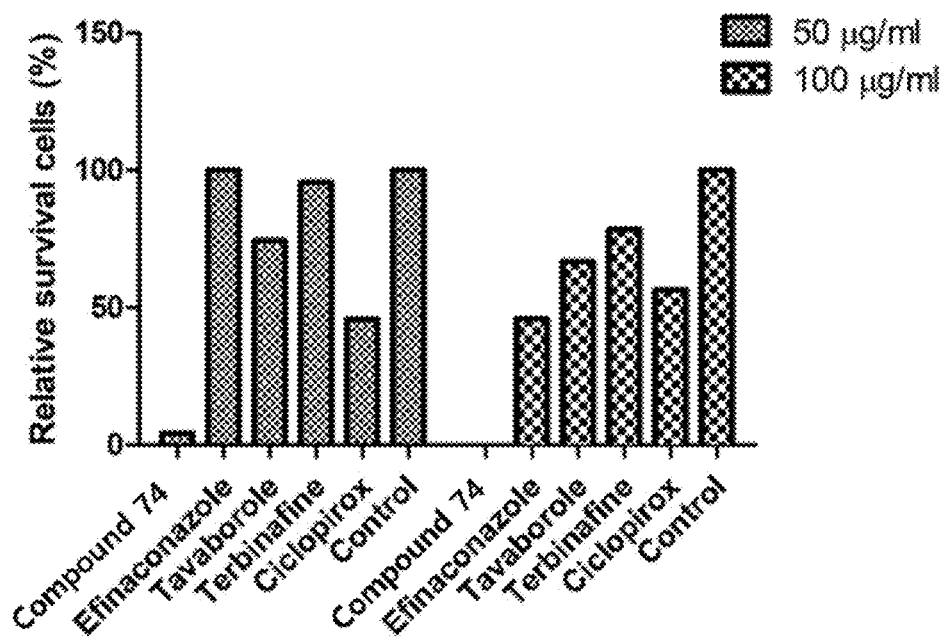
FIG. 1 compares the antifungal activity of Compound 74 of the present invention with those of commercially available comparative drugs.

Hereinafter, the present invention will be described in more detail with reference to the following Preparation Examples and Examples. However, the following Preparation Examples and Examples are only for exemplifying the present invention, and the scope of the present invention is not limited thereto.

First, reactions used in the synthesis of the compound of the present invention were generalized and summarized as follows.

Reaction Scheme a - Introduction of Boc protecting group

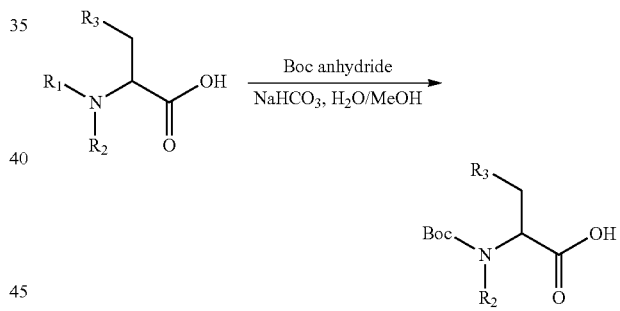

Norleucine (1.0 eq), Boc anhydride (1.5 eq), and sodium bicarbonate (1.5 eq) were dissolved in a 1:1 mixed solvent of distilled water and methanol and reacted at room temperature for 36 to 48 hours. After the mixture was concentrated in a vacuum state, the pH of an aqueous layer was adjusted to 2 with 1.0 M hydrochloric acid. Then, the moisture of an organic layer obtained by extraction with ethyl acetate was removed with sodium sulfate, and the solvent was evaporated in vacuum to obtain the title compound.

Reaction Scheme b - Methylation of amine group

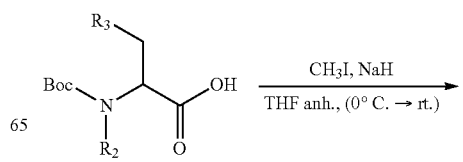

-continued

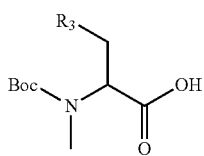

The compound (1.0 eq) obtained from Reaction Scheme a and iodomethane (10 eq) were dissolved in a tetrahydrofuran solvent, and sodium hydride (10 eq) was very slowly added dropwise thereto at 0° C. The reactants were reacted at room temperature for 24 hours. After the reaction was completed, the resulting product was diluted with an ether solvent, and distilled water was added thereto. The pH of an aqueous layer was adjusted to 2 with a 20% citric acid solution. Then, the moisture of an organic layer obtained by extraction with ethyl acetate was removed with sodium sulfate, and the solvent was evaporated in vacuum. The obtained residue was separated and purified by chromatography using silica gel to obtain the title compound.

Reaction Scheme C - Introduction of Boc protecting group on primary amine group

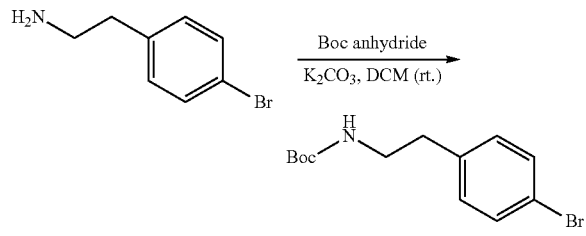

After 4-bromophenetylamine (1.0 eq) was dissolved in a methylene chloride solvent, potassium carbonate (1.5 eq) and Boc anhydride (1.05 eq) were added thereto, and the resulting mixture was reacted at room temperature for about 12 to 18 hours. The reaction mixture was diluted with methylene chloride and washed twice with distilled water. The organic layer was dried with sodium sulfate and then concentrated in vacuum. The obtained residue was washed with hexane and then evaporated in a vacuum state to obtain the title compound.

Reaction Scheme d - Synthesis of biphenylamine hydrochloride derivative

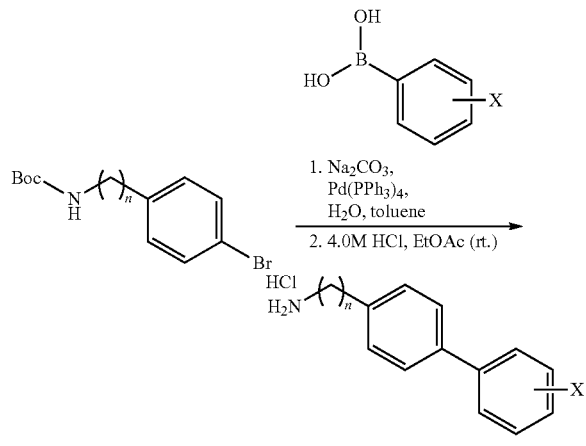

The compound obtained from Reaction Scheme c, tert-butyl (4-bromobenzyl)carbamate or tert-butyl (4-bromophenyl)carbamate (1.0 eq), benzene boronic acid (1.5 eq), sodium carbonate (5.0 eq), and tetrakis(triphenylphosphine) palladium (0.04 eq) were dissolved in a 2:1 to 2.5:1 mixed solvent of degassed toluene and distilled water, and reacted under reflux at a temperature of 140° C. for 12 to 18 hours. After the reaction, the catalyst was removed by filtration through Celite, and the solvent was evaporated from the filtered organic layer in a vacuum state. The obtained residue was separated and purified by chromatography using silica gel. After the purified product was dissolved in an ethyl acetate solvent, the resulting solution was stirred at room temperature while adding 4.0 M hydrochloric acid (6.0 to 10.0 eq) thereto. The obtained white solid in the form of a salt was washed with ethyl acetate, and then completely dried in a vacuum state to obtain the title compound.

Reaction Scheme e - Mixed anhydride coupling (MAC) reaction

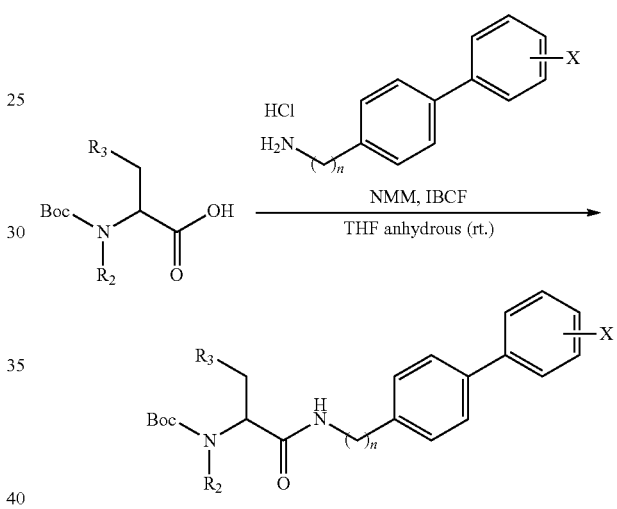

The compound synthesized according to Reaction Scheme a or the compound synthesized according to Reaction Scheme b (1.0 eq), and N-methylmorpholine (NMM, 2.5 to 2.8 eq) were put into a distilled tetrahydrofuran solvent and the resulting mixture was stirred for 15 minutes. Then isobutyl chloroformate (IBCF, 1.3 eq) was added thereto, and the resulting mixture was further stirred for 15 minutes, and then the compound (1.05 eq) obtained from Reaction Scheme d was added thereto. The reaction mixture was allowed to react at room temperature for about 3 to 5 hours. The mixture was filtered to evaporate the solvent in a vacuum state. The obtained residue was separated and purified by chromatography using silica gel to obtain the title compound.

Reaction Scheme f - Removal of Boc protecting group

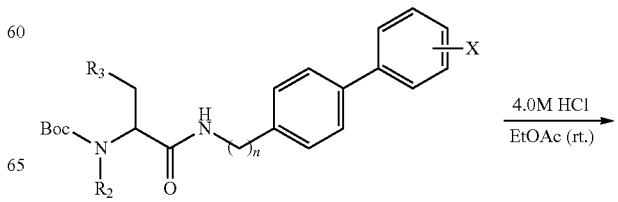

-continued

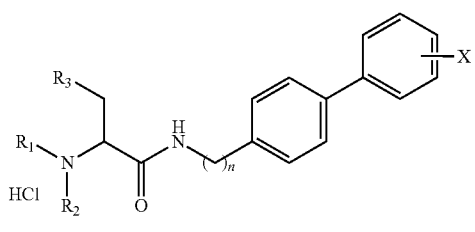

After the compound derivative (1.0 eq) obtained from Reaction Scheme e was dissolved in an ethyl acetate solvent, the resulting solution was stirred at room temperature while adding 4.0 M hydrochloric acid (6.0 to 10.0 eq) thereto. The obtained white solid in the form of a salt was washed with ethyl acetate, and then completely dried in a vacuum state to obtain the title compound.

Reaction Scheme g - Dimethylation of amine group

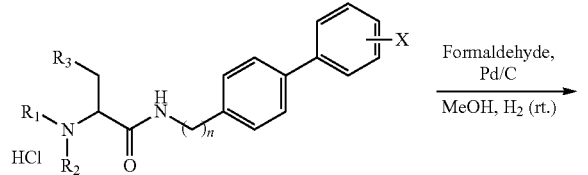

The compound (1.0 eq) obtained from Reaction Scheme f was dissolved in methanol, triethylamine (6.0 eq) was added thereto, and then formaldehyde (37% by weight solution, 1.0 to 2.5 eq) and a 10% palladium catalyst (0.1 to 0.5 eq) were sequentially added thereto. The reactants were reacted at room temperature for 18 hours. After the reaction, the catalyst was removed by filtration through Celite, and the filtered organic layer was evaporated in a vacuum state to obtain a white solid. The resulting product was recrystallized with methanol and diethyl ether to obtain the title compound.

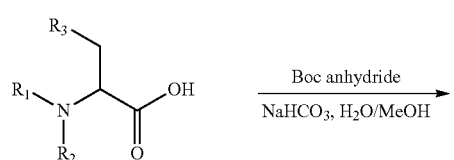

1; $R_1 = H$ $R_2 = H$ $R_3 = CH_3$
2; $R_1 = H$ $R_2 = H$ $R_3 = CH_2CH_3$
3; $R_1 = H$ $R_2 = H$ $R_3 = CH_2CH_2CH_3$

-continued

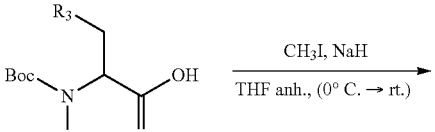

4; $R_2 = H$ $R_3 = CH_3$
5; $R_2 = H$ $R_3 = CH_2CH_3$
6; $R_2 = H$ $R_3 = CH_2CH_2CH_3$

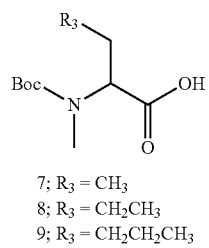

7; $R_3 = CH_3$
8; $R_3 = CH_2CH_3$
9; $R_3 = CH_2CH_2CH_3$

Preparation Examples for synthesizing the compound of the present invention are as follows.

Preparation Examples

Preparation Example 1: Preparation of (R)/(S)-2-((tert-butoxycarbonyl)amino)butanoic acid (4)

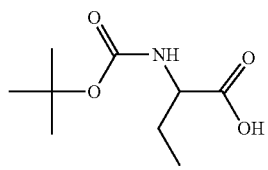

Compound 1 (2-aminobutanoic acid, 5.00 g, 48.5 mmol), Boc anhydride (19.9 mL, 72.7 mmol), and $NaHCO_3$ (6.11 g, 72.7 mmol) were reacted using Reaction Scheme a to synthesize Compound 4, (R)/(S)-2-((tert-butoxycarbonyl)amino)butanoic acid (8.25 g, 83%) in the form of a white powder.

$R_f$=0.00 (DCM 9.5: Methanol 0.5 and few drops of acetic acid);

$^1$H NMR (DMSO-$d_6$, 300 MHz) 12.40 (C(O)OH), 7.02 (d, J=7.9 Hz, Boc-NH), 3.69-3.82 (m, Chiral-H), 1.48-1.72 (m, $CH_2CH_3$), 1.38 (s, Boc), 0.87 (t, J=7.3 Hz, $CH_2CH_3$).

Preparation Example 2: Preparation of (R)/(S)-2-((tert-butoxycarbonyl)amino)pentanoic acid (5)

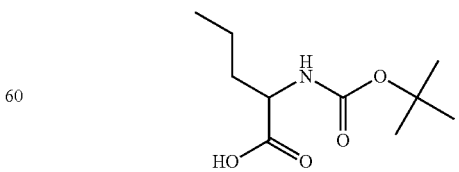

Compound 2 (2-aminopentanoic acid, 10.00 g, 25.6 mmol), Boc anhydride (35.1 mL, 128.0 mmol), and $NaHCO_3$ (10.8 g, 128.0 mmol) were reacted using Reaction Scheme a to synthesize Compound 5, (R)/(S)-2-((tert-butoxycarbonyl)amino)pentanoic acid (13.40 g, 83%) in the form of a white powder.

$R_f$=0.85 (DCM 3: Methanol 17);

$^1$H NMR(DMSO-$d_6$, 400 MHz) 12.40 (C(O)OH), 7.03 (d, J=8.0 Hz, Boc-NH), 3.75-3.89 (m, Chiral-H), 1.50-1.65 (m, $CH_2CH_2CH_3$), 1.20-1.38 (m, $CH_2CH_2CH_3$, Boc), 0.85 (t, J=7.4 Hz, $CH_2CH_2CH_3$).

Preparation Example 3: Preparation of (R)/(S)-2-((tert-butoxycarbonyl)amino)hexanoic acid (6)

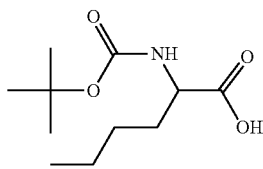

Compound 3 (2-aminohexanoic acid, 5.00 g, 38.1 mmol), Boc anhydride (15.7 mL, 57.2 mmol), and $NaHCO_3$ (4.80 g, 57.2 mmol) were reacted using Reaction Scheme a to synthesize Compound 6, (R)/(S)-2-((tert-butoxycarbonyl)amino)hexanoic acid (7.14 g, 81%) in the form of a white powder.

$R_f$=0.40 (DCM 9: Methanol 1);

$^1$H NMR (CDCl$_3$, 400 MHz) 10.26 (C(O)OH), 5.00 (d, J=7.6 Hz, Boc-NH), 4.32-4.33 (m, Chiral-H), 1.63-1.87 (m, $CH_2CH_2CH_2CH_3$), 1.47 (s, Boc), 1.31-1.38 (m, $CH_2CH_2CH_2CH_3$), 0.93 (t, J=7.0 Hz, $CH_2CH_2CH_2CH_3$).

Preparation Example 4: Preparation of (R)/(S)-2-((tert-butoxycarbonyl)(methyl)amino)butanoic acid (7)

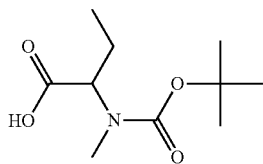

Compound 4 (3.00 g, 14.8 mmol), CH$_3$I (9.2 ml, 147.6 mmol), and NaH (3.54 g, 147.6 mmol) were reacted using Reaction Scheme b to synthesize Compound 7, (R)/(S)-2-((tert-butoxycarbonyl)(methyl)amino)butanoic acid (2.84 g, 88%) in the form of a yellow oil.

$R_f$=0.45 (DCM 9: Methanol 1 and few drops of acetic acid);

$^1$H NMR (DMSO-$d_6$, 300 MHz) 12.7 (C(O)OH), 4.14-4.43 (m, Chiral-H), 2.71 (s, NCH$_3$), 1.50-1.73 (m, $CH_2CH_3$, Boc), 0.79-0.87 (m, $CH_2CH_3$).

Preparation Example 5: Preparation of (R)/(S)-2-((tert-butoxycarbonyl)(methyl)amino)pentanoic acid (8)

Compound 5 (1.50 g, 6.90 mmol), CH$_3$I (4.3 ml, 69.0 mmol), and NaH (1.66 g, 69.0 mmol) were reacted using Reaction Scheme b to synthesize Compound 8, (R)/(S)-2-((tert-butoxycarbonyl)(methyl)amino)pentanoic acid (1.34 g, 83%) in the form of a yellow oil.

$R_f$=0.45 (DCM 9: Methanol 1 and few drops of acetic acid);

$^1$H NMR (DMSO-$d_6$, 300 MHz) 12.7 (C(O)OH), 4.54-4.28 (m, Chiral-H), 2.70 (s, NCH$_3$), 1.79-1.64 (m, $CH_2CH_2CH_3$), 1.41-1.37 (m, $CH_2CH_2CH_3$, Boc), 1.37-1.29 (m, $CH_2CH_2CH_3$).

Preparation Example 6: Preparation of (R)/(S)-2-((tert-butoxycarbonyl)(methyl)amino)hexanoic acid (9)

Compound 6 (3.00 g, 13.0 mmol), CH$_3$I (8.1 ml, 129.7 mmol), and NaH (5.19 g, 129.7 mmol) were reacted using Reaction Scheme b to synthesize Compound 9, (R)/(S)-2-((tert-butoxycarbonyl)(methyl)amino)hexanoic acid (3.18 g, 100%) in the form of a yellow oil.

$R_f$=0.38 (DCM 9: Methanol 1);

$^1$H NMR (CDCl$_3$, 400 MHz) 12.6 (C(O)OH), 4.25-4.52 (m, Chiral-H), 2.70 (s, NCH$_3$), 1.66-1.79 (m, $CH_2CH_2CH_2CH_3$), 1.18-1.40 (m, $CH_2CH_2CH_2CH_3$, Boc), 0.86-0.89 (m, $CH_2CH_2CH_2CH_3$).

Preparation Example 7: Preparation of tert-butyl (4-bromophenethyl)carbamate (12)

4-bromophenethylamine (3.9 ml, 25.1 mmol), K$_2$CO$_3$ (5.21 g, 37.7 mmol), and Boc anhydride (7.2 ml, 26.4 mmol) were reacted using Reaction Scheme c to synthesize Compound 12, tert-butyl(4-bromophenethyl)carbamate (6.23 g, 83%) in the form of a white powder.

$R_f$=0.36 (EtOAc 1: n-hexane 5);

$^1$H NMR (DMSO-$d_6$, 400 MHz) 7.46 (d, J=8.6 Hz, ArH), 7.15 (d, J=8.2 Hz, ArH), 6.87 (s, NH), 3.09-3.14 (m, NHCH$_2$CH$_2$), 2.64-2.67 (m, NHCH$_2$CH$_2$), 1.35 (s, Boc).

Preparation Example 8: Preparation of 3',4'-dichloro-[1,1'-biphenyl]-4-amine hydrochloride (13)

After a compound was obtained by reacting Compound 10 (tert-butyl 4-bromophenylcarbamate, 4.00 g, 14.7 mmol), 3,4-dichlorophenylboronic acid (3.37 g, 17.6 mmol), tetrakis(triphenylphosphine)palladium (0.68 g, 0.59 mmol), and Na$_2$CO$_3$ (7.80 g, 73.5 mmol) using Reaction Scheme d, a Boc group was removed using 4.0 M HCl (7.9 mL, 31.5 mmol in dioxane) to synthesize Compound 13, 3',4'-dichloro-[1,1'-biphenyl]-4-amine hydrochloride (1.27 g, 34%) in the form of a white powder.

$R_f$=0.00 (EtOAc 9: acetone 1);

$^1$H NMR (DMSO-$d_6$, 400 MHz) 9.94 (s, NH$_3$), 7.95 (d, J=2.0 Hz, ArH), 7.40-7.80 (m, ArH), 7.39 (d, J=8.5 Hz, ArH).

Preparation Example 9: Preparation of 4'-(trifluoromethoxy)-[1,1'-biphenyl]-4-amine hydrochloride (14)

After a compound was obtained by reacting Compound 10 (3.99 g, 14.7 mmol), 4-(trifluoromethoxy)phenylboronic acid (7.77 g, 22.0 mmol), tetrakis(triphenylphosphine)palladium (0.68 g, 0.59 mmol), and Na$_2$CO$_3$ (7.77 g, 73.3 mmol) using Reaction Scheme d, a Boc group was removed using 4.0 M HCl (12.8 mL, 51.1 mmol in dioxane) to synthesize Compound 14, 4'-(trifluoromethoxy)-[1,1'-biphenyl]-4-amine hydrochloride (1.99 g, 48%) in the form of a white powder.

$R_f$=0.00 (EtOAc 9: acetone 1);

¹H NMR (DMSO-d$_6$, 400 MHz) 9.45 (bRs, NH$_3$), 7.77 (d, J=8.7 Hz, ArH), 7.71 (d, J=8.4 Hz, ArH), 7.45 (d, J=8.4 Hz, ArH), 7.28 (d, J=8.2 Hz, ArH).

Preparation Example 10: Preparation of 2-(3',4'-dichloro-[1,1'-biphenyl]-4-yl)methan-1-amine hydrochloride (15)

After a compound was obtained by reacting Compound 11 (tert-butyl 4-bromobenzylcarbamate, 6.00 g, 21.0 mmol), 3,4-dichlorophenylboronic acid (4.80 g, 25.2 mmol), tetrakis(triphenylphosphine)palladium (0.97 g, 0.84 mmol), and Na$_2$CO$_3$ (111.1 g, 104.8 mmol) using Reaction Scheme d, a Boc group was removed using 4.0 M HCl (3.1 ml, 12.3 mmol in dioxane) to synthesize Compound 15, 2-(3',4'-dichloro-[1,1'-biphenyl]-4-yl)methan-1-amine hydrochloride (1.08 g, 17%) in the form of a white powder.
R$_f$=0.00 (EtOAc 9: acetone 1);
¹H NMR (DMSO-d$_6$, 400 MHz) 8.71 (s, NH$_3$), 7.97 (s, ArH), 7.63-7.83 (m, ArH), 4.07 (s, NH$_3$CH$_2$).

Preparation Example 11: Preparation of (4'-(trifluoromethyl)-[1,1'-biphenyl]-4-yl)methanamine hydrochloride (16)

After a compound was obtained by reacting Compound 11 (6.00 g, 21.0 mmol), 4-(trifluoromethyl)phenylboronic acid (5.97 g, 31.5 mmol), tetrakis(triphenylphosphine)palladium (0.97 g, 0.84 mmol), and Na$_2$CO$_3$ (11.1 g, 104.8 mmol) using Reaction Scheme d, a Boc group was removed using 4.0 M HCl (17.9 ml, 71.7 mmol in dioxane) to synthesize Compound 16, (4'-(trifluoromethyl)-[1,1'-biphenyl]-4-yl)methanamine hydrochloride (1.08 g, 66%) in the form of a white powder.
R$_f$=0.00 (EtOAc 9: acetone 1);
¹H NMR (DMSO-d$_6$, 400 MHz) 8.49 (s, NH$_3$), 7.93 (d, J=8.2 Hz, ArH), 7.83 (t, J=9.0 Hz, ArH), 7.64 (d, J=8.2 Hz, ArH), 4.09 (s, NH$_3$CH$_2$).

Preparation Example 12: Preparation of (4'-(trifluoromethoxy)-[1,1'-biphenyl]-4-yl)methanamine hydrochloride (17)

After a compound was obtained by reacting Compound 11 (4.00 g, 14.0 mmol), 4-(trifluoromethoxy)phenylboronic acid (4.32 g, 21.0 mmol), tetrakis(triphenylphosphine)palladium (0.65 g, 0.56 mmol), and Na$_2$CO$_3$ (7.41 g, 69.9 mmol) using Reaction Scheme d, a Boc group was removed using 4.0 M HCl (13.9 ml, 55.6 mmol in dioxane) to synthesize Compound 17, (4'-(trifluoromethoxy)-[1,1'-biphenyl]-4-yl)methanamine hydrochloride (2.73 g, 65%) in the form of a white powder.
R$_f$=0.00 (EtOAc 9: acetone 1);
¹H NMR (DMSO-d$_6$, 400 MHz) 8.33 (s, NH$_3$), 7.81-7.83 (m, ArH), 7.75 (d, J=8.2 Hz, ArH), 7.59 (d, J=8.2 Hz, ArH), 7.48 (d, J=8.3 Hz, ArH), 4.08 (s, NH$_3$CH$_2$).

Preparation Example 13: Preparation of 2-(3',4'-dichloro-[1,1'-biphenyl]-4-yl)ethan-1-amine hydrochloride (18)

After a compound was obtained by reacting Compound 12 (tert-butyl (4-bromophenethyl)carbamate, 1.00 g, 3.33 mmol), 3,4-dichlorophenylboronic acid (0.76 g, 4.00 mmol), tetrakis(triphenylphosphine)palladium (0.15 g, 0.15 mmol), and Na$_2$CO$_3$ (1.77 g, 16.7 mmol) using Reaction Scheme d, a Boc group was removed using 4.0 M HCl (2.50 ml, 10.0 mmol in dioxane) to synthesize Compound 18, 2-(3',4'-dichloro-[1,1'-biphenyl]-4-yl)ethan-1-amine hydrochloride (2.73 g, 65%) in the form of a white powder.
R$_f$=0.00 (EtOAc 9: acetone 1);
¹H NMR (DMSO-d$_6$, 400 MHz) 8.33 (s, NH$_3$), 7.93 (d, J=1.9 Hz, ArH), 7.66-7.72 (m, ArH), 7.39 (d, J=8.2 Hz, ArH), 2.98-3.07 (m, NH$_3$CH$_2$CH$_2$).

Preparation Example 14: Preparation of 2-(4'-(trifluoromethyl)-[1,1'-biphenyl]-4-yl)ethan-1-amine hydrochloride (19)

After a compound was obtained by reacting Compound 12 (0.50 g, 1.67 mmol), 4-(trifluoromethyl)phenylboronic acid (0.38 g, 2.00 mmol), tetrakis(triphenylphosphine)palladium (0.08 g, 0.07 mmol), and Na$_2$CO$_3$ (0.88 g, 8.33 mmol) using Reaction Scheme d, a Boc group was removed using 4.0 M HCl (1.25 ml, 5.00 mmol in dioxane) to synthesize Compound 19, 2-(4'-(trifluoromethyl)-[1,1'-biphenyl]-4-yl)ethan-1-amine hydrochloride (0.28 g, 56%) in the form of a white powder.
R$_f$=0.00 (EtOAc 9: acetone 1);
¹H NMR (DMSO-d$_6$, 400 MHz) 8.37 (s, NH$_3$), 7.71-7.91 (m, ArH), 7.44 (d, J=8.1 Hz, ArH), 3.01-3.11 (m, NH$_3$CH$_2$CH$_2$).

Preparation Example 15: Preparation of 2-(4'-(trifluoromethoxy)-[1,1'-biphenyl]-4-yl)ethan-1-amine hydrochloride (20)

After a compound was obtained by reacting Compound 12 (1.50 g, 5.00 mmol), 4-(trifluoromethoxy)phenylboronic acid (1.23 g, 6.00 mmol), tetrakis(triphenylphosphine)palladium (0.23 g, 0.20 mmol), and Na$_2$CO$_3$ (2.65 g, 25.0 mmol) using Reaction Scheme d, a Boc group was removed using 4.0 M HCl (3.75 ml, 15.0 mmol in dioxane) to synthesize Compound 20, 2-(4'-(trifluoromethoxy)-[1,1'-biphenyl]-4-yl)ethan-1-amine hydrochloride (0.88 g, 55%) in the form of a white powder.
R$_f$=0.00 (EtOAc 9: acetone 1);
¹H NMR (DMSO-d$_6$, 400 MHz) 8.31 (s, NH$_3$), 7.79 (d, J=8.7 Hz, ArH), 7.66 (d, J=8.1 Hz, ArH), 7.45 (d, J=8.2 Hz, ArH), 7.40 (d, J=8.1 Hz, ArH), 2.97-3.10 (m, NH$_3$CH$_2$CH$_2$).

Preparation Example 16: Preparation of 2-(3',4'-difluoro-[1,1'-biphenyl]-4-yl)ethan-1-amine hydrochloride (21)

After a compound was obtained by reacting Compound 12 (1.00 g, 3.33 mmol), 3,4-dichlorophenylboronic acid (0.76 g, 4.00 mmol), tetrakis(triphenylphosphine)palladium (0.15 g, 0.15 mmol), and Na$_2$CO$_3$ (1.77 g, 16.7 mmol) using Reaction Scheme d, a Boc group was removed using 4.0 M HCl (2.50 ml, 10.0 mmol in dioxane) to synthesize Compound 21, 2-(3',4'-difluoro-[1,1'-biphenyl]-4-yl)ethan-1-amine hydrochloride (2.73 g, 65%) in the form of a white powder.
R$_f$=0.00 (EtOAc 9: acetone 1);
¹H NMR (DMSO-d$_6$, 400 MHz) 7.95 (s, NH$_3$), 7.74-7.79 (m, ArH), 7.67 (d, J=8.1 Hz, ArH), 7.48-7.54 (m, ArH), 7.37 (d, J=8.1 Hz, ArH), 2.90-3.09 (m, NH$_3$CH$_2$CH$_2$).

Preparation Example 17: Preparation of (R)/(S)-tert-butyl(1-((3',4'-dichloro-[1,1'-biphenyl]-4-yl)amino)-1-oxobutan-2-yl)carbamate (22)

Compound 4 (0.63 g, 3.12 mmol), NMM (0.96 ml, 8.74 mmol), IBCF (0.53 ml, 4.06 mmol), and Compound 13 (0.90 g, 3.28 mmol) were reacted using Reaction Scheme e to synthesize Compound 22, (R)/(S)-tert-butyl(1-((3',4'-dichloro-[1,1'-biphenyl]-4-yl)amino)-1-oxobutan-2-yl)carbamate (1.09 g, 82%) in the form of a pale yellow powder.

$R_f$=0.33 (EtOAc 1: n-hexane 3);

$^1$H NMR (CDCl$_3$, 400 MHz) 8.55 (s, C(O)NH), 7.58 (d, J=7.3 Hz, ArH), 7.44-7.47 (m, ArH), 7.34 (dd, J=1.8 Hz, 8.3 Hz, ArH), 5.12 (s, Boc-NH), 4.18 (s, Chiral-H), 1.67-2.05 (m, CH$_2$CH$_3$), 1.47 (s, Boc), 1.03 (t, J=7.4 Hz, CH$_2$CH$_3$).

Preparation Example 18: Preparation of (R)/(S)-tert-butyl(1-((3',4'-dichloro-[1,1'-biphenyl]-4-yl)amino)-1-oxopentan-2-yl)carbamate (23)

Compound 5 (0.30 g, 1.52 mmol), NMM (0.42 ml, 3.80 mmol), IBCF (0.26 ml, 1.98 mmol), and Compound 13 (0.44 g, 1.60 mmol) were reacted using Reaction Scheme e to synthesize Compound 23, (R)/(S)-tert-butyl(1-((3',4'-dichloro-[1,1'-biphenyl]-4-yl)amino)-1-oxopentan-2-yl)carbamate (0.61 g, 92%) in the form of a white powder.

$R_f$=0.37 (EtOAc 1: n-hexane 3);

$^1$H NMR (CDCl$_3$, 400 MHz) 8.53 (s, C(O)NH), 7.62 (d, J=8.6 Hz, ArH), 7.48-7.50 (m, ArH), 7.38 (dd, J=2.0 Hz, 8.3 Hz, ArH), 5.08 (s, Boc-NH), 4.24 (s, Chiral-H), 1.63-1.99 (m, CH$_2$CH$_2$CH$_3$), 1.47-1.50 (m, Boc, CH$_2$CH$_2$CH$_3$), 0.99 (t, J=7.3 Hz, CH$_2$CH$_2$CH$_3$).

Preparation Example 19: Preparation of (R)/(S)-tert-butyl(1-((3',4'-dichloro-[1,1'-biphenyl]-4-yl)amino)-1-oxohexan-2-yl)carbamate (24)

Compound 6 (0.80 g, 3.46 mmol), NMM (0.95 ml, 8.69 mmol), IBCF (0.58 ml, 4.50 mmol), and Compound 13 (1.00 g, 3.64 mmol) were reacted using Reaction Scheme e to synthesize Compound 24, (R)/(S)-tert-butyl(1-((3',4'-dichloro-[1,1'-biphenyl]-4-yl)amino)-1-oxohexan-2-yl)carbamate (1.11 g, 71%) in the form of a white powder.

$R_f$=0.50 (EtOAc 1: n-hexane 3);

$^1$H NMR (DMSO-d$_6$, 400 MHz) 10.10 (s, NH), 7.91 (d, J=1.9 Hz, ArH), 7.64-7.74 (m, ArH), 7.04 (d, J=7.8 Hz, NH), 4.02-4.07 (m, NHCHCH$_2$), 1.57-1.64 (m, CH$_2$CH$_2$CH$_2$CH$_3$), 1.39 (s, Boc), 1.26-1.32 (m, CH$_2$CH$_2$CH$_2$CH$_3$), 0.86 (t, J=6.8 Hz, CH$_2$CH$_2$CH$_2$CH$_3$).

Preparation Example 20: Preparation of (R)/(S)-tert-butyl(1-oxo-1-((4'-(trifluoromethoxy)-[1,1'-biphenyl]-4-yl)amino)pentan-2-yl)carbamate (25)

Compound 5 (0.43 g, 1.97 mmol), NMM (0.61 ml, 5.52 mmol), IBCF (0.33 ml, 2.56 mmol), and Compound 14 (0.60 g, 2.07 mmol) were reacted using Reaction Scheme e to synthesize Compound 25, (R)/(S)-tert-butyl(1-oxo-1-((4'-(trifluoromethoxy)-[1,1'-biphenyl]-4-yl)amino)pentan-2-yl)carbamate (0.66 g, 73%) in the form of a white powder.

$R_f$=0.30 (EtOAc 1: n-hexane 3);

$^1$H NMR (CDCl$_3$, 400 MHz) 8.62 (s, C(O)NH), 7.61 (d, J=7.3 Hz, ArH), 7.54 (d, J=7.6 Hz, ArH), 7.49 (d, J=7.9 Hz, ArH), 7.26-7.29 (m, ArH), 5.19 (d, J=7.4 Hz, Boc-NH), 4.29 (s, Chiral-H), 1.65-1.98 (m, CH$_2$CH$_3$), 1.43-1.56 (m, Boc, CH$_2$CH$_2$CH$_3$), 0.99 (t, J=7.1 Hz, CH$_2$CH$_2$CH$_3$).

Preparation Example 21: Preparation of (R)/(S)-tert-butyl(1-((3',4'-dichloro-[1,1'-biphenyl]-4-yl)amino)-1-oxobutan-2-yl)(methyl)carbamate (26)

Compound 7 (0.68 g, 3.12 mmol), NMM (0.96 ml, 8.74 mmol), IBCF (0.53 ml, 4.06 mmol), and Compound 13 (0.90 g, 3.28 mmol) were reacted using Reaction Scheme e to synthesize Compound 26, (R)/(S)-tert-butyl(1-((3',4'-dichloro-[1,1'-biphenyl]-4-yl)amino)-1-oxobutan-2-yl)(methyl)carbamate (0.74 g, 54%) in the form of an oil.

$R_f$=0.50 (EtOAc 1: n-hexane 3);

$^1$H NMR (CDCl$_3$, 400 MHz) 8.50 (s, C(O)NH), 7.58-7.63 (m, ArH), 7.46-7.50 (m, ArH), 7.38 (dd, J=1.8 Hz, 8.2 Hz, ArH), 4.57 (s, Chiral-H), 2.83 (s, NCH$_3$), 1.71-2.04 (m, CH$_2$CH$_3$), 1.51 (d, J=6.8 Hz, Boc), 0.97 (t, J=7.3 Hz, CH$_2$CH$_3$).

Preparation Example 22: Preparation of (R)/(S)-tert-butyl(1-((3',4'-dichloro-[1,1'-biphenyl]-4-yl)amino)-1-oxopentan-2-yl)(methyl)carbamate (27)

Compound 8 (0.86 g, 3.72 mmol), NMM (1.14 ml, 10.4 mmol), IBCF (0.63 ml, 4.83 mmol), and Compound 13 (1.07 g, 3.90 mmol) were reacted using Reaction Scheme e to synthesize Compound 27, (R)/(S)-tert-butyl(1-((3',4'-dichloro-[1,1'-biphenyl]-4-yl)amino)-1-oxopentan-2-yl)(methyl)carbamate (0.79 g, 47%) in the form of a yellow powder.

$R_f$=0.48 (EtOAc 1: n-hexane 3);

$^1$H NMR (CDCl$_3$, 400 MHz) 8.49 (s, C(O)NH), 7.58-7.64 (m, ArH), 7.47-7.51 (m, ArH), 7.38 (d, J=8.3 Hz, ArH), 4.66 (s, Chiral-H), 2.82 (s, NCH$_3$), 1.67-2.04 (m, CH$_2$CH$_2$CH$_3$), 1.51 (s, Boc), 1.33-1.39 (m, CH$_2$CH$_2$CH$_3$), 0.99 (t, J=7.3 Hz, CH$_2$CH$_2$CH$_3$).

Preparation Example 23: Preparation of (R)/(S)-tert-butyl(1-((3',4'-dichloro-[1,1'-biphenyl]-4-yl)amino)-1-oxohexan-2-yl)(methyl)carbamate (28)

Compound 9 (R)/(S)-2-((tert-butoxycarbonyl)(methyl)amino)hexanoic acid (0.84 g, 3.47 mmol), NMM (1.10 ml, 9.71 mmol), IBCF (0.58 ml, 4.51 mmol), and Compound 13 (1.00 g, 3.64 mmol) were reacted using Reaction Scheme e to synthesize Compound 28, (R)/(S)-tert-butyl(1-((3',4'-dichloro-[1,1'-biphenyl]-4-yl)amino)-1-oxohexan-2-yl)(methyl)carbamate (0.86 g, 53%) in the form of an oil.

$R_f$=0.55 (EtOAc 1: n-hexane 3);

$^1$H NMR (CDCl$_3$, 400 MHz) 8.49 (s, C(O)NH), 7.58-7.64 (m, ArH), 7.47-7.51 (m, ArH), 7.38 (dd, J=2.1 Hz, 8.4 Hz, ArH), 4.64 (s, Chiral-H), 2.82 (s, NCH$_3$), 1.67-2.01 (m, CH$_2$CH$_2$CH$_3$), 1.52 (s, Boc), 1.24-1.44 (m, CH$_2$CH$_2$CH$_3$), 0.93 (t, J=7.1 Hz, CH$_2$CH$_2$CH$_3$).

Preparation Example 24: Preparation of (R)/(S)-2-amino-N-(3',4'-dichloro-[1,1'-biphenyl]-4-yl)butanamide hydrochloride (29)

Compound 22 (1.06 g, 2.50 mmol) and 4.0 M HCl (3.80 ml, 15.0 mmol in dioxane) were reacted using Reaction Scheme f to synthesize Compound 29, (R)/(S)-2-amino-N-(3',4'-dichloro-[1,1'-biphenyl]-4-yl)butanamide hydrochloride (0.87 g, 97%) in the form of a white powder.

$R_f$=0.00 (EtOAc 9: acetone 1);

$^1$H NMR (CDCl$_3$, 400 MHz) 11.05 (s, C(O)NH), 8.38 (s, NH$_3$), 7.93 (d, J=1.9 Hz, ArH), 7.66-7.79 (m, ArH), 4.01-4.04 (m, Chiral-H), 1.86-1.91 (m, CH$_2$CH$_3$), 0.96 (t, J=7.5 Hz, CH$_2$CH$_3$).

Preparation Example 25: Preparation of (R)/(S)-2-amino-N-(3',4'-dichloro-[1,1'-biphenyl]-4-yl)pentanamide hydrochloride (30)

Compound 23 (0.58 g, 1.33 mmol) and 4.0 M HCl (2.00 ml, 7.95 mmol in dioxane) were reacted using Reaction Scheme f to synthesize Compound 30, (R)/(S)-2-amino-N-(3',4'-dichloro-[1,1'-biphenyl]-4-yl)pentanamide hydrochloride (0.40 g, 81%) in the form of a white powder.

$R_f$=0.00 (EtOAc 9: acetone 1);

$^1$H NMR (DMSO-$d_6$, 400 MHz) 11.05 (s, C(O)NH), 8.40 (s, NH$_3$), 7.93 (d, J=1.5 Hz, ArH), 7.66-7.79 (m, ArH), 4.06 (s, Chiral-H), 1.79-1.85 (m, CH$_2$CH$_2$CH$_3$), 1.36-1.43 (m, CH$_2$CH$_2$CH$_3$), 0.91 (t, J=7.3 Hz, CH$_2$CH$_2$CH$_3$).

Preparation Example 26: Preparation of (R)/(S)-2-amino-N-(3',4'-dichloro-[1,1'-biphenyl]-4-yl)hexanamide hydrochloride (31)

Compound 24 (1.10 g, 2.44 mmol) and 4.0 M HCl (3.66 ml, 14.6 mmol in dioxane) were reacted using Reaction Scheme f to synthesize Compound 31, (R)/(S)-2-amino-N-(3',4'-dichloro-[1,1'-biphenyl]-4-yl)hexanamide hydrochloride (0.81 g, 86%) in the form of a white powder.

$R_f$=0.00 (EtOAc 9: acetone 1);

$^1$H NMR (DMSO-$d_6$, 400 MHz) 10.97 (s, C(O)NH), 8.38 (s, NH$_3$), 7.93 (d, J=2.0 Hz, ArH), 7.66-7.78 (m, ArH), 4.03 (s, Chiral-H), 1.81-1.87 (m, CH$_2$CH$_2$CH$_2$CH$_3$), 1.33-1.39 (m, CH$_2$CH$_2$CH$_2$CH$_3$), 0.87 (t, J=6.9 Hz, CH$_2$CH$_2$CH$_2$CH$_3$).

Preparation Example 27: Preparation of (R)/(S)-2-amino-N-(4'-(trifluoromethoxy)-[1,1'-biphenyl]-4-yl)pentanamide hydrochloride (32)

Compound 25 (0.64 g, 1.41 mmol) and 4.0 M HCl (2.12 ml, 8.46 mmol in dioxane) were reacted using Reaction Scheme f to synthesize Compound 32, (R)/(S)-2-amino-N-(4'-(trifluoromethoxy)-[1,1'-biphenyl]-4-yl)pentanamide hydrochloride (0.51 g, 93%) in the form of a white powder.

$R_f$=0.00 (EtOAc 9: acetone 1);

$^1$H NMR (DMSO-$d_6$, 400 MHz) 10.90 (s, C(O)NH), 8.35 (s, NH$_3$), 7.76-7.79 (m, ArH), 7.70 (d, J=8.8 Hz, ArH), 7.45 (d, J=8.2 Hz, ArH), 4.03 (s, Chiral-H), 1.82 (q, J=6.9 Hz, 7.9 Hz, CH$_2$CH$_2$CH$_3$), 1.34-1.47 (m, CH$_2$CH$_2$CH$_3$), 0.92 (t, J=7.3 Hz, CH$_2$CH$_2$CH$_3$).

Preparation Example 28: Preparation of (R)/(S)-N-(3',4'-dichloro-[1,1'-biphenyl]-4-yl)-2-(methylamino)butanamide hydrochloride (33)

Compound 26 (0.69 g, 1.58 mmol) and 4.0 M HCl (2.40 ml, 9.50 mmol in dioxane) were reacted using Reaction Scheme f to synthesize Compound 33, (R)/(S)-N-(3',4'-dichloro-[1,1'-biphenyl]-4-yl)-2-(methylamino)butanamide hydrochloride (0.55 g, 93%) in the form of a white powder.

$R_f$=0.00 (EtOAc 9: acetone 1);

$^1$H NMR (DMSO-$d_6$, 400 MHz) 11.00 (s, C(O)NH), 9.13 (s, NH$_2$), 7.94 (d, J=1.7 Hz, ArH), 7.66-7.78 (m, ArH), 3.96 (t, J=5.5 Hz, Chiral-H), 2.57 (s, NCH$_3$), 1.87-2.05 (m, CH$_2$CH$_3$), 0.94 (t, J=7.5 Hz, CH$_2$CH$_3$).

Preparation Example 29: Preparation of (R)/(S)-N-(3',4'-dichloro-[1,1'-biphenyl]-4-yl)-2-(methylamino)pentanamide hydrochloride (34)

Compound 27 (0.38 g, 0.83 mmol) and 4.0 M HCl (1.25 ml, 4.98 mmol in dioxane) were reacted using Reaction Scheme f to synthesize Compound 34, (R)/(S)-N-(3',4'-dichloro-[1,1'-biphenyl]-4-yl)-2-(methylamino)pentanamide hydrochloride (0.23 g, 71%) in the form of a white powder.

$R_f$=0.00 (EtOAc 9: acetone 1);

$^1$H NMR (DMSO-$d_6$, 400 MHz) 10.98 (s, C(O)NH), 9.09 (s, NH$_2$), 7.94 (s, ArH), 7.66-7.76 (m, ArH), 3.96 (t, J=6.1 Hz, Chiral-H), 2.57 (s, NCH$_3$), 1.80-1.93 (m, CH$_2$CH$_2$CH$_3$), 1.31-1.39 (m, CH$_2$CH$_2$CH$_3$), 0.91 (t, J=7.3 Hz, CH$_2$CH$_2$CH$_3$).

Preparation Example 30: Preparation of (R)/(S)-N-(3',4'-dichloro-[1,1'-biphenyl]-4-yl)-2-(methylamino)hexanamide hydrochloride (35)

Compound 28 (0.82 g, 1.77 mmol) and 4.0 M HCl (2.65 ml, 10.6 mmol in dioxane) were reacted using Reaction Scheme f to synthesize Compound 35, (R)/(S)-N-(3',4'-dichloro-[1,1'-biphenyl]-4-yl)-2-(methylamino)hexanamide hydrochloride (0.60 g, 84%) in the form of a white powder.

$R_f$=0.00 (EtOAc 9: acetone 1);

$^1$H NMR (DMSO-$d_6$, 400 MHz) 10.81 (s, C(O)NH), 9.05 (s, NH$_2$), 7.94 (d, J=2.0 Hz, ArH), 7.66-7.77 (m, ArH), 3.92 (s, Chiral-H), 2.57 (s, NCH$_3$), 1.87-1.99 (m, CH$_2$CH$_2$CH$_3$), 1.29-1.33 (m, CH$_2$CH$_2$CH$_2$CH$_3$), 0.86 (t, J=6.8 Hz, CH$_2$CH$_2$CH$_2$CH$_3$).

Formaldehyde, Pd/C
―――――――――→
MeOH, H$_2$ (rt.)

36; n = 0 R$_3$ = CH$_2$CH$_3$ X = 3',4'-Cl

Preparation Example 31: Preparation of (R)/(S)-N-(3',4'-dichloro-[1,1'-biphenyl]-4-yl)-2-(dimethylamino)pentanamide (36)

Compound 30 (1.0 eq), triethylamine (6.0 eq), formaldehyde (2.0 eq), and a palladium catalyst (0.4 eq) were reacted using Reaction Scheme g to synthesize Compound 36, (R)/(S)-N-(3',4'-dichloro-[1,1'-biphenyl]-4-yl)-2-(dimethylamino)pentanamide.

$^1$H NMR (DMSO-$d_6$, 400 MHz) 10.98 (s, C(O)NH), 7.94 (s, ArH), 7.66-7.76 (m, ArH), 3.96 (t, J=6.1 Hz, Chiral-H), 2.57 (s, N(CH$_3$)$_2$), 1.80-1.93 (m, CH$_2$CH$_2$CH$_3$), 1.31-1.39 (m, CH$_2$CH$_2$CH$_3$), 0.91 (t, J=7.3 Hz, CH$_2$CH$_2$CH$_3$).

HCl
NMM, IBCF  H$_2$N
5, 6, 8 ―――――――――→
THF, anhydrous (rt.)

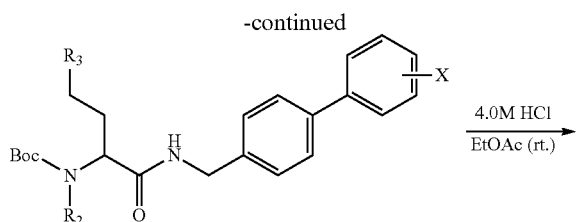

| | | | |
|---|---|---|---|
| 37; | $R_2$ = H | $R_3$ = $CH_3$ | X = 3',4'-Cl |
| 38; | $R_2$ = H | $R_3$ = $CH_2CH_3$ | X = 3',4'-Cl |
| 39; | $R_2$ = H | $R_3$ = $CH_3$ | X = 4-$CF_3$ |
| 40; | $R_2$ = H | $R_3$ = $CH_2CH_3$ | X = 4-$CF_3$ |
| 41; | $R_2$ = H | $R_3$ = $CH_3$ | X = 4-$OCF_3$ |
| 42; | $R_2$ = H | $R_3$ = $CH_2CH_3$ | X = 4-$OCF_3$ |
| 43; | $R_2$ = $CH_3$ | $R_3$ = $CH_3$ | X = 3',4'-Cl |
| 44; | $R_2$ = $CH_3$ | $R_3$ = $CH_3$ | X = 4-$CF_3$ |

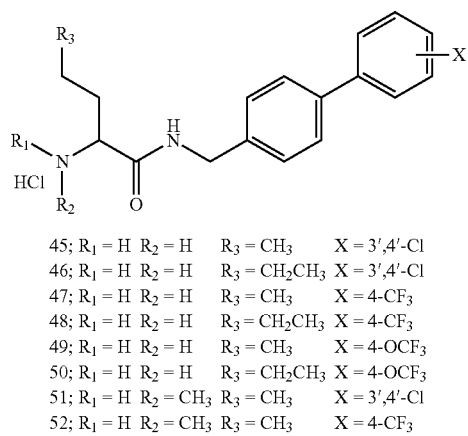

| | | | | |
|---|---|---|---|---|
| 45; | $R_1$ = H | $R_2$ = H | $R_3$ = $CH_3$ | X = 3',4'-Cl |
| 46; | $R_1$ = H | $R_2$ = H | $R_3$ = $CH_2CH_3$ | X = 3',4'-Cl |
| 47; | $R_1$ = H | $R_2$ = H | $R_3$ = $CH_3$ | X = 4-$CF_3$ |
| 48; | $R_1$ = H | $R_2$ = H | $R_3$ = $CH_2CH_3$ | X = 4-$CF_3$ |
| 49; | $R_1$ = H | $R_2$ = H | $R_3$ = $CH_3$ | X = 4-$OCF_3$ |
| 50; | $R_1$ = H | $R_2$ = H | $R_3$ = $CH_2CH_3$ | X = 4-$OCF_3$ |
| 51; | $R_1$ = H | $R_2$ = $CH_3$ | $R_3$ = $CH_3$ | X = 3',4'-Cl |
| 52; | $R_1$ = H | $R_2$ = $CH_3$ | $R_3$ = $CH_3$ | X = 4-$CF_3$ |

Preparation Example 32: Preparation of (R)/(S)-tert-butyl (1-(((3',4'-dichloro-[1,1'-biphenyl]-4-yl)methyl)amino)-1-oxopentan-2-yl)carbamate (37)

Compound 5 (0.57 g, 2.64 mmol), NMM (0.73 ml, 6.60 mmol), IBCF (0.45 ml, 3.43 mmol), and Compound 15 (0.80 g, 2.77 mmol) were reacted using Reaction Scheme e to synthesize Compound 37, (R)/(S)-tert-butyl (1-((3',4'-dichloro-[1,1'-biphenyl]-4-yl)methyl)amino)-1-oxopentan-2-yl)carbamate (1.20 g, 100%) in the form of a white powder.

$R_f$=0.04 (EtOAc 1: n-hexane 3);
$^1$H NMR (CDCl$_3$, 400 MHz) 7.64 (d, J=2.0 Hz, ArH), 7.49 (dd, J=2.6 Hz, 8.5 Hz, ArH), 7.33-7.40 (m, ArH), 6.48 (s, C(O)NH), 4.93 (s, Boc-NH), 4.49 (d, J=4.2 Hz, NHCH$_2$), 4.07-4.09 (m, Chiral-H), 1.36-1.43 (m, CH$_2$CH$_2$CH$_3$, Boc), 0.95 (t, J=7.3 Hz, CH$_2$CH$_2$CH$_3$).

Preparation Example 33: Preparation of (R)/(S)-tert-butyl (1-(((3',4'-dichloro-[1,1'-biphenyl]-4-yl)methyl)amino)-1-oxohexan-2-yl)carbamate (38)

Compound 6 (0.38 g, 1.65 mmol), NMM (0.45 ml, 4.13 mmol), IBCF (0.28 ml, 2.15 mmol), and Compound 15 (0.50 g, 1.74 mmol) were reacted using Reaction Scheme e to synthesize Compound 38, (R)/(S)-tert-butyl (1-(((3',4'-dichloro-[1,1'-biphenyl]-4-yl)methyl)amino)-1-oxohexan-2-yl)carbamate (0.46 g, 60%) in the form of a white powder.

$R_f$=0.19 (EtOAc 1: n-hexane 3);
$^1$H NMR (CDCl$_3$, 400 MHz) 7.63 (d, J=2.0 Hz, ArH), 7.49 (dd, J=4.3 Hz, 8.2 Hz, ArH), 7.33-7.39 (m, ArH), 6.55 (s, C(O)NH), 4.98 (d, J=3.8 Hz, Boc-NH), 4.49 (d, J=5.5 Hz, NHCH$_2$), 4.07-4.11 (m, Chiral-H), 1.58-1.90 (m, CH$_2$CH$_2$CH$_2$CH$_3$), 1.42 (s, Boc), 1.34 (d, J=2.2 Hz, CH$_2$CH$_2$CH$_2$CH$_3$), 0.88-0.94 (m, CH$_2$CH$_2$CH$_2$CH$_3$).

Preparation Example 34: Preparation of (R)/(S)-tert-butyl (1-oxo-1(((4'-(trifluoromethyl)-[1,1'-biphenyl]-4-yl)methyl)amino)pentan-2-yl)carbamate (39)

Compound 5 (0.36 g, 1.66 mmol), NMM (0.46 ml, 4.14 mmol), IBCF (0.28 ml, 2.15 mmol), and Compound 16 (0.50 g, 1.74 mmol) were reacted using Reaction Scheme e to synthesize Compound 39, (R)/(S)-tert-butyl (1-oxo-1-(4'-(trifluoromethyl)-[1,1'-biphenyl]-4-yl)methyl)amino)pentan-2-yl)carbamate (0.72 g, 96%) in the form of a white powder.

$R_f$=0.17 (EtOAc 1: n-hexane 3);
$^1$H NMR (CDCl$_3$, 300 MHz) 7.62-7.70 (m, ArH), 7.44 (dd, J=8.1 Hz, 44.7 Hz, ArH), 6.85 (s, C(O)NH), 5.16-5.18 (m, Boc-NH), 4.47-4.49 (m, ArCH$_2$), 4.11-4.15 (m, Chiral-H), 1.54-1.89 (m, CH$_2$CH$_2$CH$_3$), 1.41 (s, Boc, CH$_2$CH$_2$CH$_3$), 0.93 (t, J=7.2 Hz, CH$_2$CH$_2$CH$_3$).

Preparation Example 35: Preparation of (R)/(S)-tert-butyl (1-oxo-1(((4'-(trifluoromethyl)-[1,1'-biphenyl]-4-yl)methyl)amino)hexan-2-yl)carbamate (40)

Compound 6 (0.54 g, 2.32 mmol), NMM (0.71 ml, 6.49 mmol), IBCF (0.39 ml, 3.01 mmol), and Compound 16 (0.70 g, 2.43 mmol) were reacted using Reaction Scheme e to synthesize Compound 40, (R)/(S)-tert-butyl (1-oxo-1-(4'-(trifluoromethyl)-[1,1'-biphenyl]-4-yl)methyl)amino)hexan-2-yl)carbamate (0.87 g, 81%) in the form of a white powder.

$R_f$=0.16 (EtOAc 1: n-hexane 3);
$^1$H NMR (CDCl$_3$, 400 MHz) 7.70 (q, J=4.6 Hz, 8.6 Hz, ArH), 7.57 (d, J=8.2 Hz, ArH), 7.39 (d, J=8.2 Hz, ArH), 6.50 (s, C(O)NH), 4.96 (s, Boc-NH), 4.53 (d, J=4.7 Hz, NHCH$_2$), 4.09-4.10 (m, Chiral-H), 1.59-1.94 (m, CH$_2$CH$_2$CH$_2$CH$_3$), 1.45 (s, Boc), 1.37-1.38 (m, CH$_2$CH$_2$CH$_2$CH$_3$), 0.93 (t, J=7.0 Hz, CH$_2$CH$_2$CH$_2$CH$_3$).

Preparation Example 36: Preparation of (R)/(S)-tert-butyl (1-oxo-1(((4'-(trifluoromethoxy)-[1,1'-biphenyl]-4-yl)methyl)amino)pentan-2-yl)carbamate (41)

Compound 5 (0.55 g, 2.51 mmol), NMM (0.77 ml, 7.02 mmol), IBCF (0.42 ml, 3.26 mmol), and Compound 17 (0.80 g, 2.63 mmol) were reacted using Reaction Scheme e to synthesize Compound 41, (R)/(S)-tert-butyl (1-oxo-1-(((4'-(trifluoromethoxy)-[1,1-biphenyl]-4-yl)methyl)amino)pentan-2-yl)carbamate (1.05 g, 90%) in the form of a white powder.

$R_f$=0.09 (EtOAc 1: n-hexane 3);
$^1$H NMR (CDCl$_3$, 400 MHz) 7.57-7.61 (m, ArH), 7.53 (d, J=8.2 Hz, ArH), 7.37 (d, J=8.2 Hz, ArH), 7.30 (d, J=8.2 Hz, ArH), 6.47 (s, C(O)NH), 4.96 (s, Boc-NH), 4.52 (s, NHCH$_2$), 4.10-4.11 (m, Chiral-H), 1.59-1.94 (m, CH$_2$CH$_2$CH$_3$), 1.37-1.45 (m, CH$_2$CH$_2$CH$_3$, Boc), 0.97 (t, J=7.3 Hz, CH$_2$CH$_2$CH$_3$).

Preparation Example 37: Preparation of (R)/(S)-tert-butyl (1-oxo-1(((4'-(trifluoromethoxy)-[1,1'-biphenyl]-4-yl)methyl)amino)hexan-2-yl)carbamate (42)

Compound 6 (0.58 g, 2.51 mmol), NMM (0.77 ml, 7.02 mmol), IBCF (0.42 ml, 3.26 mmol), and Compound 17 (0.80 g, 2.63 mmol) were reacted using Reaction Scheme e to synthesize Compound 42, (R)/(S)-tert-butyl (1-oxo-1-(((4'-(trifluoromethoxy)-[1,1'-biphenyl]-4-yl)methyl)amino)hexan-2-yl)carbamate (1.06 g, 88%) in the form of a white powder.

$R_f$=0.18 (EtOAc 1: n-hexane 3);

$^1$H NMR (CDCl$_3$, 400 MHz) 7.58-7.61 (m, ArH), 7.53 (d, J=8.1 Hz, ArH), 7.37 (d, J=8.1 Hz, ArH), 7.30 (d, J=8.5 Hz, ArH), 6.52 (s, C(O)NH), 4.99 (s, Boc-NH), 4.53 (d, J=5.1 Hz, NHCH$_2$), 4.09-4.11 (m, Chiral-H), 1.62-1.94 (m, CH$_2$CH$_2$CH$_2$CH$_3$), 1.45 (s, Boc), 1.36-1.37 (m, CH$_2$CH$_2$CH$_2$CH$_3$), 0.92 (t, J=6.9 Hz, CH$_2$CH$_2$CH$_2$CH$_3$).

Preparation Example 38: Preparation of (R)/(S)-tert-butyl (1-(((3',4'-dichloro-[1,1'-biphenyl]-4-yl)methyl)amino)-1-oxopentan-2-yl)(methyl)carbamate (43)

Compound 8 (0.38 g, 1.65 mmol), NMM (0.46 ml, 4.13 mmol), IBCF (0.28 ml, 2.15 mmol), and Compound 15 (0.50 g, 1.73 mmol) were reacted using Reaction Scheme e to synthesize Compound 43, (R)/(S)-tert-butyl (1-(((3',4'-dichloro-[1,1'-biphenyl]-4-yl)methyl)amino)-1-oxopentan-2-yl)(methyl)carbamate (0.57 g, 73%) in the form of an oil.

$R_f$=0.18 (EtOAc 1: n-hexane 3);

$^1$H NMR (CDCl$_3$, 300 MHz) 7.30-7.68 (m, ArH), 6.27-6.64 (m, C(O)NH), 4.41-4.59 (m, NHCH$_2$, Chiral-H), 2.78 (s, NCH$_3$), 2.04-1.63 (m, CH$_2$CH$_2$CH$_3$), 1.44 (s, Boc), 1.32-1.26 (m, CH$_2$CH$_2$CH$_3$), 0.96 (t, J=7.3 Hz, CH$_2$CH$_2$CH$_3$).

Preparation Example 39: Preparation of (R)/(S)-tert-butyl methyl(1-oxo-1-(((4'-(trifluoromethyl)-[1,1'-biphenyl]-4-yl)methyl)amino)pentan-2-yl)carbamate (44)

Compound 8 (0.38 g, 1.66 mmol), NMM (0.46 ml, 4.14 mmol), IBCF (0.28 ml, 2.15 mmol), and Compound 16 (0.50 g, 1.74 mmol) were reacted using Reaction Scheme e to synthesize Compound 44, (R)/(S)-tert-butyl methyl (1-oxo-1-(((4'-(trifluoromethyl)-[1,1'-biphenyl]-4-yl)methyl)amino)pentan-2-yl)carbamate (0.49 g, 64%) in the form of an oil.

$R_f$=0.22 (EtOAc 1: n-hexane 3);

$^1$H NMR (CDCl$_3$, 300 MHz) 7.64-7.71 (m, ArH), 7.44 (dd, J=7.9 Hz, 53.4 Hz, ArH), 6.28-6.64 (m, C(O)NH), 4.43-4.61 (m, NHCH$_2$, Chiral-H), 2.78 (s, NCH$_3$), 1.63-2.04 (m, CH$_2$CH$_2$CH$_3$), 1.44 (s, Boc), 1.26-1.35 (m, CH$_2$CH$_2$CH$_3$), 0.96 (t, J=7.3 Hz, CH$_2$CH$_2$CH$_3$).

Preparation Example 40: Preparation of (R)/(S)-2-amino-N-((3',4'-dichloro-[1,1'-biphenyl]-4-yl)methyl)pentanamide hydrochloride (45)

Compound 37 (1.19 g, 2.64 mmol) and 4.0 M HCl (3.95 ml, 15.8 mmol in dioxane) were reacted using Reaction Scheme f to synthesize Compound 45, (R)/(S)-2-amino-N-((3',4'-dichloro-[1,1'-biphenyl]-4-yl)methyl)pentanamide hydrochloride (0.73 g, 71%) in the form of a white powder.

$R_f$=0.00 (EtOAc 9: acetone 1);

$^1$H NMR (DMSO-d$_6$, 300 MHz) 9.04 (s, C(O)NH), 8.21 (s, NH$_3$), 7.94 (s, ArH), 7.66-7.73 (m, ArH), 7.40 (d, J=8.1 Hz, ArH), 4.39-4.41 (m, NHCH$_2$), 3.78-3.82 (t, J=6.3 Hz, Chiral-H), 1.68-1.76 (m, CH$_2$CH$_2$CH$_3$), 1.29-1.39 (m, CH$_2$CH$_2$CH$_3$), 0.89 (t, J=7.2 Hz, CH$_2$CH$_2$CH$_3$).

Preparation Example 41: Preparation of (R)/(S)-2-amino-N-((3',4'-dichloro-[1,1'-biphenyl]-4-yl)methyl)hexanamide hydrochloride (46)

Compound 38 (0.46 g, 0.99 mmol) and 4.0 M HCl (1.48 ml, 1.48 mmol in dioxane) were reacted using Reaction Scheme f to synthesize Compound 46, (R)/(S)-2-amino-N-((3',4'-dichloro-[1,1'-biphenyl]-4-yl)methyl)hexanamide hydrochloride (0.27 g, 85%) in the form of a white powder.

$R_f$=0.00 (EtOAc 9: acetone 1);

$^1$H NMR (DMSO-d$_6$, 400 MHz) 9.17 (m, C(O)NH), 8.32 (s, NH$_3$), 7.94 (d, J=2.0 Hz, ArH), 7.66-7.73 (m, ArH), 7.41 (d, J=8.2 Hz, ArH), 4.34-4.45 (m, NHCH$_2$), 3.81 (t, J=6.1 Hz, Chiral-H), 1.75-1.76 (m, CH$_2$CH$_2$CH$_2$CH$_3$), 1.27-1.28 (m, CH$_2$CH$_2$CH$_2$CH$_3$), 0.85 (t, J=6.6 Hz, CH$_2$CH$_2$CH$_2$CH$_3$).

Preparation Example 42: Preparation of (R)/(S)-2-amino-N-((4'-(trifluoromethyl)-[1,1'-biphenyl]-4-yl)methyl)pentanamide hydrochloride (47)

Compound 39 (0.70 g, 1.55 mmol) and 4.0 M HCl (2.33 ml, 9.32 mmol in dioxane) were reacted using Reaction Scheme f to synthesize Compound 47, (R)/(S)-2-amino-N-(4'-(trifluoromethyl)-[1,1'-biphenyl]-4-yl)methyl)pentanamide hydrochloride (0.60 g, 99%) in the form of a white powder.

$R_f$=0.00 (EtOAc 9: acetone 1);

$^1$H NMR (DMSO-d$_6$, 300 MHz) 9.37 (t, J=5.7 Hz, C(O)NH), 8.46 (s, NH$_3$), 7.71-7.92 (m, ArH), 7.45-7.51 (m, ArH), 4.40-4.43 (m, NHCH$_2$), 3.89 (s, Chiral-H), 1.74-1.82 (m, CH$_2$CH$_2$CH$_3$), 1.16-1.42 (m, CH$_2$CH$_2$CH$_3$), 0.89 (t, J=7.2 Hz, CH$_2$CH$_2$CH$_3$).

Preparation Example 43: Preparation of (R)/(S)-2-amino-N-((4'-(trifluoromethyl)-[1,1'-biphenyl]-4-yl)methyl)hexanamide hydrochloride (48)

Compound 40 (0.85 g, 1.83 mmol) and 4.0 M HCl (2.75 ml, 11.0 mmol in dioxane) were reacted using Reaction Scheme f to synthesize Compound 48, (R)/(S)-2-amino-N-(4'-(trifluoromethyl)-[1,1'-biphenyl]-4-yl)methyl)hexanamide hydrochloride (0.72 g, 98%) in the form of a white powder.

$R_f$=0.00 (EtOAc 9: acetone 1);

$^1$H NMR (DMSO-d$_6$, 400 MHz) 9.09 (s, C(O)NH), 8.23 (s, NH$_3$), 7.89 (d, J=8.2 Hz, ArH), 7.82 (d, J=8.4 Hz, ArH), 7.73 (d, J=8.1 Hz, ArH), 7.44 (d, J=8.1 Hz, ArH), 4.36-4.46 (m, NHCH$_2$), 3.80 (t, J=6.4 Hz, Chiral-H), 1.74-1.76 (m, CH$_2$CH$_2$CH$_2$CH$_3$), 1.27-1.29 (m, CH$_2$CH$_2$CH$_2$CH$_3$), 0.85 (t, J=6.5 Hz, CH$_2$CH$_2$CH$_2$CH$_3$).

Preparation Example 44: Preparation of (R)/(S)-2-amino-N-((4'-(trifluoromethoxy)-[1,1'-biphenyl]-4-yl)methyl)pentanamide hydrochloride (49)

Compound 41 (1.04 g, 2.22 mmol) and 4.0 M HCl (3.34 ml, 13.3 mmol in dioxane) were reacted using Reaction Scheme f to synthesize Compound 49, (R)/(S)-2-amino-N-((4'-(trifluoromethoxy)-[1,1'-biphenyl]-4-yl)methyl)pentanamide hydrochloride (0.82 g, 92%) in the form of a white powder.

$R_f$=0.00 (EtOAc 9: acetone 1);

$^1$H NMR (DMSO-d$_6$, 400 MHz) 9.14 (t, J=5.7 Hz, C(O)NH), 8.30 (s, NH$_3$), 7.77-7.81 (m, ArH), 7.67 (d, J=8.2 Hz, ArH), 7.46 (d, J=8.1 Hz, ArH), 7.41 (d, J=8.2 Hz, ArH), 4.40

(d, J=5.8 Hz, NHCH$_2$), 3.82 (t, J=6.5 Hz, Chiral-H), 1.71-1.76 (m, CH$_2$CH$_2$CH$_3$), 1.28-1.38 (m, CH$_2$CH$_2$CH$_3$), 0.89 (t, J=7.3 Hz, CH$_2$CH$_2$CH$_3$).

Preparation Example 45: Preparation of (R)/(S)-2-amino-N-((4'-(trifluoromethoxy)-[1,1'-biphenyl]-4-yl)methyl)hexanamide hydrochloride (50)

Compound 42 (1.04 g, 2.17 mmol) and 4.0 M HCl (3.26 ml, 13.0 mmol in dioxane) were reacted using Reaction Scheme f to synthesize Compound 50, (R)/(S)-2-amino-N-((4'-(trifluoromethoxy)-[1,1'-biphenyl]-4-yl)methyl)hexanamide hydrochloride (0.88 g, 97%) in the form of a white powder.

R$_f$=0.00 (EtOAc 9: acetone 1);

$^1$H NMR (DMSO-d$_6$, 400 MHz) 9.09 (t, J=5.8 Hz, C(O)NH), 8.25 (s, NH$_3$), 7.78 (d, J=8.7 Hz, ArH), 7.66 (d, J=8.2 Hz, ArH), 7.45 (d, J=8.3 Hz, ArH), 7.41 (d, J=8.2 Hz, ArH), 4.35-4.44 (m, NHCH$_2$), 3.80 (t, J=6.4 Hz, Chiral-H), 1.72-1.75 (m, CH$_2$CH$_2$CH$_2$CH$_3$), 1.27-1.28 (m, CH$_2$CH$_2$CH$_2$CH$_3$), 0.85 (t, J=6.5 Hz, CH$_2$CH$_2$CH$_2$CH$_3$).

Preparation Example 46: Preparation of (R)/(S)-N-((3',4'-dichloro-[1,1'-biphenyl]-4-yl)methyl)-2-(methylamino)pentanamide hydrochloride (51)

Compound 43 (0.84 g, 1.81 mmol) and 4.0 M HCl (2.80 ml, 10.9 mmol in dioxane) were reacted using Reaction Scheme f to synthesize Compound 51, (R)/(S)-N-(3',4'-dichloro-[1,1'-biphenyl]-4-yl)methyl)-2-(methylamino)pentanamide hydrochloride (0.64 g, 88%) in the form of a white powder.

R$_f$=0.00 (EtOAc 9: acetone 1);

$^1$H NMR (DMSO-d$_6$, 300 MHz) 9.10-9.78 (m, NH$_2$), 9.57 (t, J=5.5 Hz, C(O)NH), 7.96 (s, ArH), 7.69-7.72 (m, ArH), 7.43 (d, J=10.7 Hz, ArH), 4.42-4.44 (m, NHCH$_2$), 3.85-3.90 (m, Chiral-H), 2.48 (s, NCH$_3$), 1.76-1.90 (m, CH$_2$CH$_2$CH$_3$), 1.26-1.38 (m, CH$_2$CH$_2$CH$_3$), 0.90 (t, J=7.1 Hz, CH$_2$CH$_2$CH$_3$).

Preparation Example 47: Preparation of (R)/(S)-2-(methylamino)-N-((4'-(trifluoromethyl)-[1,1'-biphenyl]-4-yl)methyl)pentanamide hydrochloride (52)

Compound 44 (0.45 g, 0.97 mmol) and 4.0 M HCl (1.45 ml, 5.81 mmol in dioxane) were reacted using Reaction Scheme f to synthesize Compound 52, (R)/(S)-2-(methylamino)-N-((4'-(trifluoromethyl)-[1,1'-biphenyl]-4-yl)methyl)pentanamide hydrochloride (0.32 g, 82%) in the form of a white powder.

R$_f$=0.00 (EtOAc 9: acetone 1);

$^1$H NMR (DMSO-d$_6$, 300 MHz) 9.03-9.81 (m, NH$_2$), 9.52 (t, J=5.5 Hz, C(O)NH), 7.72-7.92 (m, ArH), 7.46 (d, J=8.2 Hz, ArH), 4.43-4.45 (m, NHCH$_2$), 3.86 (s, Chiral-H), 2.48 (s, NCH$_3$), 1.77-1.89 (m, CH$_2$CH$_2$CH$_3$), 1.25-1.38 (m, CH$_2$CH$_2$CH$_3$), 0.90 (t, J=7.2 Hz, CH$_2$CH$_2$CH$_3$).

$$\xrightarrow[\text{MeOH, H}_2 \text{ (rt.)}]{\text{Formaldehyde, Pd/C}}$$

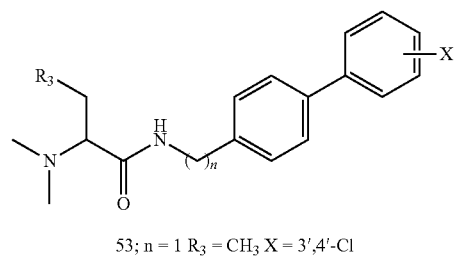

53; n = 1 R$_3$ = CH$_3$ X = 3',4'-Cl

Preparation Example 48: Preparation of (R)/(S)-N-((3',4'-dichloro-[1,1'-biphenyl]-4-yl)methyl)-2-(dimethylamino)pentanamide (53)

Compound 45 (1.0 eq), triethylamine (6.0 eq), formaldehyde (1.05 eq), and a palladium catalyst (0.2 eq) were reacted using Reaction Scheme g to synthesize Compound 53, (R)/(S)-N-((3',4'-dichloro-[1,1'-biphenyl]-4-yl)methyl)-2-(dimethylamino)pentanamide.

$^1$H NMR (DMSO-d$_6$, 300 MHz) 9.57 (t, J=5.5 Hz, C(O)NH), 7.96 (s, ArH), 7.69-7.72 (m, ArH), 7.43 (d, J=10.7 Hz, ArH), 4.42-4.44 (m, NHCH$_2$), 3.85-3.90 (m, Chiral-H), 2.48 (s, N(CH$_3$)$_2$), 1.76-1.90 (m, CH$_2$CH$_2$CH$_3$), 1.26-1.38 (m, CH$_2$CH$_2$CH$_3$), 0.90 (t, J=7.1 Hz, CH$_2$CH$_2$CH$_3$).

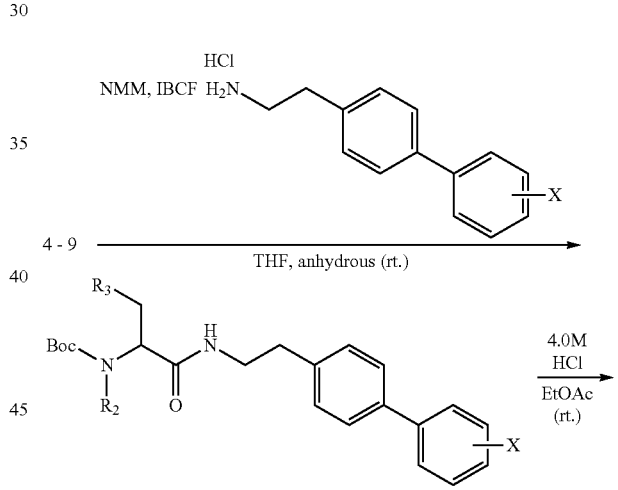

| # | R$_2$ | R$_3$ | X |
|---|---|---|---|
| 54 | H | CH | 3',4'-Cl |
| 55 | H | CH$_2$CH$_3$ | 3',4'-Cl |
| 56 | H | CH$_2$CH$_2$CH$_3$ | 3',4'-Cl |
| 57 | H | CH$_3$ | 4-CF$_3$ |
| 58 | H | CH$_2$CH$_3$ | 4-CF$_3$ |
| 59 | H | CH$_2$CH$_2$CH$_3$ | 4-CF$_3$ |
| 60 | H | CH$_3$ | 4-OCF$_3$ |
| 61 | H | CH$_2$CH$_3$ | 4-OCF$_3$ |
| 62 | H | CH$_2$CH$_2$CH$_3$ | 4-OCF$_3$ |
| 63 | H | CH$_2$CH$_3$ | 3',4'-F |
| 64 | CH$_3$ | CH$_3$ | 3',4'-Cl |
| 65 | CH$_3$ | CH$_2$CH$_3$ | 3',4'-Cl |
| 66 | CH$_3$ | CH$_2$CH$_2$CH$_3$ | 3',4'-Cl |
| 67 | CH$_3$ | CH$_3$ | 4-CF$_3$ |
| 68 | CH$_3$ | CH$_2$CH$_3$ | 4-CF$_3$ |
| 69 | CH$_3$ | CH$_2$CH$_2$CH$_3$ | 4-CF$_3$ |
| 70 | CH$_3$ | CH$_3$ | 4-OCF$_3$ |
| 71 | CH$_3$ | CH$_2$CH$_3$ | 4-OCF$_3$ |
| 72 | CH$_3$ | CH$_2$CH$_2$CH$_3$ | 4-OCF$_3$ |

-continued

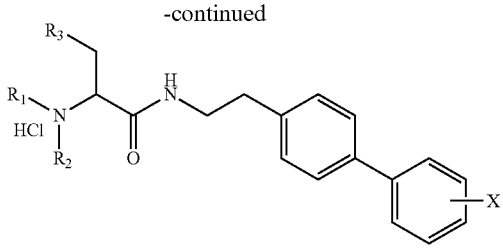

| | | | |
|---|---|---|---|
| 73; R₁ = H | R₂ = H | R₃ = CH₃ | X = 3',4'-Cl |
| 74; R₁ = H | R₂ = H | R₃ = CH₂CH₃ | X = 3',4'-Cl |
| 75; R₁ = H | R₂ = H | R₃ = CH₂CH₂CH₃ | X = 3',4'-Cl |
| 76; R₁ = H | R₂ = H | R₃ = CH₃ | X = 4-CF₃ |
| 77; R₁ = H | R₂ = H | R₃ = CH₂CH₃ | X = 4-CF₃ |
| 78; R₁ = H | R₂ = H | R₃ = CH₂CH₂CH₃ | X = 4-CF₃ |
| 79; R₁ = H | R₂ = H | R₃ = CH₃ | X = 4-OCF₃ |
| 80; R₁ = H | R₂ = H | R₃ = CH₂CH₃ | X = 4-OCF₃ |
| 81; R₁ = H | R₂ = H | R₃ = CH₂CH₂CH₃ | X = 4-OCF₃ |
| 82; R₁ = H | R₂ = H | R₃ = CH₂CH₃ | X = 3',4'-F |
| 83; R₁ = H | R₂ = CH₃ | R₃ = CH₃ | X = 3',4'-Cl |
| 84; R₁ = H | R₂ = CH₃ | R₃ = CH₂CH₃ | X = 3',4'-Cl |
| 85; R₁ = H | R₂ = CH₃ | R₃ = CH₂CH₂CH₃ | X = 3',4'-Cl |
| 86; R₁ = H | R₂ = CH₃ | R₃ = CH₃ | X = 4-CF₃ |
| 87; R₁ = H | R₂ = CH₃ | R₃ = CH₂CH₃ | X = 4-CF₃ |
| 88; R₁ = H | R₂ = CH₃ | R₃ = CH₂CH₂CH₃ | X = 4-CF₃ |
| 89; R₁ = H | R₂ = CH₃ | R₃ = CH₃ | X = 4-OCF₃ |
| 90; R₁ = H | R₂ = CH₃ | R₃ = CH₂CH₃ | X = 4-OCF₃ |
| 91; R₁ = H | R₂ = CH₃ | R₃ = CH₂CH₂CH₃ | X = 4-OCF₃ |

Preparation Example 49: Preparation of (R)/(S)-tert-butyl (1-((2-(3',4'-dichloro-[1,1'-biphenyl]-4-yl)ethyl)amino)-1-oxobutan-2-yl)carbamate (54)

Compound 4 (0.32 g, 1.57 mmol), NMM (0.43 ml, 3.93 mmol), IBCF (0.27 ml, 2.05 mmol), and Compound 18 (0.50 g, 1.65 mmol) were reacted using Reaction Scheme e to synthesize Compound 54, (R)/(S)-tert-butyl (1-((2-(3',4'-dichloro-[1,1'-biphenyl]-4-yl)ethyl)amino)-1-oxobutan-2-yl)carbamate (0.66 g, 93%) in the form of a white powder.

$R_f$=0.05 (EtOAc 1: n-hexane 3);
$^1$H NMR (CDCl₃, 400 MHz) 7.65 (s, ArH), 7.47-7.50 (m, ArH), 7.39 (d, J=8.2 Hz, ArH), 7.26-7.28 (m, ArH), 6.07 (s, C(O)NH), 4.94 (s, Boc-NH), 3.93 (d, J=6.6 Hz, Chiral-H), 3.50-3.94 (m, NHCH₂CH₂), 2.86 (t, J=6.9 Hz, NHCH₂CH₂), 1.55-2.88 (m, CH₂CH₃), 1.43 (s, Boc), 0.91 (t, J=7.4 Hz, CH₂CH₃).

Preparation Example 50: Preparation of (R)/(S)-tert-butyl (1-((2-(3',4'-dichloro-[1,1'-biphenyl]-4-yl)ethyl)amino)-1-oxopentan-2-yl)carbamate (55)

Compound 5 (0.50 g, 2.30 mmol), NMM (0.51 ml, 4.60 mmol), IBCF (0.39 ml, 2.99 mmol), and Compound 18 (0.73 g, 2.42 mmol) were reacted using Reaction Scheme e to synthesize Compound 55, (R)/(S)-tert-butyl (1-((2-(3',4'-dichloro-[1,1'-biphenyl]-4-yl)ethyl)amino)-1-oxopentan-2-yl)carbamate (0.96 g, 89%) in the form of a white powder.

$R_f$=0.26 (EtOAc 1: n-hexane 3);
$^1$H NMR (CDCl₃, 400 MHz) 7.46-7.64 (m, ArH), 7.26-7.40 (m, ArH), 6.36 (s, C(O)NH), 5.07 (s, Boc-NH), 4.01-4.03 (m, Chiral-H), 3.47-3.61 (m, NHCH₂CH₂), 2.85 (t, J=7.0 Hz, NHCH₂CH₂), 2.67 (s, NCH₃), 1.48-1.80 (m, CH₂CH₂CH₃), 1.42 (s, Boc), 1.26-1.36 (m, CH₂CH₂CH₃), 0.90 (t, J=7.2 Hz, CH₂CH₂CH₃).

Preparation Example 51: Preparation of (R)/(S)-tert-butyl (1-((2-(3',4'-dichloro-[1,1'-biphenyl]-4-yl)ethyl)amino)-1-oxohexan-2-yl)carbamate (56)

Compound 6 (0.36 g, 1.57 mmol), NMM (0.43 ml, 3.93 mmol), IBCF (0.27 g, 2.05 mmol), and Compound 18 (0.50 g, 16.5 mmol) were reacted using Reaction Scheme e to synthesize Compound 56, (R)/(S)-tert-butyl (1-((2-(3',4'-dichloro-[1,1'-biphenyl]-4-yl)ethyl)amino)-1-oxohexan-2-yl)carbamate (0.76 g, 100%) in the form of a white powder.

$R_f$=0.07 (EtOAc 1: n-hexane 3);
$^1$H NMR (CDCl₃, 400 MHz) 7.65 (s, ArH), 7.48 (d, J=6.3 Hz, ArH), 7.39 (d, J=8.0 Hz, ArH), 7.26-7.28 (m, ArH), 6.07 (s, C(O)NH), 4.91 (s, Boc-NH), 3.97 (d, J=5.6 Hz, Chiral-H), 3.51-3.62 (m, NHCH₂CH₂), 2.86 (t, J=6.1 Hz, NHCH₂CH₂), 1.51-1.81 (m, CH₂CH₂CH₂CH₃), 1.42 (s, Boc), 1.27 (d, J=6.7 Hz, CH₂CH₂CH₃), 0.87 (d, J=5.5 Hz, CH₂CH₂CH₂CH₃).

Preparation Example 52: Preparation of (R)/(S)-tert-butyl (1-oxo-1-(4'-(trifluoromethyl)-[1,1'-biphenyl]-4-yl)ethyl)amino)butan-2-yl)carbamate (57)

Compound 4 (0.42 g, 2.08 mmol), NMM (0.57 ml, 5.21 mmol), IBCF (0.35 ml, 2.71 mmol), and Compound 19 (0.66 g, 2.19 mmol) were reacted using Reaction Scheme e to synthesize Compound 57, (R)/(S)-tert-butyl (1-oxo-1-((2-(4'-(trifluoromethyl)-[1,1'-biphenyl]-4-yl)ethyl)amino)butan-2-yl)carbamate (0.92 g, 98%) in the form of a white powder.

$R_f$=0.16 (EtOAc 1: n-hexane 3);
$^1$H NMR (CDCl₃, 400 MHz) 7.70 (s, ArH), 7.57 (d, J=8.0 Hz, ArH), 7.29-7.33 (m, ArH), 6.15 (s, C(O)NH), 5.00 (s, Boc-NH), 3.94-3.99 (m, Chiral-H), 3.53-3.66 (m, NHCH₂CH₂), 2.90 (t, J=7.0 Hz, NHCH₂CH₂), 1.58-1.90 (m, CH₂CH₃), 1.45 (s, Boc), 0.93 (t, J=7.5 Hz, CH₂CH₃).

Preparation Example 53: Preparation of (R)/(S)-tert-butyl (1-oxo-1-(4'-(trifluoromethyl)-[1,1'-biphenyl]-4-yl)ethyl)amino)pentan-2-yl)carbamate (58)

Compound 5 (0.55 g, 2.53 mmol), NMM (0.69 ml, 6.31 mmol), IBCF (0.43 ml, 3.28 mmol), and Compound 19 (0.80 g, 2.65 mmol) were reacted using Reaction Scheme e to synthesize Compound 58, (R)/(S)-tert-butyl (1-oxo-1-((2-(4'-(trifluoromethyl)-[1,1'-biphenyl]-4-yl)ethyl)amino)pentan-2-yl)carbamate (1.05 g, 89%) in the form of a white powder.

$R_f$=0.20(EtOAc 1: n-hexane 3);
$^1$H NMR (CDCl₃, 300 MHz) 7.67 (s, ArH), 7.41 (dd, J=8.1 Hz, 63.6 Hz, ArH), 6.36 (s, C(O)NH), 5.05-5.07 (m, Boc-NH), 4.00-4.05 (m, Chiral-H), 3.45-3.66 (m, NHCH₂CH₂), 2.87 (t, J=7.1 Hz, NHCH₂CH₂), 1.50-1.83 (m, CH₂CH₂CH₃), 1.42 (s, Boc), 1.28-1.39 (m, CH₂CH₂CH₃), 0.90 (t, J=7.2 Hz, CH₂CH₂CH₃).

Preparation Example 54: Preparation of (R)/(S)-tert-butyl (1-oxo-1-((2-(4'-(trifluoromethyl)-[1,1'-biphenyl]-4-yl)ethyl)amino)carbamate (59)

Compound 6 (0.76 g, 3.16 mmol), NMM (0.87 ml, 7.89 mmol), IBCF (0.53 ml, 4.10 mmol), and Compound 19 (1.00 g, 3.31 mmol) were reacted using Reaction Scheme e to synthesize Compound 59, (R)/(S)-tert-butyl (1-oxo-1-((2-(4'-(trifluoromethyl)-[1,1'-biphenyl]-4-yl)ethyl)amino)carbamate (1.34 g, 89%) in the form of a white powder.

$R_f$=0.13 (EtOAc 1: n-hexane 3);

¹H NMR (DMSO-d₆, 400 MHz) 7.87 (d, J=8.2 Hz, ArH, C(O)NH), 7.80 (d, J=8.5 Hz, ArH), 7.66 (d, J=8.1 Hz, ArH), 7.35 (d, J=8.1 Hz, ArH), 6.73 (d, J=8.2 Hz, Boc-NH), 3.83 (q, J=5.6 Hz, 8.4 Hz, Chiral-H), 3.24-3.43 (m, NHCH₂CH₂), 2.77 (t, J=7.0 Hz, NHCH₂CH₂), 1.37-1.52 (m, CH₂CH₂CH₂CH₃, Boc), 1.15-1.20 (m, CH₂CH₂CH₂CH₃), 0.80 (t, J=6.8 Hz, CH₂CH₂CH₂CH₃).

Preparation Example 55: Preparation of (R)/(S)-tert-butyl (1-oxo-1-((2-(4'-(trifluoromethoxy)-[1,1'-biphenyl]-4-yl)ethyl)amino)butan-2-yl)carbamate (60)

Compound 4 (0.49 g, 2.40 mmol), NMM (0.66 ml, 6.00 mmol), IBCF (0.41 ml, 3.12 mmol), and Compound 20 (0.80 g, 2.52 mmol) were reacted using Reaction Scheme e to synthesize Compound 60, (R)/(S)-tert-butyl (1-oxo-1-((2-(4'-(trifluoromethoxy)-[1,1'-biphenyl]-4-yl)ethyl)amino)butan-2-yl)carbamate (0.94 g, 84%) in the form of a white powder.
$R_f$=0.14 (EtOAc 1: n-hexane 3);
¹H NMR (CDCl₃, 400 MHz) 7.68-7.73 (m, ArH), 7.51-7.62 (m, ArH), 7.29-7.33 (m, ArH), 6.17 (d, J=5.6 Hz, C(O)NH), 5.01 (s, NH), 3.95-3.98 (m, Chiral-H), 3.51-3.67 (m, NHCH₂CH₂), 2.87-2.92 (m, NHCH₂CH₂), 1.56-1.92 (m, CH₂CH₃), 1.45 (s, Boc), 0.93 (t, J=7.4 Hz, CH₂CH₃).

Preparation Example 56: Preparation of (R)/(S)-tert-butyl (1-oxo-1-(4'-(trifluoromethoxy)-[1,1'-biphenyl]-4-yl)ethyl)amino)pentan-2-yl)carbamate (61)

Compound 5 (0.33 g, 1.50 mmol), NMM (0.41 ml, 3.75 mmol), IBCF (0.25 ml, 1.95 mmol), and Compound 20 (0.50 g, 1.57 mmol) were reacted using Reaction Scheme e to synthesize Compound 61, (R)/(S)-tert-butyl (1-oxo-1-(4'-(trifluoromethoxy)-[1,1'-biphenyl]-4-yl)ethyl)amino)pentan-2-yl)carbamate (0.70 g, 98%) in the form of a white powder.
$R_f$=0.12 (EtOAc 1: n-hexane 3);
¹H NMR (DMSO-d₆, 400 MHz) 7.88 (t, J=5.6 Hz, C(O)NH), 7.74-7.77 (m, ArH), 7.59 (d, J=8.2 Hz, ArH), 7.44 (d, J=8.1 Hz, ArH), 7.32 (d, J=8.2 Hz, ArH), 6.74 (d, J=8.2 Hz, Boc-NH), 4.86 (q, J=5.6 Hz, 8.2 Hz, Chiral-H), 3.26-3.40 (m, NHCH₂CH₂), 2.76 (t, J=7.0 Hz, NHCH₂CH₂), 1.37-1.52 (m, CH₂CH₂CH₃, Boc), 1.17-1.25 (m, CH₂CH₂CH₃), 0.81 (t, J=7.3 Hz, CH₂CH₂CH₃).

Preparation Example 57: Preparation of (R)/(S)-tert-butyl (1-oxo-1-((2-(4'-(trifluoromethoxy)-[1,1'-biphenyl]-4-yl)ethyl)amino)hexan-2-yl)carbamate (62)

Compound 6 (0.50 g, 2.18 mmol), NMM (0.60 ml, 5.45 mmol), IBCF (0.37 ml, 2.83 mmol), and Compound 20 (0.72 g, 2.29 mmol) were reacted using Reaction Scheme e to synthesize Compound 62, (R)/(S)-tert-butyl (1-oxo-1-((2-(4'-(trifluoromethoxy)-[1,1'-biphenyl]-4-yl)ethyl)amino)hexan-2-yl)carbamate (0.95 g, 88%) in the form of a white powder.
$R_f$=0.13 (EtOAc 1: n-hexane 3);
¹H NMR (CDCl₃, 400 MHz) 7.70-7.73 (m, ArH), 7.57 (d, J=8.1 Hz, ArH), 7.32 (d, J=8.1 Hz, ArH), 6.15 (s, C(O)NH), 4.95 (s, Boc-NH), 4.00 (q, J=6.4 Hz, 7.2 Hz, Chiral-H), 3.53-3.65 (m, NHCH₂CH₂), 2.90 (t, J=7.0 Hz, NHCH₂CH₂), 1.52-1.85 (m, CH₂CH₂CH₂CH₃), 1.45 (s, Boc), 1.31-1.34 (m, CH₂CH₂CH₂CH₃), 0.90 (t, J=6.9 Hz, CH₂CH₂CH₂CH₃).

Preparation Example 58: Preparation of (R)/(S)-tert-butyl (1-((2-(3',4'-difluoro-[1,1'-biphenyl]-4-yl)ethyl)amino)-1-oxopentan-2-yl)carbamate (63)

Compound 5 (0.50 g, 2.29 mmol), NMM (0.70 ml, 6.40 mmol), IBCF (0.39 ml, 2.97 mmol), and Compound 21 (0.80 g, 2.40 mmol) were reacted using Reaction Scheme e to synthesize Compound 63, (R)/(S)-tert-butyl (1-((2-(3',4'-difluoro-[1,1'-biphenyl]-4-yl)ethyl)amino)-1-oxopentan-2-yl)carbamate (0.97 g, 98%) in the form of a white powder.
$R_f$=0.10 (EtOAc 1: n-hexane 3);
¹H NMR (CDCl₃, 400 MHz) 7.46 (d, J=7.9 Hz, ArH), 7.33-7.38 (m, ArH), 7.17-7.27 (m, ArH), 6.11 (s, C(O)NH), 4.92 (s, Boc-NH), 3.96-4.01 (m, Chiral-H), 3.47-3.63 (m, NHCH₂CH₂), 2.85 (t, J=7.0 Hz, NHCH₂CH₂), 1.48-1.82 (m, CH₂CH₂CH₃), 1.42 (s, Boc), 1.26-1.36 (m, CH₂CH₂CH₃), 0.90 (t, J=7.3 Hz, CH₂CH₂CH₃).

Preparation Example 59: Preparation of (R)/(S)-tert-butyl (1-((2-(3',4'-dichloro-[1,1'-biphenyl]-4-yl)ethyl)amino)-1-oxobutan-2-yl)(methyl)carbamate (64)

Compound 7 (0.82 g, 3.78 mmol), NMM (1.04 ml, 9.44 mmol), IBCF (0.64 ml, 4.91 mmol), and Compound 18 (1.20 g, 3.97 mmol) were reacted using Reaction Scheme e to synthesize Compound 64, (R)/(S)-tert-butyl (1-((2-((3',4'-dichloro-[1,1'-biphenyl]-4-yl)ethyl)amino)-1-oxobutan-2-yl)(methyl)carbamate (1.38 g, 79%) in the form of an oil.
$R_f$=0.22 (EtOAc 1: n-hexane 3);
¹H NMR (CDCl₃, 400 MHz) 7.66 (d, J=2.0 Hz, ArH), 7.49-7.53 (m, ArH), 7.41 (dd, J=2.1 Hz, 6.3 Hz, ArH), 7.27-7.29 (m ArH), 6.26 (s, C(O)NH), 4.44 (s, Chiral-H), 3.55-3.64 (m, NHCH₂CH₂), 2.87 (t, J=6.7 Hz, NHCH₂CH₂), 2.70 (s, NCH₃), 1.61-1.98 (m, CH₂CH₃), 1.45 (s, Boc), 0.88 (t, J=7.4 Hz, CH₂CH₃).

Preparation Example 60: Preparation of (R)/(S)-tert-butyl (1-((2-(3',4'-dichloro-[1,1'-biphenyl]-4-yl)ethyl)amino)-1-oxopentan-2-yl)(methyl)carbamate (65)

Compound 8 (0.35 g, 1.51 mmol), NMM (0.33 ml, 3.03 mmol), IBCF (0.26 ml, 1.97 mmol), and Compound 18 (0.48 g, 1.59 mmol) were reacted using Reaction Scheme e to synthesize Compound 65, (R)/(S)-tert-butyl (1-((2-(3',4'-dichloro-[1,1'-biphenyl]-4-yl)ethyl)amino)-1-oxopentan-2-yl)(methyl)carbamate (0.69 g, 95%) in the form of an oil.
$R_f$=0.33 (EtOAc 1: n-hexane 3);
¹H NMR (CDCl₃, 400 MHz) 7.46-7.64 (m, ArH), 7.35-7.40 (m, ArH), 7.25-7.27 (m, ArH), 5.95-6.25 (m, C(O)NH), 4.51 (s, Chiral-H), 3.53-3.60 (m, NHCH₂CH₂), 2.84 (t, J=6.6 Hz, NHCH₂CH₂), 2.67 (s, NCH₃), 1.57-1.90 (m, CH₂CH₂CH₃), 1.42 (s, Boc), 1.22-1.32 (m, CH₂CH₂CH₃), 0.95 (t, J=7.3 Hz, CH₂CH₂CH₃).

Preparation Example 61: Preparation of (R)/(S)-tert-butyl (1-((2-(3',4'-dichloro-[1,1'-biphenyl]-4-yl)ethyl)amino)-1-oxohexan-2-yl)(methyl)carbamate (66)

Compound 9 (0.29 g, 1.20 mmol), NMM (0.33 ml, 2.99 mmol), IBCF (0.20 ml, 0.16 mmol), and Compound 18 (0.38 g, 1.26 mmol) were reacted using Reaction Scheme e to synthesize Compound 66, (R)/(S)-tert-butyl (1-((2-((3',4'-dichloro-[1,1'-biphenyl]-4-yl)ethyl)amino)-1-oxohexan-2-yl)(methyl)carbamate (0.60 g, 97%) in the form of an oil.

R$_f$=0.30 (EtOAc 1: n-hexane 3);
$^1$H NMR (DMSO-d$_6$, 400 MHz) 7.89 (d, J=1.9 Hz, ArH, C(O)NH), 7.62-7.71 (m, ArH), 7.30 (d, J=8.1 Hz, ArH), 4.27-4.47 (m, Chiral-H), 3.32-3.35 (m, NHCH$_2$CH$_2$), 2.77 (t, J=6.5 Hz, NHCH$_2$CH$_2$), 2.67 (s, NCH$_3$), 1.53-1.71 (m, CH$_2$CH$_2$CH$_2$CH$_3$), 1.39 (s, Boc), 1.12-1.28 (m, CH$_2$CH$_2$CH$_2$CH$_3$), 0.84 (s, CH$_2$CH$_2$CH$_2$CH$_3$).

Preparation Example 62: Preparation of (R)/(S)-tert-butyl methyl(1-oxo-1((2-(4'-(trifluoromethyl)-[1,1'-biphenyl]-4-yl)ethyl)amino)butan-2-yl)carbamate (67)

Compound 7 (0.62 g, 2.84 mmol), NMM (0.87 ml, 7.95 mmol), IBCF (0.48 ml, 3.69 mmol), and Compound 19 (0.90 g, 2.98 mmol) were reacted using Reaction Scheme e to synthesize Compound 67, (R)/(S)-tert-butyl methyl(1-oxo-1-((2-(4'-(trifluoromethyl)-[1,1'-biphenyl]-4-yl)ethyl)amino)butan-2-yl)carbamate (0.89 g, 67%) in the form of a white powder.

R$_f$=0.15 (EtOAc 1: n-hexane 3);
$^1$H NMR (CDCl$_3$, 400 MHz) 7.70 (t, J=9.7 Hz, ArH), 7.56 (d, J=7.9 Hz, ArH), 7.28-7.32 (m, ArH), 5.94-6.22 (m, C(O)NH), 4.45 (s, Chiral-H), 3.57-3.64 (m, NHCH$_2$CH$_2$), 2.89 (d, J=6.1 Hz, NHCH$_2$CH$_2$), 2.70 (s, NCH$_3$), 1.61-1.99 (m, CH$_2$CH$_3$), 1.45 (s, Boc), 0.89 (t, J=7.3 Hz, CH$_2$CH$_3$).

Preparation Example 63: Preparation of (R)/(S)-tert-butyl methyl(1-oxo-1((2-(4'-(trifluoromethyl)-[1,1'-biphenyl]-4-yl)ethyl)amino)pentan-2-yl)carbamate (68)

Compound 8 (0.58 g, 2.53 mmol), NMM (0.69 ml, 6.31 mmol), IBCF (0.43 ml, 3.28 mmol), and Compound 19 (0.80 g, 2.65 mmol) were reacted using Reaction Scheme e to synthesize Compound 68, (R)/(S)-tert-butyl methyl (1-oxo-1-(2-(4'-(trifluoromethyl)-[1,1'-biphenyl]-4-yl)ethyl)amino)pentan-2-yl)carbamate (1.19 g, 98%) in the form of an oil.

R$_f$=0.26 (EtOAc 1: n-hexane 3);
$^1$H NMR (CDCl$_3$, 300 MHz) 7.64-7.70 (m, ArH), 7.41 (dd, J=8.1 Hz, 67.4 Hz, ArH), 5.95-6.21 (s, C(O)NH), 4.52 (s, Chiral-H), 3.54-3.63 (m, NHCH$_2$CH$_2$), 2.86 (t, J=6.8 Hz, NHCH$_2$CH$_2$), 2.67 (s, NCH$_3$), 1.55-1.91 (m, CH$_2$CH$_2$CH$_3$), 1.42 (s, Boc), 1.23-1.27 (m, CH$_2$CH$_2$CH$_3$), 0.88-0.95 (m, CH$_2$CH$_2$CH$_3$).

Preparation Example 64: Preparation of (R)/(S)-tert-butyl methyl((1-oxo-1((2-(4'-(trifluoromethyl)-[1,1'-biphenyl]-4-yl)ethyl)amino)hexan-2-yl)carbamate (69)

Compound 9 (0.70 g, 2.84 mmol), NMM (0.87 ml, 7.95 mmol), IBCF (0.48 ml, 3.69 mmol), and Compound 19 (0.90 g, 2.98 mmol) were reacted using Reaction Scheme e to synthesize Compound 69, (R)/(S)-tert-butyl methyl(1-oxo-1-((2-(4'-(trifluoromethyl)-[1,1'-biphenyl]-4-yl)ethyl)amino)hexan-2-yl)carbamate (0.88 g, 63%) in the form of a yellow powder.

R$_f$=0.32 (EtOAc 1: n-hexane 3);
$^1$H NMR (DMSO-d$_6$, 400 MHz) 7.87 (d, J=8.3 Hz, ArH, C(O)NH), 7.80 (d, J=8.4 Hz, ArH), 7.66 (d, J=8.2 Hz, ArH), 7.33 (d, J=8.1 Hz, ArH), 4.27-4.47 (m, Chiral-H), 3.32-3.33 (m, NHCH$_2$CH$_2$), 2.78 (t, J=6.8 Hz, NHCH$_2$CH$_2$), 2.66 (s, NCH$_3$), 1.53-1.71 (m, CH$_2$CH$_2$CH$_2$CH$_3$), 1.39 (s, Boc), 1.12-1.28 (m, CH$_2$CH$_2$CH$_2$CH$_3$), 0.84-0.89 (m, CH$_2$CH$_2$CH$_2$CH$_3$).

Preparation Example 65: Preparation of (R)/(S)-tert-butyl methyl(1-oxo-1((2-(4'-(trifluoromethoxy)-[1,1'-biphenyl]-4-yl)ethyl)amino)butan-2-yl)carbamate (70)

Compound 7 (0.65 g, 3.00 mmol), NMM (0.92 ml, 8.99 mmol), IBCF (0.51 ml, 3.90 mmol), and Compound 20 (1.00 g, 3.15 mmol) were reacted using Reaction Scheme e to synthesize Compound 70, (R)/(S)-tert-butyl methyl (1-oxo-1-((2-(4'-(trifluoromethoxy)-[1,1'-biphenyl]-4-yl)ethyl)amino)butan-2-yl)carbamate (1.00 g, 69%) in the form of an oil.

R$_f$=0.19 (EtOAc 1: n-hexane 3);
$^1$H NMR (CDCl$_3$, 400 MHz) 7.51-7.70 (m, ArH), 7.29 (t, J=3.7 Hz, ArH), 5.98-6.26 (m, C(O)NH), 4.45 (s, Chiral-H), 3.59-3.60 (m, NHCH$_2$CH$_2$), 2.87 (s, NHCH$_2$CH$_2$), 2.70 (d, J=3.2 Hz, NCH$_3$), 1.62-2.07 (m, CH$_2$CH$_3$), 1.45 (s, Boc), 0.90 (m, CH$_2$CH$_3$).

Preparation Example 66: Preparation of (R)/(S)-tert-butyl methyl(1-oxo-1((2-(4'-(trifluoromethoxy)-[1,1'-biphenyl]-4-yl)ethyl)amino)pentan-2-yl)carbamate (71)

Compound 8 (0.25 g, 1.08 mmol), NMM (0.30 ml, 2.69 mmol), IBCF (0.18 ml, 1.40 mmol), and Compound 20 (0.36 g, 1.13 mmol) were reacted using Reaction Scheme e to synthesize Compound 71, (R)/(S)-tert-butyl methyl(1-oxo-1-(2-(4'-(trifluoromethoxy)-[1,1'-biphenyl]-4-yl)ethyl)amino)pentan-2-yl)carbamate (0.32 g, 60%) in the form of a white powder.

R$_f$=0.18 (EtOAc 1: n-hexane 3);
$^1$H NMR (DMSO-d$_6$, 400 MHz) 7.89 (s, C(O)NH), 7.76 (d, J=8.4 Hz, ArH), 7.59 (d, J=7.8 Hz, ArH), 7.44 (d, J=8.2 Hz, ArH), 7.30 (d, J=7.8 Hz, ArH), 4.30-4.49 (m, Chiral-H), 3.28-3.40 (m, NHCH$_2$CH$_2$), 2.77 (s, NHCH$_2$CH$_2$), 2.66 (s, NCH$_3$), 1.53-1.90 (m, CH$_2$CH$_2$CH$_3$), 1.39 (s, Boc), 1.16-1.23 (m, CH$_2$CH$_2$CH$_3$), 0.88-0.89 (m, CH$_2$CH$_2$CH$_3$)

Preparation Example 67: Preparation of (R)/(S)-tert-butyl methyl(1-oxo-1((2-(4'-(trifluoromethoxy)-[1,1'-biphenyl]-4-yl)ethyl)amino)hexan-2-yl)carbamate (72)

Compound 9 (0.74 g, 3.00 mmol), NMM (0.92 ml, 8.99 mmol), IBCF (0.51 ml, 3.90 mmol), and Compound 20 (1.00 g, 3.15 mmol) were reacted using Reaction Scheme e to synthesize Compound 72, (R)/(S)-tert-butyl methyl(1-oxo-1-((2-(4'-(trifluoromethoxy)-[1,1'-biphenyl]-4-yl)ethyl)amino)hexan-2-yl)carbamate (0.92 g, 60%) in the form of an oil.

R$_f$=0.29 (EtOAc 1: n-hexane 3);
$^1$H NMR (DMSO-d$_6$, 400 MHz) 7.88 (s, C(O)NH), 7.74-7.77 (m, ArH), 7.59 (d, J=8.2 Hz, ArH), 7.44 (d, J=8.0 Hz, ArH), 7.30 (d, J=8.1 Hz, ArH), 4.28-4.47 (m, Chiral-H), 3.30-3.34 (m, NHCH$_2$CH$_2$), 2.77 (t, J=6.7 Hz, NHCH$_2$CH$_2$), 2.66 (s, NCH$_3$), 1.53-1.72 (m, CH$_2$CH$_2$CH$_2$CH$_3$), 1.39 (s, Boc), 1.12-1.29 (m, CH$_2$CH$_2$CH$_2$CH$_3$), 0.84-0.90 (m, CH$_2$CH$_2$CH$_2$CH$_3$).

Preparation Example 68: Preparation of (R)/(S)-2-amino-N-(2-(3',4'-dichloro-[1,1'-biphenyl]-4-yl)ethyl)butanamide hydrochloride (73)

Compound 54 (0.66 g, 1.47 mmol) and 4.0 M HCl (2.20 ml, 8.81 mmol in dioxane) were reacted using Reaction Scheme f to synthesize Compound 73, (R)/(S)-2-amino-N-(2-(3',4'-dichloro-[1,1'-biphenyl]-4-yl)ethyl)butanamide hydrochloride (0.52 g, 91%) in the form of a white powder.
R$_f$=0.00 (EtOAc 9: acetone 1);
$^1$H NMR (DMSO-d$_6$, 400 MHz) 8.66 (t, J=5.3 Hz, C(O)NH), 8.23 (s, NH$_3$), 7.92 (d, J=1.9 Hz, ArH), 7.65-7.72 (m, ArH), 7.35 (d, J=8.1 Hz, ArH), 3.67 (t, J=6.0 Hz, Chiral-H), 3.31-3.55 (m, NHCH$_2$CH$_2$), 2.79-2.83 (m, NHCH$_2$CH$_2$), 1.67-1.74 (m, CH$_2$CH$_3$), 0.79 (t, J=7.4 Hz, CH$_2$CH$_3$).

Preparation Example 69: Preparation of (R)/(S)-2-amino-N-(2-(3',4'-dichloro-[1,1'-biphenyl]-4-yl)ethyl)pentanamide hydrochloride (74)

Compound 55 (0.95 g, 2.04 mmol) and 4.0 M HCl (3.06 ml, 12.2 mmol in dioxane) were reacted using Reaction Scheme f to synthesize Compound 74, (R)/(S)-2-amino-N-(2-(3',4'-dichloro-[1,1'-biphenyl]-4-yl)ethyl)pentanamide hydrochloride (0.66 g, 80%) in the form of a yellow powder.
R$_f$=0.00 (EtOAc 9: acetone 1);
$^1$H NMR (DMSO-d$_6$, 400 MHz) 8.82 (t, J=5.3 Hz, C(O)NH), 8.34 (s, NH$_3$), 7.64-7.90 (m, ArH), 7.35-7.38 (d, J=8.1 Hz, ArH), 3.73 (t, J=6.3 Hz, Chiral-H), 3.29-3.57 (m, NHCH$_2$CH$_2$), 2.82-2.85 (m, NHCH$_2$CH$_2$), 1.60-1.67 (m, CH$_2$CH$_2$CH$_3$), 1.14-1.22 (m, CH$_2$CH$_2$CH$_3$), 0.80 (t, J=7.1 Hz, CH$_2$CH$_2$CH$_3$).

Preparation Example 70: Preparation of (R)/(S)-2-amino-N-(2-(3',4'-dichloro-[1,1'-biphenyl]-4-yl)ethyl)hexanamide hydrochloride (75)

Compound 56 (0.75 g, 1.56 mmol) and 4.0 M HCl (2.35 ml, 9.39 mmol in dioxane) were reacted using Reaction Scheme f to synthesize Compound 75, (R)/(S)-2-amino-N-(2-(3',4'-dichloro-[1,1'-biphenyl]-4-yl)ethyl)hexanamide hydrochloride (0.60 g, 92%) in the form of a white powder.
R$_f$=0.00 (EtOAc 9: acetone 1);
$^1$H NMR (DMSO-d$_6$, 400 MHz) 8.60 (t, J=5.5 Hz, C(O)NH), 8.18 (s, NH$_3$), 7.91 (d, J=2.0 Hz, ArH), 7.65-7.72 (m, ArH), 7.35 (d, J=8.2 Hz, ArH), 3.66 (t, J=6.2 Hz, Chiral-H), 3.28-3.58 (m, NHCH$_2$CH$_2$), 2.81-2.85 (m, NHCH$_2$CH$_2$), 1.59-1.64 (m, CH$_2$CH$_2$CH$_3$), 1.14-1.23 (m, CH$_2$CH$_2$CH$_3$), 0.79 (t, J=6.8 Hz, CH$_2$CH$_2$CH$_3$).

Preparation Example 71: Preparation of (R)/(S)-2-amino-N-(2-(4'-(trifluoromethyl)-[41,1'-biphenyl]-4-yl)ethyl)butanamide hydrochloride (76)

Compound 57 (0.90 g, 2.00 mmol) and 4.0 M HCl (3.00 ml, 12.0 mmol in dioxane) were reacted using Reaction Scheme f to synthesize Compound 76, (R)/(S)-2-amino-N-(2-(4'-(trifluoromethyl)-[1,1'-biphenyl]-4-yl)ethyl)butanamide hydrochloride (0.75 g, 96%) in the form of a white powder.
R$_f$=0.00 (EtOAc 9: acetone 1);
$^1$H NMR (DMSO-d$_6$, 400 MHz) 8.62 (s, C(O)NH), 8.17 (s, NH$_3$), 7.88 (d, J=8.2 Hz, ArH), 7.81 (d, J=8.4 Hz, ArH), 7.68 (d, J=8.3 Hz, ArH), 7.38 (d, J=8.1 Hz, ArH), 3.66 (t, J=6.1 Hz, Chiral-H), 3.30-3.57 (m, NHCH$_2$CH$_2$), 2.82 (t, J=7.0 Hz, NHCH$_2$CH$_2$), 1.67-1.74 (m, CH$_2$CH$_3$), 0.79 (t, J=7.5 Hz, CH$_2$CH$_3$).

Preparation Example 72: Preparation of (R)/(S)-2-amino-N-(2-(4'-(trifluoromethyl)-[41,1'-biphenyl]-4-yl)ethyl)pentanamide hydrochloride (77)

Compound 58 (1.03 g, 2.22 mmol) and 4.0 M HCl (5.56 ml, 22.2 mmol in dioxane) were reacted using Reaction Scheme f to synthesize Compound 77, (R)/(S)-2-amino-N-(2-(4'-(trifluoromethyl)-[1,1'-biphenyl]-4-yl)ethyl)pentanamide hydrochloride (0.75 g, 85%) in the form of a white powder.
R$_f$=0.00 (EtOAc 9: acetone 1);
$^1$H NMR (DMSO-d$_6$, 300 MHz) 8.81 (t, J=5.3 Hz, C(O)NH), 8.35 (s, NH$_3$), 7.84 (dd, J=8.2 Hz, 15.7 Hz, ArH), 7.54 (dd, J=8.1 Hz, 73.4 Hz, ArH), 3.71-3.75 (t, J=6.3 Hz, Chiral-H), 3.30-3.60 (m, NH$_2$CH$_2$CH$_2$), 2.85 (t, J=6.3 Hz, NHCH$_2$CH$_2$), 1.61-1.68 (m, CH$_2$CH$_2$CH$_3$), 1.15-1.22 (m, CH$_2$CH$_2$CH$_3$), 0.80 (t, J=7.2 Hz, CH$_2$CH$_2$CH$_3$).

Preparation Example 73: Preparation of (R)/(S)-2-amino-N-(2-(4'-(trifluoromethyl)-[1,1'-biphenyl]-4-yl)ethyl)hexanamide hydrochloride (78)

Compound 59 (1.32 g, 2.76 mmol) and 4.0 M HCl (4.14 ml, 16.6 mmol in dioxane) were reacted using Reaction Scheme f to synthesize Compound 78, (R)/(S)-2-amino-N-(2-(4'-(trifluoromethyl)-[1,1'-biphenyl]-4-yl)ethyl)hexanamide hydrochloride (0.82 g, 72%) in the form of a white powder.
R$_f$=0.00 (EtOAc 9: acetone 1);
$^1$H NMR (DMSO-d$_6$, 400 MHz) 8.69 (t, J=4.9 Hz, C(O)NH), 8.26 (s, NH$_3$), 7.88 (d, J=8.2 Hz, ArH), 7.81 (d, J=8.3 Hz, ArH), 7.68 (d, J=8.1 Hz, ArH), 7.39 (d, J=8.0 Hz, ArH), 3.69 (t, J=6.2 Hz, Chiral-H), 3.29-3.59 (m, NHCH$_2$CH$_2$), 2.80-2.89 (m, NHCH$_2$CH$_2$), 1.61-1.67 (m, CH$_2$CH$_2$CH$_3$), 1.14-1.23 (m, CH$_2$CH$_2$CH$_2$CH$_3$), 0.79 (t, J=6.8 Hz, CH$_2$CH$_2$CH$_2$CH$_3$).

Preparation Example 74: Preparation of (R)/(S)-2-amino-N-(2-(4'-(trifluoromethoxy)-[1,1'-biphenyl]-4-yl)ethyl)butanamide hydrochloride (79)

Compound 60 (0.91 g, 1.95 mmol) and 4.0 M HCl (2.92 ml, 11.7 mmol in dioxane) were reacted using Reaction Scheme f to synthesize Compound 79, (R)/(S)-2-amino-N-(2-(4'-(trifluoromethoxy)[1,1'-biphenyl]-4-yl)ethyl)butanamide hydrochloride (0.43 g, 54%) in the form of a yellow powder.
R$_f$=0.00 (EtOAc 9: acetone 1);
$^1$H NMR (DMSO-d$_6$, 400 MHz) 8.67 (s, C(O)NH), 8.24 (s, NH$_3$), 7.35-7.89 (m, ArH), 3.67 (d, J=4.3 Hz, Chiral-H), 3.30-3.55 (m, NHCH$_2$CH$_2$), 2.80-2.85 (m, NHCH$_2$CH$_2$), 1.68-1.75 (m, CH$_2$CH$_3$), 0.80 (t, J=7.5 Hz, CH$_2$CH$_3$).

Preparation Example 75: Preparation of (R)/(S)-2-amino-N-(2-(4'-(trifluoromethoxy)-[1,1'-biphenyl]-4-yl)ethyl)pentanamide hydrochloride (80)

Compound 61 (0.70 g, 1.45 mmol) and 4.0 M HCl (2.18 ml, 8.70 mmol in dioxane) were reacted using Reaction Scheme f to synthesize Compound 80, (R)/(S)-2-amino-N-(2-(4'-(trifluoromethoxy)[1,1'-biphenyl]-4-yl)ethyl)pentanamide hydrochloride (0.55 g, 91%) in the form of a white powder.
R$_f$=0.00 (EtOAc 9: acetone 1);
$^1$H NMR (DMSO-d$_6$, 400 MHz) 8.71 (t, J=5.4 Hz, C(O)NH), 8.28 (s, NH$_3$), 7.77 (d, J=8.8 Hz, ArH), 7.62 (d, J=8.2 Hz, ArH), 7.35-7.45 (m, ArH), 3.70 (t, J=6.4 Hz, Chiral-H), 3.28-3.57 (m, NHCH$_2$CH$_2$), 2.80-2.86 (m, NHCH$_2$CH$_2$), 1.61-1.65 (m, CH$_2$CH$_2$CH$_3$), 1.13-1.24 (m, CH$_2$CH$_2$CH$_3$), 0.80 (t, J=7.4 Hz, CH$_2$CH$_2$CH$_3$).

Preparation Example 76: Preparation of (R)/(S)-2-amino-N-(2-(4'-(trifluoromethoxy)-[1,1'-biphenyl]-4-yl)ethyl)hexanamide hydrochloride (81)

Compound 62 (0.79 g, 1.59 mmol) and 4.0 M HCl (2.38 ml, 9.54 mmol in dioxane) were reacted using Reaction Scheme f to synthesize Compound 81, (R)/(S)-2-amino-N-(2-(4'-(trifluoromethoxy)-[1,1'-biphenyl]-4-yl)ethy)phexanamide hydrochloride (0.62 g, 91%) in the form of a white powder.

$R_f$=0.00 (EtOAc 9: acetone 1);
$^1$H NMR (DMSO-$d_6$, 400 MHz) 8.66 (t, J=5.4 Hz, C(O)NH), 8.23 (s, NH$_3$), 7.88 (d, J=8.2 Hz, ArH), 7.81 (d, J=8.4 Hz, ArH), 7.68 (d, J=8.2 Hz, ArH), 7.39 (d, J=8.2 Hz, ArH), 3.68 (t, J=6.4 Hz, Chiral-H), 3.29-3.59 (m, NHCH$_2$CH$_2$), 2.81-2.87 (m, NHCH$_2$CH$_2$), 1.60-1.66 (m, CH$_2$CH$_2$CH$_2$CH$_3$), 1.13-1.23 (m, CH$_2$CH$_2$CH$_2$CH$_3$), 0.79 (t, J=7.0 Hz, CH$_2$CH$_2$CH$_2$CH$_3$).

Preparation Example 77: Preparation of (R)/(S)-2-amino-N-(2-(3',4'-difluoro-[1,1'-biphenyl]-4-yl)ethyl)pentanamide hydrochloride (82)

Compound 62 (0.94 g, 2.17 mmol) and 4.0 M HCl (3.26 ml, 13.0 mmol in dioxane) were reacted using Reaction Scheme f to synthesize Compound 82, (R)/(S)-2-amino-N-(2-(3',4'-difluoro-[1,1'-biphenyl]-4-yl)ethyl)pentanamide hydrochloride (0.68 g, 85%) in the form of a white powder.

$R_f$=0.00 (EtOAc 9: acetone 1);
$^1$H NMR (DMSO-$d_6$, 400 MHz) 8.55 (s, C(O)NH), 8.10 (s, NH$_3$), 7.72-7.77 (m, ArH), 7.62 (d, J=8.1 Hz, ArH), 7.50-7.53 (m, ArH), 7.33 (d, J=8.1 Hz, ArH), 3.65 (t, J=5.9 Hz, Chiral-H), 3.29-3.57 (m, NHCH$_2$CH$_2$), 2.78-2.84 (m, NHCH$_2$CH$_2$), 1.58 (q, J=6.9 Hz, 8.8 Hz, CH$_2$CH$_2$CH$_3$), 1.14-1.20 (m, CH$_2$CH$_2$CH$_3$), 0.80 (t, J=7.3 Hz, CH$_2$CH$_2$CH$_3$).

Preparation Example 78: Preparation of (R)/(S)-N-(2-(3',4'-dichloro-[1,1'-biphenyl]-4-yl)ethyl)-2-(methylamino)butanamide hydrochloride (83)

Compound 64 (1.31 g, 2.81 mmol) and 4.0 M HCl (4.20 ml, 16.9 mmol in dioxane) were reacted using Reaction Scheme f to synthesize Compound 83, (R)/(S)-N-(2-(3',4'-dichloro-[1,1'-biphenyl]-4-yl)ethyl)-2-(methylamino)butanamide hydrochloride (1.07 g, 94%) in the form of a yellow powder.

$R_f$=0.00 (EtOAc 9: acetone 1);
$^1$H NMR (DMSO-$d_6$, 400 MHz) 8.79 (s, C(O)NH, NH$_2$), 7.92 (d, J=2.0 Hz, ArH), 7.65-7.72 (m, ArH), 7.36 (d, J=8.1 Hz, ArH), 3.59 (t, J=6.4 Hz, Chiral-H), 3.39-3.53 (m, NHCH$_2$CH$_2$), 2.83 (t, J=6.8 Hz, NHCH$_2$CH$_2$), 2.38 (t, J=6.1 Hz, NCH$_3$), 1.68-1.80 (m, CH$_2$CH$_3$), 0.77 (t, J=7.5 Hz, CH$_2$CH$_3$).

Preparation Example 79: Preparation of (R)/(S)-N-(2-(3',4'-dichloro-[1,1'-biphenyl]-4-yl)ethyl)-2-(methylamino)pentanamide hydrochloride (84)

Compound 65 (0.65 g, 1.36 mmol) and 4.0 M HCl (2.03 ml, 8.13 mmol in dioxane) were reacted using Reaction Scheme f to synthesize Compound 84, (R)/(S)-N-(2-(3',4'-dichloro-[1,1'-biphenyl]-4-yl)ethyl)-2-(methylamino)pentanamide hydrochloride (0.33 g, 57%) in the form of a yellow powder.

$R_f$=0.00 (EtOAc 9: acetone 1);
$^1$H NMR (DMSO-$d_6$, 400 MHz) 9.26 (s, NH$_2$), 8.96 (t, J=5.3 Hz, C(O)NH), 7.90-7.91 (m, ArH), 7.64-7.71 (m, ArH), 7.36 (d, J=8.1 Hz, ArH), 3.64-3.68 (m, Chiral-H), 3.42-3.56 (m, NHCH$_2$CH$_2$), 2.84 (t, J=6.8 Hz, NHCH$_2$CH$_2$), 2.35 (s, NCH$_3$), 1.60-1.77 (m, CH$_2$CH$_2$CH$_3$), 1.09-1.16 (m, CH$_2$CH$_2$CH$_3$), 0.80 (t, J=7.2 Hz, CH$_2$CH$_2$CH$_3$).

Preparation Example 80: Preparation of (R)/(S)-N-(2-(3',4'-dichloro-[1,1'-biphenyl]-4-yl)ethyl)-2-(methylamino)hexanamide hydrochloride (85)

Compound 66 (0.57 g, 1.16 mmol) and 4.0 M HCl (1.74 ml, 6.95 mmol in dioxane) were reacted using Reaction Scheme f to synthesize Compound 85, (R)/(S)-N-(2-(3',4'-dichloro-[1,1'-biphenyl]-4-yl)ethyl)-2-(methylamino)hexanamide hydrochloride (0.38 g, 75%) in the form of a white powder.

$R_f$=0.00 (EtOAc 9: acetone 1);
$^1$H NMR (DMSO-$d_6$, 400 MHz) 8.70-9.36 (s, NH$_2$), 8.80 (t, J=5.4 Hz, C(O)NH), 7.91 (d, J=2.0 Hz, ArH), 7.65-7.72 (m, ArH), 7.35 (d, J=8.2 Hz, ArH), 3.55 (t, J=6.6 Hz, Chiral-H), 3.38-3.52 (m, NHCH$_2$CH$_2$), 2.83 (t, J=6.8 Hz, NHCH$_2$CH$_2$), 2.35 (s, NCH$_3$), 1.60-1.76 (m, CH$_2$CH$_2$CH$_3$), 1.05-1.23 (m, CH$_2$CH$_2$CH$_3$), 0.78 (t, J=7.2 Hz, CH$_2$CH$_2$CH$_3$).

Preparation Example 81: Preparation of (R)/(S)-2-(methylamino)-N-(2-(4'-(trifluoromethyl)-[1,1'-biphenyl]-4-yl)ethyl)butanamide hydrochloride (86)

Compound 67 (0.86 g, 1.84 mmol) and 4.0 M HCl (2.77 ml, 11.1 mmol in dioxane) were reacted using Reaction Scheme f to synthesize Compound 86, (R)/(S)-2-(methylamino)-N-(2-(4'-(trifluoromethyl)-[1,1'-biphenyl]-4-yl)ethyl)butanamide hydrochloride (0.65 g, 88%) in the form of a white powder.

$R_f$=0.00 (EtOAc 9: acetone 1);
$^1$H NMR (DMSO-$d_6$, 400 MHz) 9.04 (s, NH$_2$), 8.79 (s, C(O)NH), 7.87 (d, J=8.3 Hz, ArH), 7.80 (d, J=8.4 Hz, ArH), 7.68 (d, J=8.2 Hz, ArH), 7.39 (d, J=8.2 Hz, ArH), 3.59 (t, J=2.5 Hz, 4.9 Hz, Chiral-H), 3.40-3.56 (m, NHCH$_2$CH$_2$), 2.84 (t, J=6.9 Hz, NHCH$_2$CH$_2$), 2.37 (s, NCH$_3$), 1.67-1.85 (m, CH$_2$CH$_3$), 0.77 (t, J=7.5 Hz, CH$_2$CH$_3$).

Preparation Example 82: Preparation of (R)/(S)-2-(methylamino)-N-(2-(4'-(trifluoromethyl)-[1,1'-biphenyl]-4-yl)ethyl)pentanamide hydrochloride (87)

Compound 68 (1.17 g, 2.45 mmol) and 4.0 M HCl (3.67 ml, 14.7 mmol in dioxane) were reacted using Reaction Scheme f to synthesize Compound 87, (R)/(S)-2-(methylamino)-N-(2-(4'-(trifluoromethyl)-[1,1'-biphenyl]-4-yl)ethyl)pentanamide hydrochloride (81%) in the form of a white powder.

$R_f$=0.00 (EtOAc 9: acetone 1);
$^1$H NMR (DMSO-$d_6$, 400 MHz) 8.93-9.79 (m, NH$_2$), 9.04 (t, J=5.2 Hz, C(O)NH), 7.84 (dd, J=8.3 Hz, 15.1 Hz, ArH), 7.54 (dd, J=8.0 Hz, 73.4 Hz, ArH), 3.68-3.72 (m, Chiral-H), 3.42-3.58 (m, NHCH$_2$CH$_2$), 2.87 (t, J=6.7 Hz, NHCH$_2$CH$_2$), 2.36 (s, NCH$_3$), 1.64-1.82 (m, CH$_2$CH$_2$CH$_3$), 1.09-1.22 (m, CH$_2$CH$_2$CH$_3$), 0.81 (t, J=7.1 Hz, CH$_2$CH$_2$CH$_3$).

Preparation Example 83: Preparation of (R)/(S)-2-(methylamino)-N-(2-(4'-(trifluoromethyl)-[1,1'-biphenyl]-4-yl)ethyl)hexanamide hydrochloride (88)

Compound 69 (0.85 g, 1.72 mmol) and 4.0 M HCl (2.60 ml, 10.3 mmol in dioxane) were reacted using Reaction Scheme f to synthesize Compound 88, (R)/(S)-2-(methylamino)-N-(2-(4'-(trifluoromethyl)-[1,1'-biphenyl]-4-yl)ethyl)hexanamide hydrochloride (0.53 g, 71%) in the form of a white powder.

$R_f$=0.00 (EtOAc 9: acetone 1);

$^1$H NMR (DMSO-$d_6$, 400 MHz) 9.00 (s, $NH_2$), 8.75 (t, J=5.4 Hz, C(O)NH), 7.87 (d, J=8.3 Hz, ArH), 7.81 (d, J=8.4 Hz, ArH), 7.68 (d, J=8.2 Hz, ArH), 7.38 (d, J=8.2 Hz, ArH), 3.57-3.61 (m, Chiral-H), 3.40-3.55 (m, $NHCH_2CH_2$), 2.84 (t, J=6.8 Hz, $NHCH_2CH_2$), 2.36 (s, $NCH_3$), 1.60-1.75 (m, $CH_2CH_2CH_2CH_3$), 1.06-1.24 (m, $CH_2CH_2CH_2CH_3$), 0.78 (t, J=7.2 Hz, $CH_2CH_2CH_2CH_3$).

Preparation Example 84: Preparation of (R)/(S)-2-(methylamino)-N-(2-(4'-(trifluoromethoxy)-[1,1'-biphenyl]-4-yl)ethyl)butanamide hydrochloride (89)

Compound 70 (0.97 g, 2.01 mmol) and 4.0 M HCl (3.00 ml, 12.1 mmol in dioxane) were reacted using Reaction Scheme f to synthesize Compound 89, (R)/(S)-2-(methylamino)-N-(2-(4'-(trifluoromethoxy)-[1,1'-biphenyl]-4-yl)ethyl)butanamide hydrochloride (0.73 g, 88%) in the form of a yellow powder.

$R_f$=0.00 (EtOAc 9: acetone 1);

$^1$H NMR (DMSO-$d_6$, 400 MHz) 9.00 (s, $NH_2$), 8.77 (s, C(O)NH), 7.77 (d, J=8.7 Hz, ArH), 7.61 (d, J=8.2 Hz, ArH), 7.44 (d, J=8.2 Hz, ArH), 7.35 (d, J=8.1 Hz, ArH), 3.57-3.60 (m, Chiral-H), 3.39-3.55 (m, $NHCH_2CH_2$), 2.82 (t, J=6.9 Hz, $NHCH_2CH_2$), 2.37 (s, $NCH_3$), 1.67-1.83 (m, $CH_2CH_3$), 0.77 (t, J=7.5 Hz, $CH_2CH_3$).

Preparation Example 85: Preparation of (R)/(S)-2-(methylamino)-N-(2-(4'-(trifluoromethoxy)-[1,1'-biphenyl]-4-yl)ethyl)pentanamide hydrochloride (90)

Compound 71 (0.83 g, 1.67 mmol) and 4.0 M HCl (2.51 ml, 10.0 mmol in dioxane) were reacted using Reaction Scheme f to synthesize Compound 90, (R)/(S)-2-(methylamino)-N-(2-(4'-(trifluoromethoxy)-[1,1'-biphenyl]-4-yl)ethyl)pentanamide hydrochloride (0.40 g, 61%) in the form of a white powder.

$R_f$=0.00 (EtOAc 9: acetone 1);

$^1$H NMR (DMSO-$d_6$, 400 MHz) 8.85-9.19 (m, $NH_2$), 8.75 (s, C(O)NH), 7.76 (d, J=7.7 Hz, ArH), 7.61 (d, J=7.5 Hz, ArH), 7.44 (d, J=8.0 Hz, ArH), 7.35 (d, J=7.4 Hz, ArH), 3.60 (s, Chiral-H), 3.40-3.56 (m, $NHCH_2CH_2$), 2.83 (t, J=6.5 Hz, $NHCH_2CH_2$), 2.36 (s, $NCH_3$), 1.60-1.66 (m, $CH_2CH_2CH_3$), 1.09-1.17 (m, $CH_2CH_2CH_3$), 0.80 (t, J=7.0 Hz, $CH_2CH_2CH_3$).

Preparation Example 86: Preparation of (R)/(S)-2-(methylamino)-N-(2-(4'-(trifluoromethoxy)-[1,1'-biphenyl]-4-yl)ethyl)hexanamide hydrochloride (91)

Compound 72 (0.89 g, 1.74 mmol) and 4.0 M HCl (2.61 ml, 10.4 mmol in dioxane) were reacted using Reaction Scheme f to synthesize Compound 91, (R)/(S)-2-(methylamino)-N-(2-(4'-(trifluoromethoxy)-[1,1'-biphenyl]-4-yl)ethyl)hexanamide hydrochloride (0.66 g, 86%) in the form of a white powder.

$R_f$=0.00 (EtOAc 9: acetone 1);

$^1$H NMR (DMSO-$d_6$, 400 MHz) 8.95 (s, $NH_2$), 8.72 (s, C(O)NH), 7.76 (d, J=8.7 Hz, ArH), 7.61 (d, J=8.1 Hz, ArH), 7.44 (d, J=8.4 Hz, ArH), 7.35 (d, J=8.1 Hz, ArH), 3.57-3.60 (m, Chiral-H), 3.29-3.56 (m, $NHCH_2CH_2$), 2.83 (t, J=6.8 Hz, $NHCH_2CH_2$), 2.37 (s, $NCH_3$), 1.59-1.74 (m, $CH_2CH_2CH_2CH_3$), 1.08-1.24 (m, $CH_2CH_2CH_2CH_3$), 0.78 (t, J=7.2 Hz, $CH_2CH_2CH_2CH_3$).

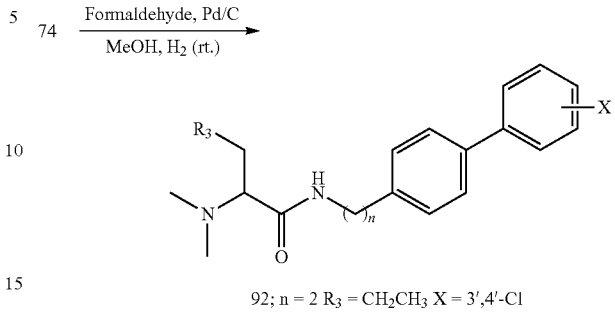

92; n = 2 $R_3$ = $CH_2CH_3$ X = 3',4'-Cl

Preparation Example 87: Preparation of (R)/(S)-N-(2-(3',4'-dichloro-[1,1'-biphenyl]-4-yl)ethyl)-2-(dimethylamino)pentanamide (92)

Compound 74 (1.0 eq), triethylamine (6.0 eq), formaldehyde (1.05 eq), and a palladium catalyst (0.2 eq) were reacted using Reaction Scheme g to synthesize Compound 92, (R)/(S)-N-(2-(3',4'-dichloro-[1,1'-biphenyl]-4-yl)ethyl)-2-(dimethylamino)pentanamide.

$^1$H NMR (DMSO-$d_6$, 400 MHz) 8.96 (t, J=5.3 Hz, C(O)NH), 7.90-7.91 (m, ArH), 7.64-7.71 (m, ArH), 7.36 (d, J=8.1 Hz, ArH), 3.64-3.68 (m, Chiral-H), 3.42-3.56 (m, $NHCH_2CH_2$), 2.82-2.85 (m, $NHCH_2CH_2$), 2.35 (s, $N(CH_3)_2$), 1.60-1.77 (m, $CH_2CH_2CH_3$), 1.09-1.16 (m, $CH_2CH_2CH_3$), 0.80 (t, J=7.2 Hz, $CH_2CH_2CH_3$).

EXAMPLES

Example 1: Analysis of antifungal activity against human pathogenic fungi

An in vitro antifungal susceptibility test was performed in accordance with the US Clinical and Laboratory Standards Institute (CLSI) guidelines to measure the degree of antifungal activity of the compounds synthesized in the Preparation Examples against opportunistic pathogenic fungi. In the present example, the minimum inhibitory concentrations (MICs) at which the compounds can inhibit the growth of fungi for pathogenic fungi *Cryptococcus neoformans*, *Candida albicans*, *Candida glabrata*, and *Aspergillus* fumigatus were determined, and are shown in Table 1. The MIC value (μg/mℓ) is expressed as a range value. Specifically, *Candida* species and *Cryptococcus* neoformans were incubated in a Sabouraud dextrose agar (SDA) (Sigma-Aldrich) solid medium for 24 and 48 hours, respectively to obtain single colonies. The obtained single colonies were suspended in 0.85% physiological saline to prepare fungal cell suspension (1 to 5×10$^6$ cells/mℓ). Fungal cells 2000-fold diluted in RPMI1640 broth (Sigma-Aldrich) were seeded on 96-well plates (5×10$^2$ to 2.5×10$^3$ cells/mℓ, 195 μℓ/well). Serial two-fold dilutions (128, 64, 32, 16, 8, 4, 2, 1, and 0.5 μg/mℓ) of compounds were prepared by diluting the compounds synthesized according to the above preparation examples. Then, 5 from each dilution was added to the well of the 96-well plate containing fungal cell suspension to give a final suspension of 200 μℓ per well. The compound-treated *Candida* species and *C. neoformans* were incubated at 35° C. for 48 hours and for 72 hours, respectively, and then MICs were determined by visually observing the bottom of the 96-well plate to confirm whether the fungi were developed and grown. As a positive control, amphotericin B (AMB), which is highly toxic to the human body but is known as a representative antifungal agent, was used. The results are shown in Tables 1 to 3.

TABLE 1

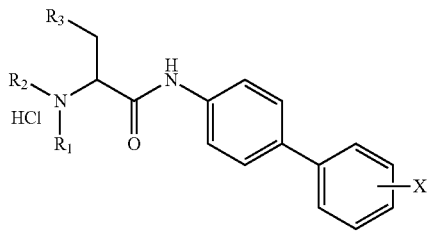

| Preparation example # (compound #) | R1 | R2 | R3 | X | MIC (μg/mL) | | | |
|---|---|---|---|---|---|---|---|---|
| | | | | | C. neoformans | C. albicans | C. glabrata | A. fumigatus |
| 24 (29) | H | H | CH₃ | 3,4-Cl | 2~8 | 4~16 | 4~16 | 4~16 |
| 25 (30) | H | H | CH₂CH₃ | 3,4-Cl | 2~8 | 4~16 | 4~16 | 4~16 |
| 26 (31) | H | H | CH₂CH₂CH₃ | 3,4-Cl | 0.5~4 | 0.5~4 | 0.5~4 | 0.5~4 |
| 27 (32) | H | H | CH₂CH₃ | 4-OCF₃ | 2~8 | 4~16 | 4~16 | 4~16 |
| 28 (33) | H | CH₃ | CH₃ | 3,4-Cl | 4~16 | 8~32 | 8~32 | 8~32 |
| 29 (34) | H | CH₃ | CH₂CH₃ | 3,4-Cl | 2~8 | 4~16 | 8~32 | 8~32 |
| 30 (35) | H | CH₃ | CH₂CH₂CH₃ | 3,4-Cl | 0.5~4 | 0.5~4 | 0.5~4 | 0.5~4 |
| 31 (36) | CH₃ | CH₃ | CH₂CH₃ | 3,4-Cl | 2~8 | 4~16 | 4~16 | 4~16 |

TABLE 2

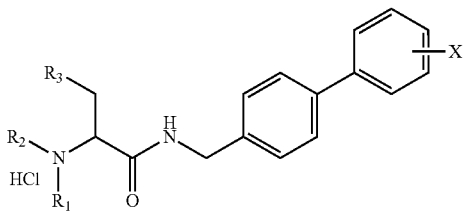

| Preparation example # (compound #) | R1 | R2 | R3 | X | MIC (μg/mL) | | | |
|---|---|---|---|---|---|---|---|---|
| | | | | | C. neoformans | C. albicans | C. glabrata | A. fumigatus |
| 40 (45) | H | H | CH₂CH₃ | 3,4-Cl | 2~8 | 8~32 | 8~32 | 8~32 |
| 41 (46) | H | H | CH₂CH₂CH₃ | 3,4-Cl | 0.5~4 | 2~8 | 2~8 | 2~8 |
| 42 (47) | H | H | CH₂CH₃ | 4-CF₃ | 4~16 | 8~32 | 8~32 | 8~32 |
| 43 (48) | H | H | CH₂CH₂CH₃ | 4-CF₃ | 4~16 | 4~16 | 4~16 | 4~16 |
| 44 (49) | H | H | CH₂CH₃ | 4-OCF₃ | 4~16 | 8~32 | 8~32 | 8~32 |
| 45 (50) | H | H | CH₂CH₂CH₃ | 4-OCF₃ | 4~16 | 4~16 | 4~16 | 4~16 |
| 46 (51) | H | CH₃ | CH₂CH₃ | 3,4-Cl | 2~8 | 4~16 | 4~16 | 4~16 |
| 47 (52) | H | CH₃ | CH₂CH₃ | 4-CF₃ | 4~16 | 8~32 | 8~32 | 8~32 |
| 48 (53) | CH₃ | CH₃ | CH₂CH₃ | 3,4-Cl | 2~8 | 8~32 | 8~32 | 8~32 |

TABLE 3

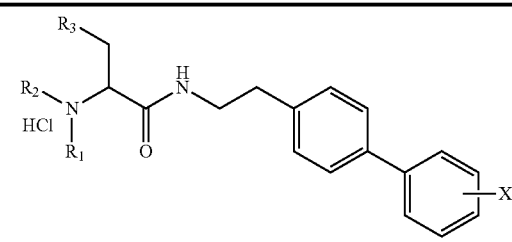

| Preparation example # (compound #) | R1 | R2 | R3 | X | MIC (μg/mL) | | | |
|---|---|---|---|---|---|---|---|---|
| | | | | | C. neoformans | C. albicans | C. glabrata | A. fumigatus |
| 68 (73) | H | H | CH₃ | 3,4-Cl | 2~8 | 8~32 | 8~32 | 8~32 |
| 69 (74) | H | H | CH₂CH₃ | 3,4-Cl | 0.5~4 | 0.5~4 | 0.5~4 | 0.5~4 |
| 70 (75) | H | H | CH₂CH₂CH₃ | 3,4-Cl | 0.5~4 | 0.5~4 | 0.5~4 | 0.5~4 |

TABLE 3-continued

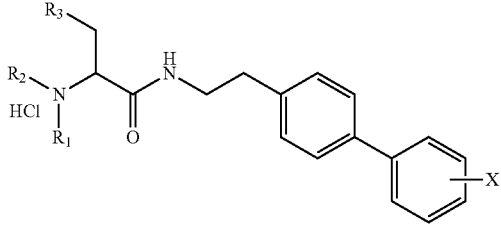

| Preparation example # (compound #) | R1 | R2 | R3 | X | MIC (μg/mL) | | | |
|---|---|---|---|---|---|---|---|---|
| | | | | | C. neoformans | C. albicans | C. glabrata | A. fumigatus |
| 71 (76) | H | H | $CH_3$ | 4-$CF_3$ | 8~32 | 16~64 | 8~32 | 8~32 |
| 72 (77) | H | H | $CH_2CH_3$ | 4-$CF_3$ | 4~16 | 8~32 | 8~32 | 8~32 |
| 73 (78) | H | H | $CH_2CH_2CH_3$ | 4-$CF_3$ | 2~8 | 4~16 | 4~16 | 4~16 |
| 74 (79) | H | H | $CH_3$ | 4-$OCF_3$ | 8~32 | 8~32 | 8~32 | 8~32 |
| 75 (80) | H | H | $CH_2CH_3$ | 4-$OCF_3$ | 2~8 | 4~16 | 4~16 | 4~16 |
| 76 (81) | H | H | $CH_2CH_2CH_3$ | 4-$OCF_3$ | 2~8 | 2~8 | 2~8 | 2~8 |
| 77 (82) | H | H | $CH_2CH_3$ | 3,4-F | 4~16 | 4~16 | 4~16 | 4~16 |
| 78 (83) | H | $CH_3$ | $CH_3$ | 3,4-Cl | 2~8 | 8~32 | 8~32 | 8~32 |
| 79 (84) | H | $CH_3$ | $CH_2CH_3$ | 3,4-Cl | 2~8 | 4~1 | 4~1 | 4~1 |
| 80 (85) | H | $CH_3$ | $CH_2CH_2CH_3$ | 3,4-Cl | 0.5~4 | 0.5~4 | 0.5~4 | 0.5~4 |
| 81 (86) | H | $CH_3$ | $CH_3$ | 4-$CF_3$ | 8~32 | 16~64 | 16~64 | 16~64 |
| 82 (87) | H | $CH_3$ | $CH_2CH_3$ | 4-$CF_3$ | 4~16 | 4~16 | 4~16 | 4~16 |
| 83 (88) | H | $CH_3$ | $CH_2CH_2CH_3$ | 4-$CF_3$ | 2~8 | 4~16 | 4~16 | 4~16 |
| 84 (89) | H | $CH_3$ | $CH_3$ | 4-$OCF_3$ | 8~32 | 8~32 | 8~32 | 8~32 |
| 85 (90) | H | $CH_3$ | $CH_2CH_3$ | 4-$OCF_3$ | 4~16 | 4~16 | 4~16 | 4~16 |
| 86 (91) | H | $CH_3$ | $CH_2CH_2CH_3$ | 4-$OCF_3$ | 2~8 | 4~16 | 4~16 | 4~16 |
| 87 (92) | $CH_3$ | $CH_3$ | $CH_3$ | 3,4-Cl | 4~16 | 8~32 | 8~32 | 8~32 |
| ABM | | | | | 0.25 | 0.25 | 0.5 | 1 |

Example 2: Analysis of antifungal activity for Compound 74

To evaluate the antifungal activity of Compound 74, the minimum inhibitory concentration (MIC) capable of inhibiting the growth of fungi was measured in accordance with the Clinical and Laboratory Standards Institute (CLSI) guidelines. Fungal cells were spread on YPD solid media (Sigma-Aldrich) and then aliquoted into the wells of the 96-well plates ($2.5 \times 10^3$ microconidia/mℓ for *T. rubrum* and *T. mentagrophytes* species or was $2.5 \times 10^3$ cfu/mℓ for *Candida albicans, Candida glabrata* and *Cryptococcus* neoformans species, 195 μl/well). Two-fold serial dilutions of the Compound 74, of which concentration are ranging from 128 to 0.5 μg/mℓ (128, 64, 32, 16, 8, 4, 2, 1 and 0.5 ℓg/mℓ), ware prepared. Next, 5 μl from each dilution of Compound 74 was added to the well of the 96-well plate including fungal cells to give a final suspension of 200 μℓ/well. The compound-treated fungal cells were incubated in a 35° C. incubator for 48 hours (*Candida* species) and for 72 hours (*C. neoformans* and *Trichophyton* species), respectively. After incubation, MICs (μg/mℓ) were determined by visually reading the bottom of the 96-well plate to detect fungal growth. The results are shown in Table 4.

TABLE 4

| Target Fungus | MIC (μg/mℓ) |
|---|---|
| *T. rubrum* (KCCM60443) | 1~4 |
| *T. rubrum* (KCCM60450) | 2~4 |
| *T. mentagrophytes* (KCCM60449) | 2~8 |
| *C. albicans* ATCC90028 (WT), n = 30 | 2~4 |
| *C. albicans* 12-99 (Mutant) | 2~8 |
| *C. glabrata*, n = 30 | 2~4 |
| *C. tropicalis* | 2~4 |
| *C. neoformans*, n = 10 | 2~4 |
| *A. fumigatus* | 2~8 |

Example 3: Comparison of Fast-Acting Effects of Compound 74 with Commercially Available Comparators To evaluate fast-acting effects of Compound 74, the growth of *Candida albicans* was studied by treating *Candida albicans* with Compound 74 or commercially available drug of Efinaconazole, Tavaborole, Terbinafine, or Ciclopirox at the same concentration for the same period of time. Specifically, *Candida albicans* were prepared at a concentration of $2.5 \times 10^3$ cfu/mℓ and aliquoted at 195 μℓ/well into 96-well plates. Subsequently, *Candida albicans* cells in 96-well plate were treated with Compound 74 or each of the commercially available comparative drugs (50 μg/mℓ or 100 μg/mℓ) for 30 minutes, respectively. Next, Compound 74 treated fungal cells were seeded on YPD media (Sigma-Aldrich), and the number of single colonies grown was counted. The results are shown in FIG. 1. As shown in FIG. 1, it was confirmed that Compound 74 has an excellent fast-acting effects comparing to the commercially available competitive drugs.

Figure 2:
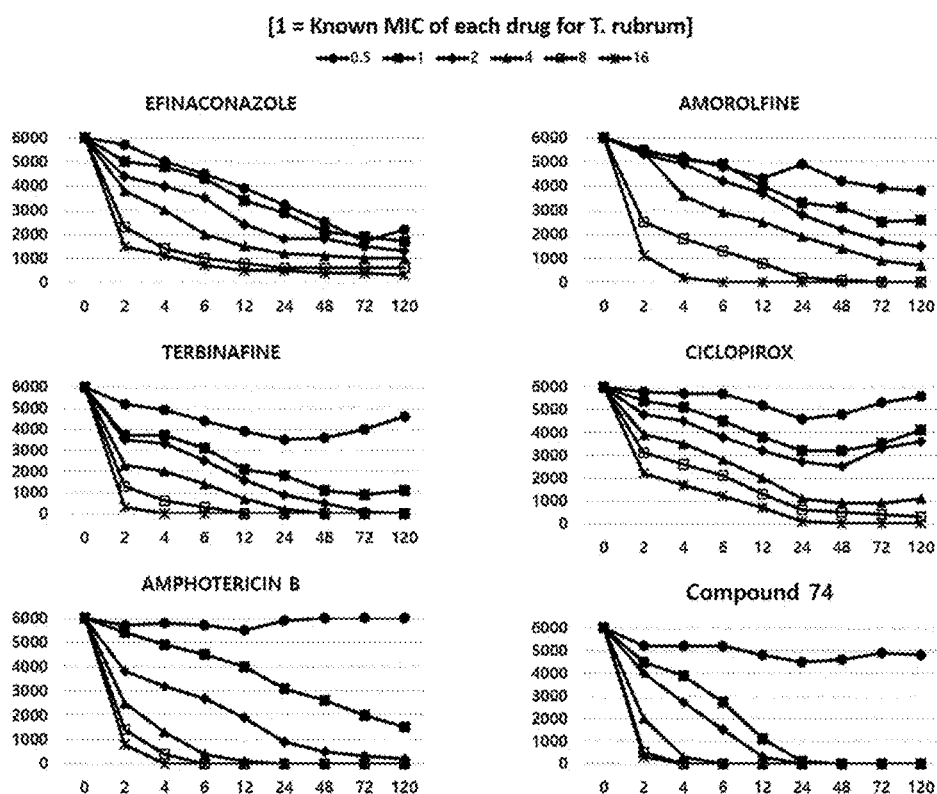
FIG. 2 compares the fungicidal activity of Compound 74 of the present invention with those of commercially available comparative drugs.

Example 4: Comparison of fungicidal effects of Compound 74 with commercially available competitive drugs To evaluate fungicidal effects of Compound 74, the growth of *T. rubrum* was studied after treating *T. rubrum* with Compound 74 or commercially available antifungal drug of Efinaconazole, Amorolfine, Terbinafine, Ciclopirox, or Amphotericin B (0.5, 1-, 2-, 4-, 8— or 16-fold of the respective MICs of Compound 74 or the other commercially available antifungal drugs) for a predetermined time. Specifically, *T. rubrum* cells (6×10³ cfu/m$\ell$) were prepared and aliquoted at 195 µ$\ell$/well into 96-well plates. Next, 5 of Compound 74 or each of the other commercially available drugs was added the well of the 96-well plate containing *T. rubrum* cells to give a final suspension of 200 µ$\ell$/well. 0, 2, 4, 6, 12, 24, 48, 72 or 120 hours after the addition, fungal cells treated with the Compound 74 or other antifungal drugs were spread on YPD solid media, and then the number of single colonies grown was counted. The results are illustrated in FIG. 2. As shown in FIG. 2, Compound 74 exhibited fungicidal effects at the MIC concentration, which suggests that Compound 74 has fungicidal effects at a lower concentration than other comparators.

Figure 3:
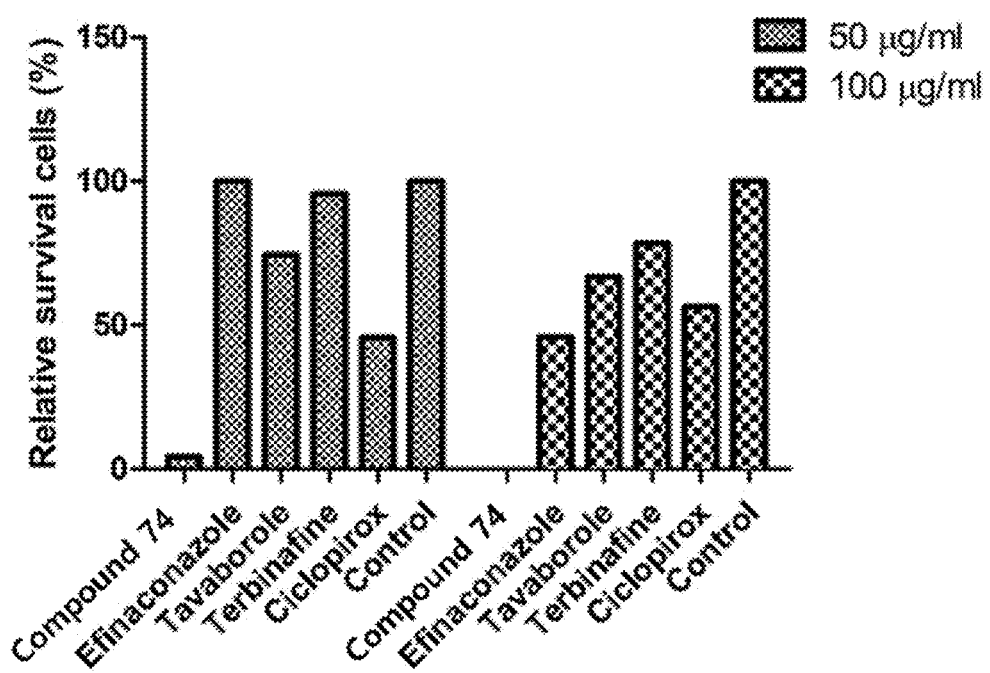
FIG. 3 compares the effect of removing a biofilm of Compound 74 of the present invention with those of commercially available comparative drugs.

Example 5: Comparison of biofilm disruption activities of Compound 74 with commercially available drugs The biofilm disruption activities of Compound 74 were studied. *Candida albicans* was allowed to form a biofilm. Next, Compound 74 or commercially available drug of Caspofungin, Amphotericin B or Efinaconazole was added to the obtained biofilm at respective concentrations of 4, 8, 16 and 32 µg/m$\ell$ to evaluate the disruption of the biofilm. Specifically, *Candida albicans* cells (2.5×10 3 cfu/m$\ell$) were seeded on a 96-well plate and incubated for 90 minutes to form a biofilm, and then the biofilm was treated with Compound 74 or each of the comparative drugs above, and then the growth of *Candida albicans* was studied 24 hours after the treatment. The results are presented in FIG. 3. As shown in FIG. 3, it was suggested that Compound 74 of the present invention exhibited remarkably excellent growth inhibitory effects on *Candida albicans* through biofilm disruption especially in comparison to those of the commercially available comparative drugs.

Example 6: Analysis of antibacterial activities

The antibacterial activities against Gram-positive bacteria, Gram-negative bacteria or multi-drug resistant bacteria were evaluated for the compounds of the present invention. The MIC test was conducted in accordance CLSI guidelines. *E. coli*(−), *P. aeruginosa*(−), and *S. enterica*(−) were used as Gram-negative bacteria, *B. cereus*(+), *B. subtilis*(+), *B. coagulans*(+), *L. monocytogenes*(+), *M. luteus*(+), *P. acnes*(+), *S. epidermidis*(+), and *S. aureus*(+) were used as Gram-positive bacteria. Methicillin-resistant *Staphylococcus aureus* (MRSA) was used as multi-drug resistant bacteria. The bacterial cells were incubated until the $OD_{600}$ of the single colonies reached 0.1. Cells diluted in 100-fold in a MHB liquid medium (Sigma-Aldrich) were seeded on 96-well plates to give a suspension of 100 µ$\ell$ per well with 0.001 $OD_{600}$. Next, two-fold serially diluted compounds of the present invention (64, 32, 16, 8, 4, 2, 1, and 0.5 µg/m$\ell$) were added to the wells to provide a final suspension of 200 µ$\ell$ well. Subsequently, bacterial cells were incubated at 37° C. for 24 hours, and then the MICs (µg/m$\ell$) were determined by visual reading and optical density detection at 600 nm ($OD_{600}$). As a positive control, Nofloxacin and Vancomycin were used. The results are shown in Tables 5 to 8.

TABLE 5

| Compound | B. cereus (+) | B. subtilis (+) | B. coagulans (+) |
|---|---|---|---|
| 74 | 16 | 8 | 2 |
| 84 | 32 | 16 | 8 |
| 51 | 32 | 16 | 4 |
| 75 | 16 | 8 | 2, 4 |
| 46 | 16 | 8 | 4 |
| 85 | 32 | 16 | 4 |
| 30 | 32 | 16 | 8 |
| 78 | 16 | <4 | <4 |
| 76 | 64 | 16 | <4 |
| 81 | 16 | 4 | <4 |
| 79 | 64 | 16 | <4 |
| 31 | <4 | <4 | <4 |
| 73 | 32 | 8 | <4 |
| 86 | 64 | 32 | <4 |
| 89 | >64 | 16 | <4 |
| 88 | >64 | 32 | <4 |
| 91 | 16 | 16 | <4 |
| 29 | 8 | <4 | <4 |
| 33 | 16 | 8 | <4 |
| 35 | <4 | <4 | <4 |
| 34 | 8 | <4 | <4 |
| Nofloxacin | 1 | <0.125 | <0.125 |
| Vancomycin | 0.5 | 0.25 | 0.25 |

TABLE 6

| Compound | E. coli (−) | S. aureus enterica (−) |
|---|---|---|
| 74 | 32 | >32 |
| 84 | >32 | >32 |
| 51 | >32 | >32 |
| 75 | 32 | >32 |
| 46 | 32 | 32 |
| 85 | >32 | >32 |
| 30 | >32 | >32 |
| 78 | 8 | 16 |
| 76 | 16 | 32 |
| 81 | 8 | 16 |
| 79 | 16 | 32 |
| 31 | <4 | 8 |
| 73 | 8 | 16 |
| 86 | 32 | 64 |
| 89 | 16 | 32 |
| 88 | 8 | >64 |
| 91 | 8 | 16 |
| 29 | 8 | 8 |
| 33 | 8 | 16 |
| 35 | <4 | 64 |
| 34 | 8 | 32 |
| Nofloxacin | <0.125 | <0.125 |
| Vancomycin | 64 | >64 |

TABLE 7

| Compound | L. monocytogenes (+) | M. luteus (+) | P. acnes (+) |
|---|---|---|---|
| 74 | 8 | 8 | 8 |
| 84 | 16 | 16 | 16 |
| 51 | 16 | 16 | 16 |
| 75 | 8 | 8 | 8 |
| 46 | 8 | 8 | 8 |
| 85 | 16 | 8 | 16 |
| 30 | 16 | 8, 16 | 16 |
| 78 | <4 | 8 | >64 |
| 76 | 16 | 16 | 16 |
| 81 | <4 | <4 | 8 |
| 79 | 16 | 16 | 16 |
| 31 | <4 | <4 | <4 |
| 73 | 8 | 8 | 8 |
| 86 | 16 | 16 | 16 |
| 89 | 16 | 16 | 16 |
| 88 | <4 | >64 | <4 |
| 91 | <4 | <4 | <4 |

TABLE 7-continued

| Compound | L. monocytogenes (+) | M. luteus (+) | P. acnes (+) |
|---|---|---|---|
| 29 | <4 | <4 | <4 |
| 33 | <4 | <4 | <4 |
| 35 | >64 | <4 | <4 |
| 34 | <4 | <4 | <4 |
| Nofloxacin | <0.125 | <0.125 | <0.125 |
| Vancomycin | 0.25 | 0.25 | <0.125 |

TABLE 8

| Compound | S. epidermidis (+) | S. aureus (+) | MRSA |
|---|---|---|---|
| 74 | 8 | 8 | 8 |
| 84 | 16 | 16 | 16 |
| 51 | 16 | 16 | 16 |
| 75 | 8 | 8 | 8 |
| 46 | 8 | 8 | 8 |
| 85 | 16 | 16 | 16 |
| 30 | 16 | 16 | 16 |
| 78 | 8 | 8 | 8 |
| 76 | 16 | 32 | 32 |
| 81 | 8 | 8 | 8 |
| 79 | 8 | 16 | 16 |
| 31 | <4 | <4 | <4 |
| 73 | 8 | 8 | 8 |
| 86 | 16 | 32 | 32 |
| 89 | 16 | 32 | 32 |
| 88 | 8 | 8 | 8 |
| 91 | <4 | 8 | 8 |
| 29 | <4 | <4 | <4 |
| 33 | <4 | 8 | <4 |
| 35 | <4 | 8 | <4 |
| 34 | <4 | <4 | <4 |
| Nofloxacin | | | 0.5 |
| Vancomycin | | | 1 |

Example 7: Analysis of Anti-Inflammatory Activities

The anti-inflammatory effects of the compounds of the present invention were evaluated using RAW264.7 cells which were stimulated to secrete interleukin 6 (IL-6). Specifically, RAW264.7 cells (obtained from Korean Cell Line Bank), mouse macrophages, were inoculated into a 12-well plate at 5×10$^5$ cells/well and incubated at 37° C. for 16 to 24 hours. The compounds of the present invention were added to the cell culture medium containing RAW264.7 cells incubated as above at a final concentration of 0 or 8 μg/mℓ, and then incubated at 37° C. for 1 hour. Next, lipopolysaccharide (LPS, Sigma-Aldrich, USA) was further added to the medium at a final concentration of 1 μg/mℓ, and the medium was incubated at 37° C. for 24 hours to induce IL-6 expression. Thereafter, IL-6 levels produced by the RAW264.7 cells were measured using an ELISA kit (Komabiotech Inc. Korea) according to the manufacturer's instructions. The results are shown in Table 9. In Table 9, IL6 levels were expressed as a relative percentage (%) between LPS-induced IL6 levels after the treatment with the compound of the present invention and LPS-induced IL6 levels without the treatment of the compound of the present invention.

TABLE 9

| Compound No. | Relative IL-6 levels (%) |
|---|---|
| 76 | 9.58 |
| 47 | 12 |

TABLE 9-continued

| Compound No. | Relative IL-6 levels (%) |
|---|---|
| 48 | 67 |
| 49 | 50 |
| 50 | 68 |
| 52 | 13 |
| 32 | 16 |
| 53 | 5 |
| 77 | 5 |
| 45 | 3 |
| 80 | 6 |
| 82 | 3 |
| 83 | 9 |
| 36 | 9 |
| 87 | 24 |

INDUSTRIAL APPLICABILITY

The present invention relates to a novel compound and the use of the same, can be used for the preparation of antifungal and antibacterial compositions, and can be used for the development of a pharmaceutical composition for preventing and treating fungal infection diseases.

The invention claimed is:

1. A compound represented by the following Chemical Formula 1, a stereoisomer thereof, or a pharmaceutically acceptable salt thereof:

[Formula 1]

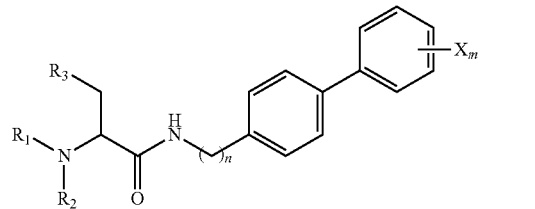

in Formula 1,
n is 2,
$R_1$, $R_2$ and $R_3$ are each independently the same as or different from each other, and
are each independently selected from hydrogen and alkyl
X is chloro.

2. The compound, the stereoisomer thereof, or the pharmaceutically acceptable salt thereof of claim 1,
wherein $R_1$ and $R_2$ are each independently H or methyl, ethyl, n-propyl, isopropyl, cyclopropyl, n-butyl, isobutyl, cyclobutyl, n-pentyl, cyclopentyl, n-hexyl or cyclohexyl, and
$R_3$ is methyl, ethyl, n-propyl, isopropyl, cyclopropyl, n-butyl, isobutyl, sec-butyl or tert-butyl.

3. An antifungal composition comprising, as an active ingredient, the compound, the stereoisomer thereof, or the pharmaceutically acceptable salt thereof of claim 1.

4. The antifungal composition of claim 3, wherein the antifungal composition exhibits antifungal activity against *Cryptococcus neoformans*, *Candida albicans*, *Candida glabrata*, or *Aspergillus fumigatus*.

5. A pharmaceutical composition for treating or preventing a fungal infectious disease, comprising, as an active ingredient, the compound, the stereoisomer thereof, or the pharmaceutically acceptable salt thereof of claim 1.

6. The pharmaceutical composition of claim 5, wherein the fungal infectious disease is caused by infections of *Cryptococcus neoformans, Candida albicans, Candida glabrata*, or *Aspergillus fumigatus*.

7. The pharmaceutical composition of claim 5, further comprising a pharmaceutically acceptable carrier, diluent or excipient.

8. An antibacterial composition comprising, as an active ingredient, the compound, the stereoisomer thereof, or the pharmaceutically acceptable salt thereof of claim 1.

9. The antibacterial composition of claim 8, wherein the antibacterial composition exhibits antibacterial activity against Gram-negative bacteria, Gram-positive bacteria, or multi-drug resistant bacteria.

10. A pharmaceutical composition for treating or preventing a bacterial infectious disease, comprising, as an active ingredient, the compound, the stereoisomer thereof, or the pharmaceutically acceptable salt thereof of claim 1.

11. A pharmaceutical composition for treating or preventing an anti-inflammatory disease, comprising the compound, the stereoisomer thereof, or the pharmaceutically acceptable salt thereof of claim 1, and a pharmaceutically acceptable carrier, diluent or excipient.

\* \* \* \* \*